US010961310B2

(12) United States Patent
Viney et al.

(10) Patent No.: US 10,961,310 B2
(45) Date of Patent: Mar. 30, 2021

(54) TARGETED IMMUNOTOLERANCE

(71) Applicant: PANDION OPERATIONS, INC., Watertown, MA (US)

(72) Inventors: Joanne L. Viney, Belmont, MA (US); Nathan Higginson-Scott, Boston, MA (US); Micah Benson, Arlington, MA (US); Alan Crane, Waban, MA (US)

(73) Assignee: PANDION OPERATIONS, INC., Watertown, MA (US)

( * ) Notice: Subject to any disclaimer, the term of this patent is extended or adjusted under 35 U.S.C. 154(b) by 75 days.

(21) Appl. No.: 15/922,592

(22) Filed: Mar. 15, 2018

(65) Prior Publication Data
US 2018/0265584 A1 Sep. 20, 2018

Related U.S. Application Data

(60) Provisional application No. 62/471,509, filed on Mar. 15, 2017.

(51) Int. Cl.
*C07K 16/28* (2006.01)
*A61P 37/06* (2006.01)
*C07K 14/705* (2006.01)
*A61K 39/00* (2006.01)

(52) U.S. Cl.
CPC .......... *C07K 16/2815* (2013.01); *A61P 37/06* (2018.01); *C07K 14/70521* (2013.01); *C07K 16/2803* (2013.01); *C07K 16/2818* (2013.01); *C07K 16/2833* (2013.01); *A61K 2039/505* (2013.01); *C07K 2317/31* (2013.01); *C07K 2317/52* (2013.01); *C07K 2317/622* (2013.01); *C07K 2317/73* (2013.01); *C07K 2317/75* (2013.01); *C07K 2319/00* (2013.01); *C07K 2319/30* (2013.01); *C07K 2319/75* (2013.01)

(58) Field of Classification Search
None
See application file for complete search history.

(56) References Cited

U.S. PATENT DOCUMENTS

| | | | |
|---|---|---|---|
| 4,518,584 A | 5/1985 | Mark et al. |
| 4,530,787 A | 7/1985 | Shaked et al. |
| 4,572,798 A | 2/1986 | Koths et al. |
| 4,766,106 A | 8/1988 | Katre et al. |
| 4,816,440 A | 3/1989 | Thomson |
| 4,853,332 A | 8/1989 | Mark et al. |
| 4,863,727 A | 9/1989 | Zimmerman et al. |
| 4,894,226 A | 1/1990 | Aldwin et al. |
| 4,902,502 A | 2/1990 | Nitecki et al. |
| RE33,653 E | 7/1991 | Mark et al. |
| 5,066,489 A | 11/1991 | Paradise et al. |
| 5,098,702 A | 3/1992 | Zimmerman et al. |
| 5,116,943 A | 5/1992 | Koths et al. |
| 5,153,310 A | 10/1992 | Mitchell et al. |
| 5,206,344 A | 4/1993 | Katre et al. |
| 5,229,109 A | 7/1993 | Grimm et al. |
| 5,425,940 A | 6/1995 | Zimmerman et al. |
| 5,776,427 A | 7/1998 | Thorpe et al. |
| 6,232,287 B1 | 5/2001 | Ruoslahti et al. |
| 6,348,192 B1 | 2/2002 | Chan et al. |
| 6,525,102 B1 | 2/2003 | Chen et al. |
| 6,579,521 B2 | 6/2003 | Sahner |
| 6,689,353 B1 | 2/2004 | Wang et al. |
| 6,927,043 B2 | 8/2005 | Chan et al. |
| 6,955,807 B1 | 10/2005 | Shanafelt et al. |
| 7,048,924 B2 | 5/2006 | Sahner |
| 7,105,653 B2 | 9/2006 | Shanafelt et al. |
| 7,132,103 B2 | 11/2006 | Goldenberg et al. |
| 7,186,804 B2 | 3/2007 | Gillies et al. |
| 7,306,801 B2 | 12/2007 | Caligiuri et al. |
| 7,371,371 B2 | 5/2008 | Epstein et al. |
| 7,462,350 B2 | 12/2008 | Gillies et al. |
| 7,514,073 B2 | 4/2009 | Epstein et al. |
| 7,569,215 B2 | 8/2009 | Wittrup et al. |
| 7,803,361 B2 | 9/2010 | Epstein et al. |
| 7,807,142 B2 | 10/2010 | Chen et al. |
| 7,888,071 B2 | 2/2011 | Gillies et al. |
| 7,951,360 B2 | 5/2011 | Wittrup et al. |
| 8,012,465 B2 | 9/2011 | Elias et al. |
| 8,124,066 B2 | 2/2012 | Epstein et al. |
| 8,349,311 B2 | 1/2013 | Wittrup et al. |
| 8,354,110 B2 | 1/2013 | Santamaria et al. |
| 8,454,963 B2 | 6/2013 | Tomlinson et al. |
| 8,759,486 B2 | 6/2014 | Leon Monzon et al. |
| 8,815,235 B2 | 8/2014 | Schnitzer et al. |
| 8,906,356 B2 | 12/2014 | Wittrup et al. |
| 8,993,731 B2 | 3/2015 | Tyson |
| 9,206,243 B2 | 12/2015 | Leon Monzon et al. |
| 9,266,938 B2 | 2/2016 | Ast et al. |
| 9,308,280 B2 | 4/2016 | Shi et al. |

(Continued)

FOREIGN PATENT DOCUMENTS

| | | |
|---|---|---|
| EP | 109748 A1 | 5/1984 |
| EP | 200280 A2 | 11/1986 |

(Continued)

OTHER PUBLICATIONS

Thomas et al. (Inflammopharmacol., 20: 1-18,2012).*
Stancovski et al. (PNAS, 88: 8691-8695, 1991).*
Jiang et al. (J. Biol. Chem., 280: 4656-4662, 2005).*
International Search Report dated Oct. 16, 2018 from corresponding PCT/US2018/034334, pp. 6.
International Written Opinion dated Oct. 16, 2018 from corresponding PCT/US2018/034334, pp. 10.
Schanzer, JM et al., A human cytokine/single-chain antibody fusion protein for s imultaneous 42-45 delivery of GM-CSF and IL-2 to Ep-CAM overexpressing tumor cells . Cancer Immunity. Feb. 17, 2006, vol. 6; p. 4; paga 2, 1s t column, 2nd and 4th paragraphs.
International Search Report dated Jul. 31, 2018 from corresponding PCT/US2018/022675, pp. 6.

(Continued)

*Primary Examiner* — Nelson B Moseley, II
(74) *Attorney, Agent, or Firm* — Troutman Pepper Hamilton Sanders LLP

(57) ABSTRACT

Methods and compounds for conferring site-specific or local immune privilege.

7 Claims, 13 Drawing Sheets

Specification includes a Sequence Listing.

(56) References Cited

U.S. PATENT DOCUMENTS

| | | |
|---|---|---|
| 9,388,231 B2 | 7/2016 | Dixit et al. |
| 9,428,567 B2 | 8/2016 | Garcia et al. |
| 9,447,159 B2 | 9/2016 | Ast et al. |
| 9,493,564 B2 | 11/2016 | Thompson et al. |
| 9,499,603 B2 | 11/2016 | Tyson |
| 9,499,605 B2 | 11/2016 | Dixit et al. |
| 9,499,634 B2 | 11/2016 | Dixit et al. |
| 9,526,797 B2 | 12/2016 | Gerdes et al. |
| 9,562,109 B2 | 2/2017 | Von Kreudenstein et al. |
| 9,574,010 B2 | 2/2017 | Spreter Von Kreudenstein et al. |
| 9,580,486 B2 | 2/2017 | Gavin et al. |
| 9,616,105 B2 | 4/2017 | Paulsen et al. |
| 9,732,134 B2 | 8/2017 | Gavin et al. |
| 9,844,582 B2 | 12/2017 | Wittrup et al. |
| 9,932,380 B2 | 4/2018 | Gavin et al. |
| 10,035,836 B1 | 7/2018 | Greve |
| 10,086,046 B2 | 10/2018 | Paulsen et al. |
| 10,093,711 B2 | 10/2018 | Kannan |
| 10,130,659 B2 | 11/2018 | Wardell et al. |
| 10,137,206 B2 | 11/2018 | Angel et al. |
| 10,138,298 B2 | 11/2018 | Rondon et al. |
| 10,150,802 B2 | 12/2018 | Garcia et al. |
| 10,166,257 B2 | 1/2019 | Wardell et al. |
| 10,166,273 B2 | 1/2019 | Wittrup et al. |
| 10,174,091 B1 | 1/2019 | Higginson-Scott et al. |
| 10,174,092 B1 | 1/2019 | Higginson-Scott et al. |
| 10,183,980 B2 | 1/2019 | Garcia et al. |
| 10,184,009 B2 | 1/2019 | Ast et al. |
| 10,202,464 B2 | 2/2019 | Ast et al. |
| 10,227,411 B2 | 3/2019 | Bernett et al. |
| 10,227,415 B2 | 3/2019 | Sprecher et al. |
| 10,232,053 B2 | 3/2019 | Hicklin et al. |
| 10,251,945 B2 | 4/2019 | Engelhardt et al. |
| 10,260,038 B2 | 4/2019 | Swee et al. |
| 10,272,113 B2 | 4/2019 | Wardell et al. |
| 10,273,489 B2 | 4/2019 | Falb et al. |
| 10,286,113 B2 | 5/2019 | Boden et al. |
| 10,293,028 B2 | 5/2019 | Klatzmann et al. |
| 10,293,058 B2 | 5/2019 | Fotin-Mleczek et al. |
| 10,294,287 B2 | 5/2019 | Greve |
| 10,294,305 B2 | 5/2019 | Loibner et al. |
| 10,301,384 B2 | 5/2019 | Vicari et al. |
| 10,308,696 B2 | 6/2019 | De Luca et al. |
| 10,316,104 B2 | 6/2019 | Ast et al. |
| 10,323,077 B2 | 6/2019 | Spencer et al. |
| 10,323,098 B2 | 6/2019 | Ast et al. |
| 10,336,801 B2 | 7/2019 | Chiou et al. |
| 10,350,266 B2 | 7/2019 | Cochran et al. |
| 10,350,304 B2 | 7/2019 | Angel et al. |
| 10,358,477 B2 | 7/2019 | Jacques et al. |
| 10,363,273 B2 | 7/2019 | Wardell et al. |
| 10,363,321 B2 | 7/2019 | Angel et al. |
| 10,376,564 B2 | 8/2019 | Klatzmann et al. |
| 10,428,145 B2 | 10/2019 | Bennett et al. |
| 10,493,148 B2 | 12/2019 | Yachi et al. |
| 10,676,516 B2 | 6/2020 | Viney et al. |
| 10,751,414 B2 | 8/2020 | Chan et al. |
| 10,766,958 B2 | 9/2020 | Ringheim |
| 2002/0041865 A1 | 4/2002 | Austin et al. |
| 2003/0021792 A1 | 1/2003 | Rohen et al. |
| 2004/0002586 A1 | 1/2004 | Nagem et al. |
| 2004/0115128 A1 | 6/2004 | Schnitzer |
| 2004/0132977 A1 | 7/2004 | Gantier et al. |
| 2005/0069521 A1 | 3/2005 | Gillies et al. |
| 2005/0201979 A1 | 9/2005 | Epstein et al. |
| 2006/0020116 A1 | 1/2006 | Gantier et al. |
| 2006/0160187 A1 | 7/2006 | Denis-Mize et al. |
| 2006/0165653 A1 | 7/2006 | Wilson |
| 2006/0234205 A1 | 10/2006 | Cao et al. |
| 2006/0251617 A1 | 11/2006 | Denis-Mize et al. |
| 2006/0263857 A1 | 11/2006 | Lefrancois et al. |
| 2006/0269515 A1 | 11/2006 | Denis-Mize et al. |
| 2007/0014765 A1 | 1/2007 | Elias et al. |
| 2007/0166308 A1 | 7/2007 | Pullen et al. |
| 2007/0269369 A1* | 11/2007 | Gegg ............... C07K 17/00 424/1.41 |
| 2008/0025947 A1 | 1/2008 | Gillies et al. |
| 2008/0260820 A1 | 10/2008 | Borrelly et al. |
| 2008/0311117 A1 | 12/2008 | Collins et al. |
| 2010/0074869 A1 | 3/2010 | Paul |
| 2010/0330029 A1 | 12/2010 | Wickham et al. |
| 2011/0150826 A1 | 6/2011 | Paulsen et al. |
| 2011/0171215 A1 | 7/2011 | Davis et al. |
| 2011/0171220 A1 | 7/2011 | Davis |
| 2011/0274650 A1 | 11/2011 | Gavin et al. |
| 2012/0207733 A1 | 8/2012 | Jacky et al. |
| 2013/0089513 A1 | 4/2013 | Chung et al. |
| 2013/0195795 A1 | 8/2013 | Gavin et al. |
| 2014/0220021 A1 | 8/2014 | Shibayama et al. |
| 2014/0286898 A1 | 9/2014 | Gavin et al. |
| 2015/0218260 A1 | 8/2015 | Klein et al. |
| 2015/0361155 A1 | 12/2015 | Tykocinski |
| 2016/0009768 A1 | 1/2016 | Davis et al. |
| 2016/0046678 A1* | 2/2016 | Roschke ............ C12N 9/0002 424/134.1 |
| 2016/0175397 A1 | 6/2016 | Umana et al. |
| 2016/0208017 A1 | 7/2016 | Ast et al. |
| 2016/0229920 A1* | 8/2016 | Ward ............... A61K 39/39558 |
| 2016/0251436 A1 | 9/2016 | Amirina et al. |
| 2016/0263240 A1 | 9/2016 | Ast et al. |
| 2016/0340397 A1 | 11/2016 | Ring et al. |
| 2017/0015722 A1 | 1/2017 | Garcia et al. |
| 2017/0037102 A1 | 2/2017 | Greve |
| 2017/0037118 A1 | 2/2017 | Berggren et al. |
| 2017/0051029 A1 | 2/2017 | Greve |
| 2017/0051057 A1 | 2/2017 | Pullen et al. |
| 2017/0056521 A1 | 3/2017 | Chang et al. |
| 2017/0081382 A1 | 3/2017 | Kannan |
| 2017/0088631 A1 | 3/2017 | Ast et al. |
| 2017/0137485 A1 | 5/2017 | Gavin et al. |
| 2017/0165326 A1 | 6/2017 | Paulsen et al. |
| 2017/0173117 A1 | 6/2017 | Paulsen et al. |
| 2017/0204154 A1 | 7/2017 | Greve |
| 2017/0209573 A1 | 7/2017 | Bacac et al. |
| 2017/0233448 A1 | 8/2017 | Malek |
| 2017/0304402 A1 | 10/2017 | Klatzmann et al. |
| 2017/0313753 A1 | 11/2017 | Gavin et al. |
| 2017/0327555 A1 | 11/2017 | Greve |
| 2018/0037624 A1 | 2/2018 | Greve |
| 2018/0125941 A1 | 5/2018 | Greve |
| 2018/0148037 A1 | 5/2018 | Pursifull et al. |
| 2018/0154012 A1 | 6/2018 | Parseghian et al. |
| 2018/0162919 A1 | 6/2018 | Greve et al. |
| 2018/0163176 A1 | 6/2018 | Lee |
| 2018/0200338 A1 | 7/2018 | Umana et al. |
| 2018/0214566 A1 | 8/2018 | Dodgson et al. |
| 2018/0228842 A1 | 8/2018 | Garcia et al. |
| 2018/0237489 A1 | 8/2018 | Kannan |
| 2018/0256747 A1 | 9/2018 | Hawthorne et al. |
| 2018/0265584 A1 | 9/2018 | Viney et al. |
| 2018/0291075 A1 | 10/2018 | Pavlakis et al. |
| 2018/0298105 A1 | 10/2018 | Andersen et al. |
| 2018/0303754 A1 | 10/2018 | Mariau et al. |
| 2018/0319859 A1 | 11/2018 | Gavin et al. |
| 2018/0326010 A1 | 11/2018 | Codarri Deak et al. |
| 2018/0326011 A1 | 11/2018 | Codarri Deak et al. |
| 2018/0334491 A1 | 11/2018 | Schmidt et al. |
| 2018/0340014 A1 | 11/2018 | Viney et al. |
| 2018/0346568 A1 | 12/2018 | Cobbold |
| 2018/0346584 A1 | 12/2018 | Sprecher et al. |
| 2018/0369329 A1 | 12/2018 | Cochran et al. |
| 2018/0371042 A1 | 12/2018 | Sahin et al. |
| 2018/0371049 A1 | 12/2018 | Boulter et al. |
| 2019/0000882 A1 | 1/2019 | Wardell et al. |
| 2019/0000883 A1 | 1/2019 | Wardell et al. |
| 2019/0000995 A1 | 1/2019 | Angel et al. |
| 2019/0000996 A1 | 1/2019 | Angel et al. |
| 2019/0000997 A1 | 1/2019 | Angel et al. |
| 2019/0002516 A1 | 1/2019 | Zhang et al. |
| 2019/0002590 A1 | 1/2019 | Bradley et al. |
| 2019/0008978 A1 | 1/2019 | Huang et al. |
| 2019/0008985 A1 | 1/2019 | Angel et al. |
| 2019/0016793 A1 | 1/2019 | Cini et al. |

(56) References Cited

U.S. PATENT DOCUMENTS

| | | |
|---|---|---|
| 2019/0016796 A1 | 1/2019 | Boyman et al. |
| 2019/0016797 A1 | 1/2019 | Arenas-Ramirez et al. |
| 2019/0022154 A1 | 1/2019 | Rottiers et al. |
| 2019/0022186 A1 | 1/2019 | Ragheb |
| 2019/0023760 A1 | 1/2019 | Bode et al. |
| 2019/0023795 A1 | 1/2019 | Tveita |
| 2019/0046664 A1 | 2/2019 | Schnieders et al. |
| 2019/0054145 A1 | 2/2019 | Wittrup et al. |
| 2019/0054189 A1 | 2/2019 | Fotin-Mleczek et al. |
| 2019/0062395 A1 | 2/2019 | Merchant et al. |
| 2019/0070222 A1 | 3/2019 | Wardell et al. |
| 2019/0071472 A1 | 3/2019 | Bishai et al. |
| 2019/0071500 A1 | 3/2019 | Kley et al. |
| 2019/0076515 A1 | 3/2019 | Engelhardt et al. |
| 2019/0077881 A1 | 3/2019 | Ast et al. |
| 2019/0083536 A1 | 3/2019 | Wardell et al. |
| 2019/0083538 A1 | 3/2019 | Wardell et al. |
| 2019/0083539 A1 | 3/2019 | Wardell et al. |
| 2019/0083635 A1 | 3/2019 | Xie et al. |
| 2019/0092831 A1 | 3/2019 | Krupnick et al. |
| 2019/0092871 A1 | 3/2019 | Tavernier et al. |
| 2019/0106488 A1 | 4/2019 | Rondon et al. |
| 2019/0112394 A1 | 4/2019 | Ploegh et al. |
| 2019/0119345 A1 | 4/2019 | Krupnick et al. |
| 2019/0119346 A1 | 4/2019 | Garcia et al. |
| 2019/0125840 A1 | 5/2019 | Berdel et al. |
| 2019/0125852 A1 | 5/2019 | Jones et al. |
| 2019/0127451 A1 | 5/2019 | Gebleux et al. |
| 2019/0134174 A1 | 5/2019 | Jones et al. |
| 2019/0134195 A1 | 5/2019 | Jones et al. |
| 2019/0136186 A1 | 5/2019 | Germeroth et al. |
| 2019/0142967 A1 | 5/2019 | Hicklin et al. |
| 2019/0144553 A1 | 5/2019 | Kley et al. |
| 2019/0151364 A1 | 5/2019 | Klatzmann |
| 2019/0151469 A1 | 5/2019 | Fotin-Mleczek et al. |
| 2019/0153058 A1 | 5/2019 | Greve |
| 2019/0153471 A1 | 5/2019 | Paul et al. |
| 2019/0160115 A1 | 5/2019 | Falb et al. |
| 2019/0169254 A1 | 6/2019 | Higginson-Scott et al. |
| 2019/0169255 A1 | 6/2019 | Higginson-Scott et al. |
| 2019/0175651 A1 | 6/2019 | Lee et al. |
| 2019/0175705 A1 | 6/2019 | Engelhardt et al. |
| 2019/0177746 A1 | 6/2019 | Peddareddigari et al. |
| 2019/0183933 A1 | 6/2019 | Garcia et al. |
| 2019/0185550 A1 | 6/2019 | Ji et al. |
| 2019/0194292 A1 | 6/2019 | Luo et al. |
| 2019/0202881 A1 | 7/2019 | Greve |
| 2019/0202882 A1 | 7/2019 | Greve |
| 2019/0202917 A1 | 7/2019 | Campbell et al. |
| 2019/0211079 A1 | 7/2019 | Davis et al. |
| 2019/0216898 A1 | 7/2019 | Wang et al. |
| 2019/0218311 A1 | 7/2019 | Loew et al. |
| 2019/0225710 A1 | 7/2019 | Ali et al. |
| 2019/0231820 A1 | 8/2019 | Fardis |
| 2019/0241638 A1 | 8/2019 | Bernett et al. |
| 2020/0181249 A1 | 6/2020 | Curtis et al. |

FOREIGN PATENT DOCUMENTS

| | | | |
|---|---|---|---|
| EP | 234599 A1 | 9/1987 | |
| EP | 673257 A1 | 9/1995 | |
| EP | 840622 A1 | 5/1998 | |
| EP | 1076704 A1 | 2/2001 | |
| EP | 1220682 A1 | 7/2002 | |
| EP | 1370280 A2 | 12/2003 | |
| EP | 1454138 A2 | 9/2004 | |
| EP | 1648931 A2 | 4/2006 | |
| EP | 1668030 A1 | 6/2006 | |
| EP | 1944318 A1 | 7/2008 | |
| EP | 2225397 A1 | 9/2010 | |
| EP | 2288372 A2 | 3/2011 | |
| EP | 1987845 B1 | 3/2012 | |
| EP | 1442750 B1 | 8/2012 | |
| EP | 2505206 A2 | 10/2012 | |
| EP | 2639241 A2 | 9/2013 | |
| EP | 2673294 A1 | 12/2013 | |
| EP | 3237446 A1 | 11/2017 | |
| EP | 2683395 B1 | 8/2018 | |
| EP | 3075745 B1 | 9/2018 | |
| EP | 2882777 B1 | 10/2018 | |
| EP | 2702074 B1 | 11/2018 | |
| EP | 3102595 B1 | 11/2018 | |
| EP | 3405482 A1 | 11/2018 | |
| EP | 3180020 B1 | 12/2018 | |
| EP | 3411414 A2 | 12/2018 | |
| EP | 3211000 B1 | 1/2019 | |
| EP | 3421495 A2 | 1/2019 | |
| EP | 3426785 A1 | 1/2019 | |
| EP | 3431096 A1 | 1/2019 | |
| EP | 3434695 A1 | 1/2019 | |
| EP | 3448874 A1 | 3/2019 | |
| EP | 3453401 A1 | 3/2019 | |
| EP | 2970423 B1 | 4/2019 | |
| EP | 3463440 A1 | 4/2019 | |
| EP | 3463450 A1 | 4/2019 | |
| EP | 3463577 A1 | 4/2019 | |
| EP | 3464560 A1 | 4/2019 | |
| EP | 3481412 A1 | 5/2019 | |
| EP | 3482766 A1 | 5/2019 | |
| EP | 3484508 A1 | 5/2019 | |
| EP | 3484509 A1 | 5/2019 | |
| EP | 3489255 A1 | 5/2019 | |
| EP | 3500290 A1 | 6/2019 | |
| EP | 3502134 A1 | 6/2019 | |
| EP | 3134102 B1 | 7/2019 | |
| EP | 3508496 A1 | 7/2019 | |
| EP | 3514168 A1 | 7/2019 | |
| JP | 2015157824 A | 9/2015 | |
| WO | 1989004665 A2 | 6/1989 | |
| WO | 1991002000 A1 | 2/1991 | |
| WO | 2000006605 A2 | 2/2000 | |
| WO | 2004041862 | 5/2004 | |
| WO | 2004041862 A3 | 6/2004 | |
| WO | 2004056875 A1 | 7/2004 | |
| WO | 2005067620 A2 | 7/2005 | |
| WO | 2006121168 A1 | 11/2006 | |
| WO | 2008124858 A2 | 10/2008 | |
| WO | 2010029434 A1 | 3/2010 | |
| WO | 2010029435 | 3/2010 | |
| WO | 2010029435 A1 | 3/2010 | |
| WO | WO 2012/029435 * | 3/2010 | ............ C07K 16/28 |
| WO | 2010085495 A1 | 7/2010 | |
| WO | 2012119093 A1 | 9/2012 | |
| WO | 2014012479 | 1/2014 | |
| WO | 2014100014 A1 | 6/2014 | |
| WO | 2014153111 A2 | 9/2014 | |
| WO | 2015112800 A1 | 7/2015 | |
| WO | 2016014428 A2 | 1/2016 | |
| WO | 2016025385 A1 | 2/2016 | |
| WO | 2016020856 A3 | 3/2016 | |
| WO | 2016065323 | 4/2016 | |
| WO | 2016065323 A3 | 6/2016 | |
| WO | 2016100375 A2 | 6/2016 | |
| WO | 2016115168 A1 | 7/2016 | |
| WO | 2016149201 A2 | 9/2016 | |
| WO | 2016164937 A2 | 10/2016 | |
| WO | 2016179430 A1 | 11/2016 | |
| WO | 2016201304 A1 | 12/2016 | |
| WO | 2016210129 A1 | 12/2016 | |
| WO | 2016164937 A3 | 1/2017 | |
| WO | 2017044464 A1 | 3/2017 | |
| WO | 2017070649 A1 | 4/2017 | |
| WO | 2017122180 A1 | 7/2017 | |
| WO | 2017201432 A2 | 11/2017 | |
| WO | 2017202786 A1 | 11/2017 | |
| WO | 2017205810 A1 | 11/2017 | |
| WO | 2017210562 A1 | 12/2017 | |
| WO | 2017210579 A1 | 12/2017 | |
| WO | 2017210649 A1 | 12/2017 | |
| WO | 2017220704 A1 | 12/2017 | |
| WO | 2018011803 A1 | 1/2018 | |
| WO | 2018064594 A2 | 4/2018 | |
| WO | 2018089669 A2 | 5/2018 | |
| WO | 2018112069 A1 | 6/2018 | |

(56) References Cited

FOREIGN PATENT DOCUMENTS

| | | |
|---|---|---|
| WO | 2018119114 A1 | 6/2018 |
| WO | 2018129188 A1 | 7/2018 |
| WO | 2018129207 A1 | 7/2018 |
| WO | 2018129332 A1 | 7/2018 |
| WO | 2018129346 A1 | 7/2018 |
| WO | 2018132516 A1 | 7/2018 |
| WO | 2018145033 A1 | 8/2018 |
| WO | 2018160877 A1 | 9/2018 |
| WO | 2018170168 A1 | 9/2018 |
| WO | 2018170288 | 9/2018 |
| WO | 2018170288 A1 | 9/2018 |
| WO | 2018184484 A1 | 10/2018 |
| WO | 2018189220 A1 | 10/2018 |
| WO | 2018209115 A1 | 11/2018 |
| WO | 2018213192 A1 | 11/2018 |
| WO | 2018215935 A1 | 11/2018 |
| WO | 2018215936 A1 | 11/2018 |
| WO | 2018215938 A1 | 11/2018 |
| WO | 2018217989 A1 | 11/2018 |
| WO | 2018226714 A1 | 12/2018 |
| WO | 2018228442 A1 | 12/2018 |
| WO | 2018231759 A1 | 12/2018 |
| WO | 2018234793 A2 | 12/2018 |
| WO | 2019010224 A1 | 1/2019 |
| WO | 2019014391 A1 | 1/2019 |
| WO | 2019025545 A1 | 2/2019 |
| WO | 2019028419 A1 | 2/2019 |
| WO | 2019028425 A1 | 2/2019 |
| WO | 2019032661 A1 | 2/2019 |
| WO | 2019032662 A1 | 2/2019 |
| WO | 2019032663 A1 | 2/2019 |
| WO | 2019035938 A1 | 2/2019 |
| WO | 2019046815 A1 | 3/2019 |
| WO | 2019051091 A1 | 3/2019 |
| WO | 2019051094 A1 | 3/2019 |
| WO | 2019051126 A1 | 3/2019 |
| WO | 2019051127 A1 | 3/2019 |
| WO | 2019051424 A2 | 3/2019 |
| WO | 2019062877 A1 | 4/2019 |
| WO | 2019067766 A1 | 4/2019 |
| WO | 2019084284 A1 | 5/2019 |
| WO | 2019091384 A1 | 5/2019 |
| WO | 2019092504 A1 | 5/2019 |
| WO | 2019100023 A1 | 5/2019 |
| WO | 2019103857 A1 | 5/2019 |
| WO | 2019104092 A1 | 5/2019 |
| WO | 2019112852 A1 | 6/2019 |
| WO | 2019112854 A1 | 6/2019 |
| WO | 2019113221 A1 | 6/2019 |
| WO | 2019118475 A1 | 6/2019 |
| WO | 2019118873 A2 | 6/2019 |
| WO | 2019122025 A1 | 6/2019 |
| WO | 2019122882 A1 | 6/2019 |
| WO | 2019122884 A1 | 6/2019 |
| WO | 2019125732 A1 | 6/2019 |
| WO | 2019126574 A1 | 6/2019 |
| WO | 2019129053 A1 | 7/2019 |
| WO | 2019129644 A1 | 7/2019 |
| WO | 2019131964 A1 | 7/2019 |
| WO | 2019136456 A1 | 7/2019 |
| WO | 2019136459 A1 | 7/2019 |
| WO | 2019139896 A1 | 7/2019 |
| WO | 2019144309 A1 | 8/2019 |
| WO | 2019147837 A2 | 8/2019 |
| WO | 2019173636 A1 | 9/2019 |
| WO | 2019173832 A2 | 9/2019 |
| YE | 2020020783 | 1/2020 |

OTHER PUBLICATIONS

International Written Opinion dated Jul. 31, 2018 from corresponding PCT/US2018/022675, pp. 11.
Altschul et al., (1997) Nucleic Acids Res. 25:3389-3402.
Chen J et al (2003). Nat Struct Biol. 10, 995-1001.
Clements et al. 2005 PNAS 102:3360.
Colgan et al., Physiological roles for ecto-5'-nucleotidase (CD73), Purinergic Signalling, Jun. 2006, 2:351.
Day et al (2002). Cell Commun Adhes. 9, 205-219.
De Chateau M et al (Nov. 20, 2001). Biochemistry. 40(46), 13972-13979.
Fridrich et al. 2016 PLoS One 11:e0153290; doi: 10.1371/journal.pone.0153290.
Gayle, et al., J Clin Invest. May 1, 1998; 101(9): 1851-1859.
Hahn et al. 2013 Blood 15:1182.
Hoshino H et al (2011). J Histochem Cytochem. 59, 572-583.
Leung E et al (2004). Immunol Cell Biol. 82. 400-409.
Nakache, M et al (Jan. 12, 1989). Nature. 337(6203), 179-181.
Pullen N et al (2009). B J Pharmacol. 157. 281-293.
Qi J et al (2012). J Biol Chem. 287. 15749-15759).
Soler D et al (2009). J Pharmacol Exp Ther. 330. 864-875.
Streeter, PR et al (Jan. 7, 1988). Nature. 331(6151). 41-46.
Viney JL et al. (1996). J Immunol. 157:6, 2488-2497.
Yang Y et al (1995). Scared J Immunol. 42. 235-247.
Yegutkin et al. FASEB J. Sep. 2012; 26(9):3875-83.
Yegutkin G, Bodin P, Burnstock G. Br J Pharmacol 2000; 129: 921-6.
Yu Y et al (2012). J Cell Biol. 196, 131-146.
Yu Y et al (2013). J Biol Chem. 288, 6284-6294.
Tran et al. 2009 PNAS 106:13445.
Wang et al. 2009 PNAS 106:13439.
Levin et al., "Exploiting a natural conformational switch to engineer an Interleukin-2 superkine", Nature (2012) 484 (7395): 529-533.
Ghelani et al., "Defining the Treshohold IL-2 Signal Required for Induction of Selective Treg Cell Responsees Using Engineered IL-2 Muteins" Frontiers in Immunology (2020) vol. 11:1106, pp. 1-27.
Non-Final Office Action dated May 28, 2019 in U.S. Appl. No. 16/229,133.
Non-final Office Action in U.S. Appl. 16/693,741 dated Sep. 24, 2020.
Non-Final Office Action dated Sep. 22, 2020 in U.S. Appl. No. 16/693,693.
Patsoukis et al., PD-1 Increased PTEN Phosphatase Activity While Decreasing PTEN Protein Stability by Inhibiting Casein Kinase 2. MCB, 2013, 33(16):3091-3098.
Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses. J Immunol, 2003, 170(2):711-718.
Notice of Allowance dated Feb. 26, 2020 in U.S. Appl. No. 15/988,311.
Final Office Action dated Dec. 9, 2019 in U.S. Appl. No. 15/988,311.
Mikayama et al., "Molecular cloning and functional expression of a cDNA encoding glycosylation-inhibiting factor", Proc. Natl. Acad. Sci. USA (1993) vol. 90, pp. 10056-10060.
Voet et al, Biochemistry John Wiley & Sons,Inc. (1990) pp. 126-128 and 228-234.
Akkaya. Ph.D. Thesis: Modulation of the PD-1 pathway by inhibitor antibody superagonists. Chirst Church College, Oxford, UK, 2012.
Genbank accession # NP_001767.3.
GenBank AAH65937.1.
GenBank P17693.1.
Needleman and Wunsch (1970) J. Mol. Biol. 48:444-453.
E. Meyers and W. Miller (1989) CABIOS, 4:11-17.
Altschul, et al. (1990) J. Mol. Biol. 215:403-10.
LeMaoult et al., 2013 The FASEB Journal 27:3643.
Hald et al. 2012 Diabetelogia 55:154.
Hodgin et al, Am J Pathol 177:1675 2010.
Hu et al Arth and Rheum 56:3588 2007.
Wang et al Arth and Rheum 54:2271 2006.
Yang and Cotsarelis, J Dermatol Sci 57:2 2010.
Non-final Office Action in U.S. Appl. No. 15/988,311, now U.S. Pat. No. 10,676,516, dated Sep. 12, 2019.
Matthieu Collin: "Immune checkpoint inhibitors: a patent review (2010-2015)", Expert Opinion on Therapeutic Patents, vol. 26, No. 5, Apr. 18, 2016 (Apr. 18, 2016), pp. 555-564, XP055294986, GB ISSN: 1354-3776, DOI: 10.1080/13543776.2016.1176150.

(56) References Cited

OTHER PUBLICATIONS

Melissa Barsanelli et al. "From targeting the tumor to targeting the immune system: Transversal challenges in oncology with the inhibition of the PD-1/PD-L1 axis", World Journal of Clinical Oncology, vol. 8, No. 1, Feb. 10, 2017 (Feb. 10, 2017), p. 37, XP055748103, US ISSN: 2218-4333, DOI: 10.5306/wcjo.v8.i1.37.

Bersanelli, et at., "From targeting the tumor to targeting the immune system: Transversal challenges in oncology with the inhibition of the PD-1/PD-L1 axis", World J Clin Oncol (2017) 8(1):37-53.

* cited by examiner

Orientation 1

PD-1 Agonist anti-MAdCAM-1

Orientation 2

Anti-MAdCAM-1

PD-1 Agonist

SEQUENCE LISTING

```
<160> NUMBER OF SEQ ID NOS: 9

<210> SEQ ID NO 1
<211> LENGTH: 510
<212> TYPE: PRT
<213> ORGANISM: Homo sapiens

<400> SEQUENCE: 1

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240
```

```
Leu Tyr Gly Lys Asp Tyr Asn Val Tyr Thr His Ser Phe Leu Cys Tyr
            245                 250                 255

Gly Lys Asp Gln Ala Leu Trp Gln Lys Leu Ala Lys Asp Ile Gln Val
        260                 265                 270

Ala Ser Asn Glu Ile Leu Arg Asp Pro Cys Phe His Pro Gly Tyr Lys
    275                 280                 285

Lys Val Val Asn Val Ser Asp Leu Tyr Lys Thr Pro Cys Thr Lys Arg
290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510

<210> SEQ ID NO 2
<211> LENGTH: 574
<212> TYPE: PRT
<213> ORGANISM: Homo sapiens

<400> SEQUENCE: 2

Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110
```

```
Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
            195                 200                 205

Thr Leu Asn Val Asn Lys Ile Ile Ala Leu Gly His Ser Gly Phe Glu
210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
            245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
            275                 280                 285

Tyr Leu Lys Ile Glu Phe Asp Glu Arg Gly Asn Val Ile Ser Ser His
            290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
            325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
            355                 360                 365

Ile Asn Asn Asn Leu Arg His Ala Asp Glu Thr Phe Trp Asn His Val
            370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
            405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
            450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
            485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525
```

```
Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570
```

<210> SEQ ID NO 3
<211> LENGTH: 290
<212> TYPE: PRT
<213> ORGANISM: Homo sapiens

<400> SEQUENCE: 3

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
    115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
    195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
    275                 280                 285

Glu Thr
    290
```

<210> SEQ ID NO 4
<211> LENGTH: 313
<212> TYPE: PRT
<213> ORGANISM: Homo sapiens

```
<400> SEQUENCE: 4

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
290                 295                 300

Thr Ile Pro Ile Met Gly Ile Val Ala
305                 310

<210> SEQ ID NO 5
<211> LENGTH: 338
<212> TYPE: PRT
<213> ORGANISM: Homo sapiens

<400> SEQUENCE: 5

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45
```

```
Met Gly Tyr Val Asp Asp Thr Gln Phe Val Arg Phe Asp Ser Asp Ser
 50                  55                  60

Ala Cys Pro Arg Met Glu Pro Arg Ala Pro Trp Val Glu Gln Glu Gly
 65                  70                  75                  80

Pro Glu Tyr Trp Glu Glu Glu Thr Arg Asn Thr Lys Ala His Ala Gln
                 85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 6
<211> LENGTH: 5
<212> TYPE: PRT
<213> ORGANISM: Artificial Sequence
<220> FEATURE:
<223> OTHER INFORMATION: synthetic sequence

<400> SEQUENCE: 6

Gly Gly Gly Gly Ser
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic sequence

<400> SEQUENCE: 7
```

```
Gly Gly Gly Gly Ser Gly Gly Gly Gly Ser
1               5                   10

<210> SEQ ID NO 8
<211> LENGTH: 15
<212> TYPE: PRT
<213> ORGANISM: Artificial Sequence
<220> FEATURE:
<223> OTHER INFORMATION: synthetic sequence

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 20
<212> TYPE: PRT
<213> ORGANISM: Artificial Sequence
<220> FEATURE:
<223> OTHER INFORMATION: synthetic sequence

<400> SEQUENCE: 9

Gly Gly Gly Gly Ser Gly Gly Gly Gly Ser Gly Gly Gly Gly Ser Gly
1               5                   10                  15

Gly Gly Gly Ser
            20
```

TARGETED IMMUNOTOLERANCE

CROSS-REFERENCE TO RELATED APPLICATIONS

This application claims priority to U.S. Provisional Application No. 62/471,509, filed Mar. 15, 2017, which is hereby incorporated by reference in its entirety.

FIELD

The embodiments provided herein relate to, for example, methods and compositions for local or targeted immune-privilege.

BACKGROUND

Instances of unwanted immune responses, e.g., as in the rejection of transplanted tissue or in autoimmune disorders, constitute a major health problem for millions of people across the world. Long-term outcomes for organ transplantation are frequently characterized by chronic rejection, and eventual failure of the transplanted organ. More than twenty autoimmune disorders are known, affecting essentially every organ of the body, and affecting over fifty million people in North America alone. The broadly active immunosuppressive medications used to combat the pathogenic immune response in both scenarios have serious side effects.

SUMMARY

Disclosed herein are methods and therapeutic compounds that provide site-specific immune privilege. Embodiments disclosed herein are incorporated by reference into this section.

In some embodiments, the therapeutic compound comprises an engineered multi-specific compound, e.g., an engineered bi-specific molecule, e.g., an engineered bi-specific antibody molecule, comprising:
  1) a specific targeting moiety selected from:
  a) a donor specific targeting moiety which, e.g., preferentially binds a donor target (preferentially as compared with binding to a recipient antigen), and is useful for providing site-specific immune privilege for a transplant tissue, e.g., an organ, from a donor; or
  b) a tissue specific targeting moiety which, e.g., preferentially binds a subject target tissue (preferentially as compared with subject non-target tissue), and is useful for providing site-specific immune privilege for a subject tissue undergoing unwanted immune attack, e.g., in an autoimmune disorder); and
  2) an effector binding/modulating moiety selected from:
  (a) an immune cell inhibitory molecule binding/modulating moiety (referred to herein as an ICIM binding/modulating moiety);
  (b) an immunosuppressive immune cell binding/modulating moiety (referred to herein as an IIC binding/modulating moiety); or
  (c) an effector binding/modulating moiety that, as part of a therapeutic compound, promotes an immuno-suppressive local microenvironment, e.g., by providing in the proximity of the target, a substance that inhibits or minimizes attack by the immune system of the target (referred to herein as an SM binding/modulating moiety).

An effector binding/modulating moiety can fall into more than one of classes a, b and c. E.g., as is shown below, a CTLA4 binding molecule falls into both of categories a and b.

In some embodiments, the therapeutic compound comprises an ICIM binding/modulating moiety. In some embodiments, an ICIM binding/modulating molecule and binds, and agonizes, an inhibitory molecule, e.g., an inhibitory immune checkpoint molecule, or otherwise inhibits or reduces the activity of an immune cell, e.g., a cytotoxic T cell, a B cell, NK cell, or a myeloid cell, e.g., a neutrophil or macrophage.

In some embodiments, the therapeutic compound comprises an engineered multi-specific compound, e.g., an engineered bi-specific molecule, e.g., an engineered bi-specific antibody molecule, comprising:
  1) a specific targeting moiety, e.g., a donor specific targeting moiety (which binds a donor target and is useful for providing site-specific immune privilege for a transplant tissue, e.g., an organ, from a donor) or a tissue specific targeting moiety (which binds a subject tissue target and is useful for providing site-specific immune privilege for a subject tissue undergoing unwanted immune attack, e.g., in an autoimmune disorder); and
  2) an effector binding/modulating moiety comprising an ICIM binding/modulating moiety that binds to an effector molecule on an immune cell, e.g., an inhibitory receptor, e.g., PD-1, wherein, upon binding of the specific targeting moiety to its target, and binding of the ICIM binding/modulating moiety to an effector molecule on the immune cell, an immune cell activity, e.g., the ability of the immune cell to mount an immune attack, is down regulated, e.g., through an inhibitory signal dependent on the clustering of effector molecules on the immune cell. In some embodiments, the engineered multi-specific compound comprises additional binding moieties so that it binds more than two specific molecules, such as, but not limited to, 3 or 4.

In some embodiments, the therapeutic compound comprises an ICIM binding/modulating moiety and has one or both of the following properties: (a) the level of down regulation of an immune cell is greater when the therapeutic compound is bound to its target than when the therapeutic compound is not bound to its target; and (b) the therapeutic compound, when engaged with a cell surface inhibitory receptor, e.g., PD-1, on an immune cell, does not inhibit, or does not substantially inhibit the ability of the cell surface inhibitory receptor to bind an endogenous ligand.

In some embodiments, the level of down regulation of an immune cell is greater when the therapeutic compound is bound to its target than when the therapeutic compound is not bound to its target. In embodiments, the level of down regulation by target bound therapeutic compound is equal to or greater than 1.5-fold, 2-fold, 4-fold, 8-fold or 10-fold greater than what is seen when it is not bound to its target. In embodiments, therapeutic compound does not, or does not significantly down regulate immune cells when it is not bound to target. Thus, indiscriminant or unwanted agonism of an inhibitory receptor, e.g., PD-1, is minimized or eliminated. E.g., when the therapeutic compound is bound to an immune cell, but not bound to the targeted moiety, engagement of a inhibitory immune checkpoint molecule by the therapeutic compound does not result in down regulation or does not result in substantia down regulation, e.g., the inhibitory receptor on the immune cell to which the therapeutic compound is bound, is not clustered or not clustered sufficiently to result in an inhibitory signal sufficient to give down regulation or substantial inhibition of the immune cell.

In embodiments, the therapeutic compound, when engaged with a cell surface inhibitory receptor, e.g., PD-1, on an immune cell, does not inhibit, or does not substantially inhibit the ability of the cell surface inhibitory receptor to bind an endogenous ligand. In some embodiments, the therapeutic compound can bind to the PD-L1/2 binding site on PD-1. Thus, indiscriminant or unwanted antagonism of an inhibitory receptor, e.g., PD-1, is minimized or eliminated. In embodiments, binding of the therapeutic compound to an inhibitory receptor, e.g. PD-1, on an immune cell does not impede, or substantially impede, the ability of the inhibitory receptor to bind a natural ligand, e.g., PD-L1. In embodiments, binding of the therapeutic compound to an inhibitory receptor, e.g. PD-1, on an immune reduces binding of a natural ligand, e.g., PD-L1, by less than 50, 40, 30, 20, 10, or 5% of what is seen in the absence of therapeutic compound.

In some embodiments, the therapeutic compound comprises an ICIM binding/modulating moiety and, when administered to a subject at a therapeutically effective dose, does not result in unacceptable levels of systemic immune suppression, as would be possible if indiscriminant agonism of the inhibitory receptor in all immune cells of a type, e.g., all T cells, occurred, or unacceptable levels of systemic immune activation, as would be possible if the therapeutic compound antagonized the interaction of the inhibitory receptor with its natural ligand.

While not wishing to be bound by theory, it is believed that, upon administration to a subject, a therapeutic compound comprising an ICIM binding/modulating moiety can exist in any one of four states: i) unbound and in free solution; ii) bound to only an inhibitory receptor expressed on the surface of an immune cell, e.g., a T cell, through the ICIM binding/modulating moiety; iii) bound to only the surface of the target transplant or subject tissue through the targeting moiety; and iv) bound to both the surface of target transplant or subject tissue through the targeting moiety and to an inhibitory receptor expressed by an immune cell, e.g., a T cell, through the ICIM binding/modulating moiety. When the therapeutic compound is bound only to the target transplant or subject tissue (iii) through the targeting moiety, it has no, or no substantial, effect on the target transplant or tissue. When the therapeutic compound is bound to the target transplant or tissue through the targeting moiety and bound to an inhibitory receptor expressed by an immune cell, e.g., a T cell, through the ICIM binding/modulating moiety (iv), it creates immune privilege at the target organ or tissue. While not wishing to be bound by theory, is believed that this is achieved by the target transplant or donor tissue multimerizing the therapeutic compound molecules on its surface, e.g., by immobilizing a plurality of therapeutic compound molecules at a high density and valency. The multimerization of the therapeutic compound molecules allows the ICIM binding/modulating moieties of the therapeutic compounds to promote clustering of inhibitory receptors expressed on the surface of the immune cell, e.g., a pathogenic T cell, and transmission of an inhibitory signal functioning to silence or down-regulate the immune cell. E.g., in the case of T cells, a therapeutic compound comprising an ICIM binding/modulating moiety comprising a PD-L1 molecule, or an anti-PD-1 Ab, can be used. Binding of a plurality of the therapeutic compound molecules to the target results in multimerization of the therapeutic compound molecules, which in turn, by virtue of the PD-L1 molecule, or a functional anti-PD-1 antibody molecule, leads to clustering of PD-1 on the T cell. If that clustering occurs in the context of antigen presentation by the target MHC, to T cell receptor on the T cell, a negative signal is generated and the T cell will be inactivated. In embodiments the ICIM binding/modulating moiety, e.g., a functional antibody molecule, binds the effector molecule but does not inhibit, or substantially inhibit, interaction of the effector molecule with its native ligand(s).

In some embodiments, the therapeutic compound comprises an IIC binding/modulating moiety, which binds and recruits an immune suppressive immune cell, e.g., a Treg, e.g., a Foxp3+CD25+ Treg, to the proximity of the target tissue.

In some embodiments, the therapeutic compound comprises a SM binding/modulating moiety, which modulates, e.g., binds and inhibits, sequesters, degrades or otherwise neutralizes a substance, e.g., a soluble molecule that modulates an immune response, e.g., ATP or AMP.

In some embodiments, the therapeutic compound comprises a targeting moiety that is specific for a target on an immune cell. In some embodiments, the target is as described herein. In some embodiments, the target is MAdCAM. In some embodiments, the targeting moiety is an antibody that binds to MAdCAM.

In some embodiments, the therapeutic compound comprises a donor specific targeting moiety and provides site-specific immune privilege for donor transplant tissue implanted in a subject. In some embodiments, the therapeutic compound comprises a tissue specific targeting moiety and provides site-specific immune privilege for a tissue of a subject, e.g., a tissue afflicted with an unwanted immune response in an autoimmune disorder.

The targeting moiety is specific for the donor transplant or subject tissue to be protected from the immune system. In some embodiments, the effector molecule binding moiety comprises a de novo generated binding domain, e.g. a functional antibody molecule. In some embodiments, the effector binding/modulating moiety comprises amino acid sequence deriving from the natural ligand that recognizes an inhibitory receptor expressed on the surface of an immune cell, e.g., a T cell.

In some embodiments, the therapeutic compound silences immune cells, e.g., T cells, proximal to the transplant or donor tissue to be protected but does not silence immune cells, e.g., T cells, not proximal to the target, as the therapeutic compound requires the presence of the target transplant or donor tissue for function. This in contrast to when the therapeutic compound binds only to the inhibitory receptor expressed by the immune cell, e.g., T cell, in which case there is no functional consequence.

Methods and therapeutic compounds described here are based at least in part on providing site-specific immune-privilege. Therapeutic compounds and method of using them described herein allow the minimization, e.g., the reduction or elimination of, non-site specific systemic administration of immune-suppressive therapeutic agents in clinical settings, e.g., where reversal and suppression of an immune response is desired, such as in autoimmune diseases or tissue, e.g., organ, transplant. While capable of clinically meaningful response when the underlying pathophysiology driven by an aberrant immune system is impacted, broadly acting immunosuppressants have the undesirable effect of reducing the patient's systemic immune system function. As the role of a normally functioning immune system is to combat the constant barrage of pathogenic and opportunistic organisms existing in the surrounding environment and to constantly purge healthy individuals of cancerous cells, patients undergoing chronic immunosuppression are at an increased risk to develop infections and cancer. Methods and therapeutic compounds described herein provide therapies that selectively target and attenuate, reduce, or extinguish only the pathogenic immune response at the site of pathology while having minimal inhibition of normal systemic immune system function elsewhere.

In some embodiments, a therapeutic compound is provided as provided herein. In some embodiments, the compound comprises a i) a specific targeting moiety selected from: a) a donor specific targeting moiety which, e.g., preferentially binds a donor target; or b) a tissue specific targeting moiety which, e.g., preferentially binds target tissue of a subject; and ii) an effector binding/modulating moiety selected from: (a) an immune cell inhibitory molecule binding/modulating moiety (ICIM binding/modulating moiety); (b) an immunosuppressive immune cell binding/modulating moiety (IIC binding/modulating moiety); or (c) an effector binding/modulating moiety that, as part of a therapeutic compound, promotes an immuno-suppressive local microenvironment, e.g., by providing in the proximity of the target, a substance that inhibits or minimizes attack by the immune system of the target (SM binding/modulating moiety).

In some embodiments, the effector binding/modulating moiety comprises an ICIM binding/modulating moiety. In some embodiments, the effector binding/modulating moiety comprises an ICIM binding/modulating moiety comprising an inhibitory immune checkpoint molecule ligand molecule. In some embodiments, the inhibitory immune molecule counter-ligand molecule comprises a PD-L1 molecule. In some embodiments, the ICIM is wherein the inhibitory immune molecule counter ligand molecule engages a cognate inhibitory immune checkpoint molecule selected from PD-1, KIR2DL4, LILRB1, LILRB, or CTLA-4. In some embodiments, the ICIM is an antibody. In some embodiments, the ICIM comprises an antibody that binds to PD-1, KIR2DL4, LILRB1, LILRB, or CTLA-4. In some embodiments, the ICIM binding/modulating moiety which comprises a functional antibody molecule to a cell surface inhibitory molecule.

In some embodiments, the cell surface inhibitory molecule is an inhibitory immune checkpoint molecule. In some embodiments, the inhibitory immune checkpoint molecule is selected from PD-1, KIR2DL4, LILRB1, LILRB2, CTLA-4, or selected from Table 1.

In some embodiments, the effector binding/modulating moiety comprises an IIC binding/modulating moiety.

In some embodiments, the compound has the formula from N-terminus to C-terminus:
R1—Linker Region A—R2 or R3—Linker Region B—R4, wherein, R1, R2, R3, and R4, each independently comprises an effector binding/modulating moiety, e.g., an ICIM binding/modulating moiety, an IIC binding/modulating moiety, or an SM binding/modulating moiety; a specific targeting moiety; or is absent; provided that an effector binding/modulating moiety and a specific targeting moiety are present.

In some embodiments, methods of treating auto-immune diseases or conditions are provided herein, the methods comprising administering one or more of the therapeutic compounds provided herein.

In some embodiments, methods of treating diseases or conditions described herein are provided herein, the methods comprising administering one or more of the therapeutic compounds provided herein.

In some embodiments, methods of treating a subject with inflammatory bowel disease are provided, the methods comprising administering a therapeutic compound provided herein to the subject to treat the inflammatory bowel disease. In some embodiments, the subject has Crohn's disease and or ulcerative colitis.

In some embodiments, methods of treating a subject with auto-immune hepatitis are provided, the methods comprising administering a therapeutic compound as provided herein to the subject to treat the auto-immune hepatitis.

In some embodiments, methods of treating primary sclerosing cholangitis are provided, the methods comprising administering a therapeutic compound as provided herein to the subject to treat the primary sclerosing cholangitis.

In some embodiments, methods of treating Type 1 diabetes are provided, the methods comprising administering a therapeutic compound as provided herein to the subject to treat the Type 1 diabetes.

In some embodiments, methods of treating a transplant subject are provided, the methods comprising administering a therapeutically effective amount of a therapeutic compound as provided herein to the subject, thereby treating a transplant (recipient) subject.

In some embodiments, methods of treating GVHD in a subject having a transplanted a donor tissue are provided, the methods comprising administering a therapeutically effective amount of a therapeutic compound as provided herein to the subject.

In some embodiments, methods of treating a subject having, or at risk, or elevated risk, for having, an autoimmune disorder are provided, the methods comprising administering a therapeutically effective amount of a therapeutic compound as provided herein, thereby treating the subject.

BRIEF DESCRIPTION OF THE DRAWINGS

FIG. 1 depicts non-limiting embodiments of the therapeutic compounds provided herein.

FIG. 2 depicts a non-limiting illustration of how a therapeutic compound provided herein could function.

DETAILED DESCRIPTION

Figure 1:
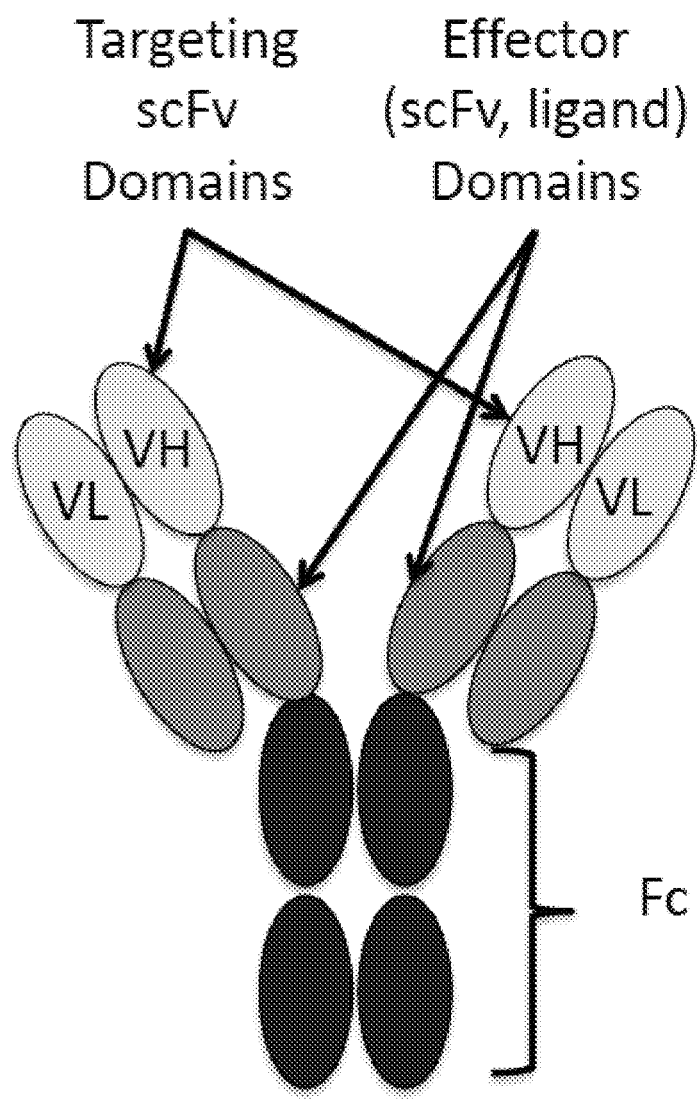
FIG. 1 is a depiction of a bi-specific therapeutic compound in a tandem scFv-Fc format (150 kDa) containing a targeting scFv domain and an effector domain consisting of either an scFv or a sequence corresponding to the endogenous ligand.
Figure 2:
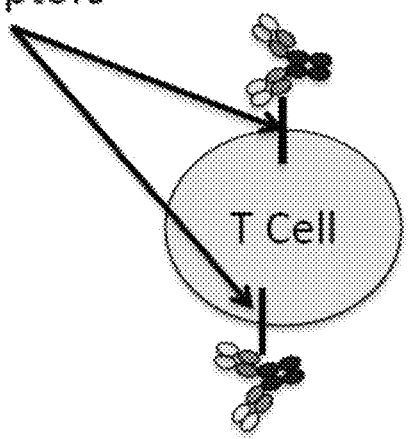
FIG. 2 is a depiction of a T cell bound to therapeutic compounds disclosed herein. In state 1 the effector domain of a bi-specific binds inhibitory receptors of T cells while in systemic circulation, with neither agonism or antagonism of the receptor occurring. In state 2, the targeting domain of bi-specific binds to target organ leading to bi-specific multimerization on the target organ surface. During T cell recognition of target organ, multimerized effector domains bind, cluster and signal through T cell inhibitory molecules.
Figure 2:
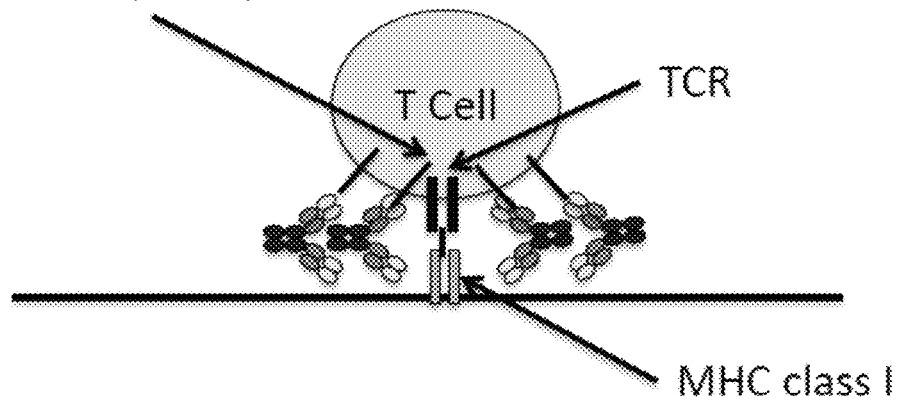

As used herein and unless otherwise indicated, the term "about" is intended to mean±5% of the value it modifies. Thus, about 100 means 95 to 105.

As used herein and in the appended claims, the singular forms "a", "an" and "the" include plural reference unless the context clearly dictates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "animal" includes, but is not limited to, humans and non-human vertebrates such as wild, domestic, and farm animals.

As used herein, the term "contacting" means bringing together of two elements in an in vitro system or an in vivo system. For example, "contacting" a therapeutic compound with an individual or patient or cell includes the administration of the compound to an individual or patient, such as a human, as well as, for example, introducing a compound into a sample containing a cellular or purified preparation containing target.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any composition or method that recites the term "comprising" should also be understood to also describe such compositions as consisting, consisting of, or consisting essentially of the recited components or elements.

As used herein, the term "individual," "subject," or "patient," used interchangeably, means any animal, including mammals, such as mice, rats, other rodents, rabbits, dogs, cats, swine, cattle, sheep, horses, or primates, such as humans.

As used herein, the term "inhibit" refers to a result, symptom, or activity being reduced as compared to the activity or result in the absence of the compound that is inhibiting the result, symptom, or activity. In some embodiments, the result, symptom, or activity, is inhibited by about, or, at least, 10%, 20%, 30%, 40%, 50%, 60%, 70%, 80%, 90%, 95%, or 99%. An result, symptom, or activity can also be inhibited if it is completely elimination or extinguished.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, or condition is prevalent.

As used herein, the phrase "integer from X to Y" means any integer that includes the endpoints. For example, the phrase "integer from X to Y" means 1, 2, 3, 4, or 5.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined. In some embodiments, the pharmaceutical compositions can be ophthalmically acceptable or suitable for ophthalmic administration.

"Specific binding" or "specifically binds to" or is "specific for" a particular antigen, target, or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen, target, or an epitope can be exhibited, for example, by an antibody having a $K_D$ for an antigen or epitope of at least about $10^{-4M}$, at least about $10^{-5M}$, at least about $10^{-6\ M}$, at least about $10^{-7M}$, at least about $10^{-8M}$, at least about $10^{-9M}$, alternatively at least about $10^{-10\ M}$, at least about $10^{-11M}$, at least about $10^{-12M}$, or greater, where $K_D$ refers to a dissociation rate of a particular antibody-target interaction. Typically, an antibody that specifically binds an antigen or target will have a $K_D$ that is, or at least, 2-, 4-, 5-, 10-, 20-, 50-, 100-, 500-, 1000-, 5,000-, 10,000-, or more times greater for a control molecule relative to the antigen or epitope.

In some embodiments, specific binding for a particular antigen, target, or an epitope can be exhibited, for example, by an antibody having a $K_A$ or $K_a$ for a target, antigen, or epitope of at least 2-, 4-, 5-, 20-, 50-, 100-, 500-, 1000-, 5,000-, 10,000- or more times greater for the target, antigen, or epitope relative to a control, where $K_A$ or $K_a$ refers to an association rate of a particular antibody-antigen interaction.

As provided herein, the therapeutic compounds and compositions can be used in methods of treatment as provided herein. As used herein, the terms "treat," "treated," or "treating" mean both therapeutic treatment and prophylactic measures wherein the object is to slow down (lessen) an undesired physiological condition, disorder or disease, or obtain beneficial or desired clinical results. For purposes of these embodiments, beneficial or desired clinical results include, but are not limited to, alleviation of symptoms; diminishment of extent of condition, disorder or disease;

stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of pain" or "treating pain" means an activity that alleviates or ameliorates any of the primary phenomena or secondary symptoms associated with the pain or other condition described herein.

Provided herein are therapeutic compounds, e.g., therapeutic protein molecules, e.g., fusion proteins, including a targeting moiety and an effector binding/modulating moiety, typically as separate domains. Also provided are methods of using and making the therapeutic compounds. The targeting moiety serves to localize the therapeutic compound, and thus the effector binding/modulating moiety, to a site at which immune-privilege is desired. The effector binding/modulating moiety comprises one or more of: (a) an immune cell inhibitory molecule binding/modulating moiety (an ICIM binding/modulating moiety): (b) an immunosuppressive immune cell binding/modulating moiety (an IIC binding/modulating moiety); or (c) a soluble molecule binding/modulating moiety (a SM binding/modulating moiety). In some embodiments, a therapeutic compound comprises: (a) and (b;) (a) and (c); (b) and (c); or (a), (b), and (c).

The present disclosure provides, for example, molecules that can act as PD-1 agonists. Without being bound to any particular theory, agonism of PD-1 inhibits T cell activation/signaling and can be accomplished by different mechanisms. For example cross-linking can lead to agonism, bead-bound, functional PD-1 agonists have been described (Akkaya. Ph.D. Thesis: Modulation of the PD-1 pathway by inhibitory antibody superagonists. Christ Church College, Oxford, UK, 2012), which is hereby incorporated by reference. Cross-linking of PD-1 with two mAbs that bind non-overlapping epitopes induces PD-1 signaling (Davis, US 2011/0171220), which is hereby incorporated by reference. Another example is illustrated through the use of a goat anti-PD-1 antiserum (e.g. AF1086, R&D Systems) which is hereby incorporated by reference, which acts as an agonist when soluble (Said et al., 2010, Nat Med) which is hereby incorporated by reference. Non-limiting examples of PD-1 agonists that can be used in the present embodiments include, but are not limited to, UCB clone 19 or clone 10, PD1AB-1, PD1AB-2, PD1AB-3, PD1AB-4 and PD1AB-5, PD1AB-6 (Anaptys/Celgene), PD1-17, PD1-28, PD1-33 and PD1-35 (Collins et al, US 2008/0311117 A1 Antibodies against PD-1 and uses therefor, which is incorporated by reference), or can be a bi-specific, monovalent anti-PD-1/anti-CD3 (Ono), and the like. In some embodiments, the PD-1 agonist antibodies can be antibodies that block binding of PD-L1 to PD-1. In some embodiments, the PD-1 agonist antibodies can be antibodies that do not block binding of PD-L1 to PD-1.

PD-1 agonism can be measured by any method, such as the methods described in the examples. For example, cells can be constructed that express, including stably express, constructs that include a human PD-1 polypeptide fused to a b-galactosidase "Enzyme donor" and 2) a SHP-2 polypeptide fused to a b-galactosidase "Enzyme acceptor." Without being bound by any theory, when PD-1 is engaged, SHP-2 is recruited to PD-1. The enzyme acceptor and enzyme donor form a fully active b-galactosidase enzyme that can be assayed. Although, the assay does not directly show PD-1 agonism, but shows activation of PD-1 signaling. PD-1 agonism can also be measured by measuring inhibition of T cell activation because, without being bound to any theory, PD-1 agonism inhibits anti-CD3-induced T cell activation. For example, PD-1 agonism can be measured by preactivating T cells with PHA (for human T cells) or ConA (for mouse T cells) so that they express PD-1. The cells can then be reactivated with anti-CD3 in the presence of anti-PD-1 (or PD-L1) for the PD-1 agonism assay. T cells that receive a PD-1 agonist signal in the presence of anti-CD3 will show decreased activation, relative to anti-CD3 stimulation alone. Activation can be readout by proliferation or cytokine production (IL-2, IFNg, IL-17) or other markers, such as CD69 activation marker. Thus, PD-1 agonism can be measured by either cytokine production or cell proliferation. Other methods can also be used to measure PD-1 agonism.

PD-1 is Ig superfamily member expressed on activated T cells and other immune cells. The natural ligands for PD-1 appear to be PD-L1 and PD-L2. Without being bound to any particular theory, when PD-L1 or PD-L2 bind to PD-1 on an activated T cell, an inhibitory signaling cascade is initiated, resulting in attenuation of the activated T effector cell function. Thus, blocking the interaction between PD-1 on a T cell, and PD-L1/2 on another cell (eg tumor cell) with a PD-1 antagonist is known as checkpoint inhibition, and releases the T cells from inhibition. In contrast, PD-1 agonist antibodies can bind to PD-1 and send an inhibitory signal and attenuate the function of a T cell. Thus, PD-1 agonist antibodies can be incorporated into various embodiments described herein as an effector molecule binding/modulating moiety, which can accomplish localized tissue-specific immunomodulation when paired with a targeting moiety.

The effector molecule binding/modulating moiety can provide an immunosuppressive signal or environment in a variety of ways. In some embodiments, the effector binding/modulating moiety comprises an ICIM binding/modulating moiety that directly binds and (under the appropriate conditions as described herein) activates an inhibitory receptor expressed by immune cells responsible for driving disease pathology. In another embodiment the effector binding/modulating moiety comprises and IIC binding/modulating moiety and binds and accumulates immunosuppressive immune cells. In some embodiments, the accumulated immune suppressive cells promote immune privilege. In another embodiment the effector binding/modulating moiety comprises an SM binding/modulating moiety which manipulates the surrounding microenvironment to make it less permissible for the function of immune cells, e.g., immune cells driving disease pathology. In some embodiments, the SM binding/modulating moiety depletes an entity that promotes immune attack or activation.

The targeting moiety and effector binding/modulating moiety are physically tethered, covalently or non-covalently, directly or through a linker entity, to one another, e.g., as a member of the same protein molecule in a therapeutic protein molecule. In some embodiments, the targeting and effector moieties are provided in a therapeutic protein molecule, e.g., a fusion protein, typically as separate domains. In some embodiments, the targeting moiety, the effector binding/modulating moiety, or both each comprises a single domain antibody molecule, e.g., a camelid antibody VHH molecule or human soluble VH domain. It may also contain a single-chain fragment variable (scFv) or a Fab domain. In some embodiments, the therapeutic protein molecule, or a nucleic acid, e.g., an mRNA or DNA, encoding the therapeutic protein molecule, can be administered to a subject. In some embodiments, the targeting and effector molecule binding/modulating moieties are linked to a third entity, e.g., a carrier, e.g., a polymeric carrier, a dendrimer, or a particle, e.g., a nanoparticle. The therapeutic compounds can be used to down regulate an immune response at or in a tissue at a selected target or site while having no or substantially less immunosuppressive function systemically. The target or site can comprise donor tissue or autologous tissue.

Provided herein are methods of providing site-specific immune privilege for a transplanted donor tissue, e.g., an allograft tissue, e.g., a tissue described herein, e.g., an allograft liver, an allograft kidney, an allograft heart, an allograft pancreas, an allograft thymus or thymic tissue, allograft skin, or an allograft lung, with therapeutic compounds disclosed herein. In embodiments the treatment minimizes rejection of, minimizes immune effector cell mediated damage to, prolongs acceptance of, or prolongs the functional life of, donor transplant tissue.

Also provided herein are methods of inhibiting graft versus host disease (GVHD) by minimizing the ability of donor immune cells, e.g., donor T cells, to mediate immune attack of recipient tissue, with therapeutic compounds disclosed herein.

Also provided herein are methods of treating, e.g., therapeutically treating or prophylactically treating (or preventing), an auto-immune disorder or response in a subject by administration of a therapeutic compound disclosed herein, e.g., to provide site or tissue specific modulation of the immune system. In some embodiments, the method provides tolerance to, minimization of the rejection of, minimization of immune effector cell mediated damage to, or prolonging a function of, subject tissue. In some embodiments, the therapeutic compound includes a targeting moiety that targets, e.g., specifically targets, the tissue under, or at risk for, autoimmune attack. Non-limiting exemplary tissues include, but are not limited to, the pancreas, myelin, salivary glands, synoviocytes, and myocytes.

As used herein, the terms "treat," "treated," or "treating" in regards to therapeutic treatment wherein the object is to slow down (lessen) an undesired physiological condition, disorder or disease, or obtain beneficial or desired clinical results. For example, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of an auto-immune disease/disorder" means an activity that alleviates or ameliorates any of the primary phenomena or secondary symptoms associated with the auto-immune disease/disorder or other condition described herein. The various disease or conditions are provided herein. The therapeutic treatment can also be administered prophylactically to preventing or reduce the disease or condition before the onset.

In some embodiments, administration of the therapeutic compound begins after the disorder is apparent. In some embodiments, administration of the therapeutic compound, begins prior to onset, or full onset, of the disorder. In some embodiments, administration of the therapeutic compound, begins prior to onset, or full onset, of the disorder, e.g., in a subject having the disorder, a high-risk subject, a subject having a biomarker for risk or presence of the disorder, a subject having a family history of the disorder, or other indicator of risk of, or asymptomatic presence of, the disorder. For example, In some embodiments, a subject having islet cell damage but which is not yet diabetic, is treated.

While not wishing to be bound by theory, it is believed that the targeting moiety functions to bind and accumulate the therapeutic to a target selectively expressed at the anatomical site where immune privilege is desired. In some embodiments, e.g., in the context of donor tissue transplantation, the target moiety binds to a target, e.g., an allelic product, present in the donor tissue but not the recipient. For treatment of autoimmune disorders, the targeting moiety binds a target preferentially expressed at the anatomical site where immune privilege is desired, e.g., in the pancreas. For treatment of GVHD, the targeting moiety targets the host tissue, and protects the host against attack from transplanted immune effector cells derived from transplanted tissue.

Again, while not wishing to be bound by theory it is believed that the effector binding/modulating moiety serves to deliver an immunosuppressive signal or otherwise create an immune privileged environment.

Unless otherwise defined, all technical and scientific terms used herein have the same meaning as commonly understood by one of ordinary skill in the art to which these embodiments belong. Although methods and materials similar or equivalent to those described herein can be used in the practice or testing of the present embodiments, suitable methods and materials are described below. All publications, patent applications, patents, and other references mentioned herein are incorporated by reference in their entirety. In addition, the materials, methods, and examples are illustrative only and not intended to be limiting. Headings, subheadings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the embodiments will be apparent from the description and drawings, and from the claims.

Additional Definitions

Unless defined otherwise, all technical and scientific terms used herein have the same meaning as commonly understood by one of ordinary skill in the art to which the embodiments pertains. In describing and claiming the present embodiments, the following terminology and terminology otherwise referenced throughout the present application will be used according to how it is defined, where a definition is provided.

It is also to be understood that the terminology used herein is for the purpose of describing particular embodiments only, and is not intended to be limiting.

Antibody molecule, as that term is used herein, refers to a polypeptide, e.g., an immunoglobulin chain or fragment thereof, comprising at least one functional immunoglobulin variable domain sequence. An antibody molecule encompasses antibodies (e.g., full-length antibodies) and antibody fragments. In some embodiments, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')2 fragments, and single chain variable fragments (scFvs).

The term "antibody molecule" also encompasses whole or antigen binding fragments of domain, or single domain, antibodies, which can also be referred to as "sdAb" or "VHH." Domain antibodies comprise either $V_H$ or $V_L$ that can act as stand-alone, antibody fragments. Additionally, domain antibodies include heavy-chain-only antibodies (HCAbs). Domain antibodies also include a CH2 domain of an IgG as the base scaffold into which CDR loops are grafted. It can also be generally defined as a polypeptide or protein comprising an amino acid sequence that is comprised of four framework regions interrupted by three complementarity determining regions. This is represented as FR1-CDR1-FR2-CDR2-FR3-CDR3-FR4. sdAbs can be produced in camelids such as llamas, but can also be synthetically generated using techniques that are well known in the art. The numbering of the amino acid residues of a sdAb or polypeptide is according to the general numbering for VH domains given by Kabat et al. ("Sequence of proteins of immunological interest," US Public Health Services, NIH Bethesda, Md., Publication No. 91, which is hereby incorporated by reference). According to this numbering, FR1 of a sdAb comprises the amino acid residues at positions 1-30, CDR1 of a sdAb comprises the amino acid residues at positions 31-36, FR2 of a sdAb comprises the amino acids at positions 36-49, CDR2 of a sdAb comprises the amino acid residues at positions 50-65, FR3 of a sdAb comprises the amino acid residues at positions 66-94, CDR3 of a sdAb comprises the amino acid residues at positions 95-102, and FR4 of a sdAb comprises the amino acid residues at positions 103-113. Domain antibodies are also described in WO2004041862 and WO2016065323, each of which is hereby incorporated by reference. The domain antibodies can be a targeting moiety as described herein.

Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, hexavalent), or with higher orders of specificity (e.g. tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide.

Examples of formats for multispecific therapeutic compounds, e.g., bispecific antibody molecules are shown in the following non-limiting examples. Although illustrated with antibody molecules, they can be used as platforms for therapeutic molecules that include other non-antibody moieties as specific binding or effector moieties. In some embodiments, these non-limiting examples are based upon either a symmetrical or asymmetrical Fc formats.

For example, the figures illustrate non-limiting and varied symmetric homodimer approach. In some embodiments, the dimerization interface centers around human IgG1 CH2-CH3 domains, which dimerize via a contact interface spanning both CH2/CH2 and CH3/CH3. The resulting bispecific antibodies shown have a total valence comprised of four binding units with two identical binding units at the N-terminus on each side of the dimer and two identical units at the C-terminus on each side of the dimer. In each case the binding units at the N-terminus of the homo-dimer are different from those at the C-terminus of the homo-dimer. Using this type of bivalency for both an inhibitory T cell receptor at either terminus of the molecule and bivalency for a tissue tethering antigen can be achieved at either end of the molecule.

Figure 3:
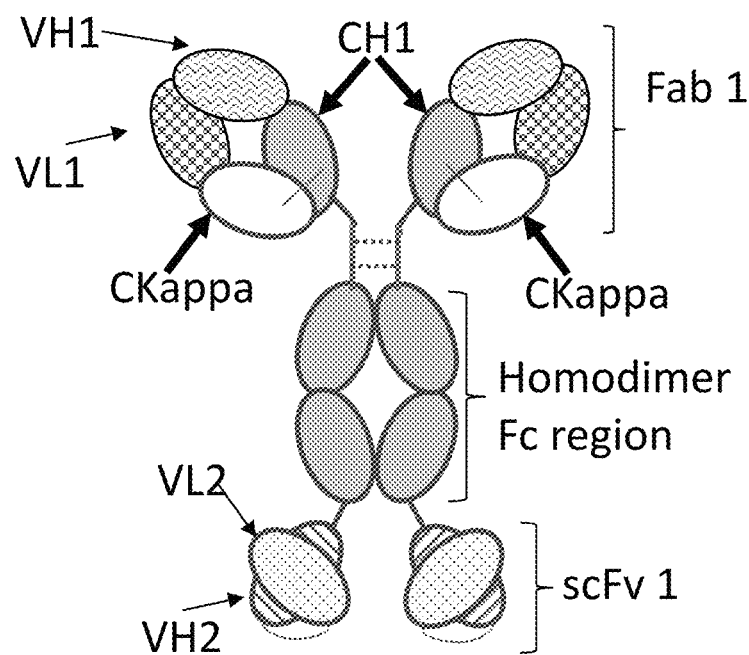
FIG. 3 depicts a non-limiting illustration of the therapeutic compounds provided herein.

For example, in FIG. 3, a non-limiting embodiment is illustrated. The N-terminus of the homodimer contains two identical Fab domains comprised of two identical light chains, which are separate polypeptides, interfaced with the n-terminal VH-CH1 domains of each heavy chain via the VH/VL interaction and Ckappa or Clambda interaction with CH1. The native disulphide bond between the Ckappa or Clambda with CH1 is present providing a covalent anchor between the light and heavy chains. At the c-terminus of this design are two identical scFv units where by (in this example) the c-terminus of the CH3 domain of the Fc, is followed by a flexible, hydrophilic linker typically comprised of (but not limited to) serine, glycine, alanine, and/or threonine residues, which is followed by the VH domain of each scFv unit, which is followed by a glycine/serine rich linker, followed by a VL domain. These tandem VH and VL domains associate to form a single chain fragment variable (scFv) appended at the c-terminus of the Fc. Two such units exist at the c-terminus of this molecule owing to the homodimeric nature centered at the Fc. The domain order of scFvs may be configured to be from N to C terminus either VH-Linker-VL or VL-Linker-VH.

Figure 3A:
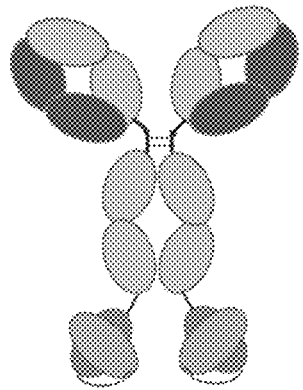
FIG. 3A depicts a non-limiting illustration of the therapeutic compounds provided herein.
Figure 3A:
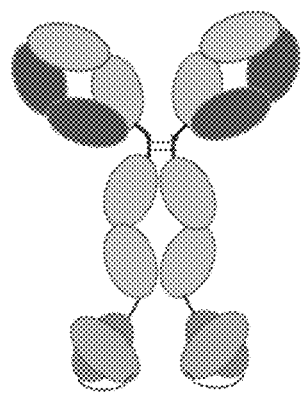

A non-limiting example of a molecule that has different binding regions on the different ends is where, one end is a PD-1 agonist and the antibody that provides target specificity is an anti-MAdCAM-1 antibody. This can be illustrated as shown, for example, in FIG. 3A, which illustrates the molecules in different orientations.

In some embodiments, the MAdCAM antibody is a blocking or non-blocking antibody as described elsewhere herein. Without being bound to any theory, MAdCAM has been shown to interact with the headpiece of the integrin α4β7 expressed on lymphocytes via multiple residues within its two Ig superfamily I-set domains and the atomic level structural basis for that interaction has been described (Viney J L et al. (1996). J Immunol. 157, 2488-2497; Yu Y et al (2013). J Biol Chem. 288, 6284-6294; Yu Y et al (2012). J Cell Biol. 196, 131-146, each of which is incorporated by reference in its entirety). It has been shown in great structural, mechanistic and functional detail in both the human (Chen J et al (2003). Nat Struct Biol. 10, 995-1001; de Chateau M et al (2001). Biochemistry. 40, 13972-13979) and mouse (Day E S et al (2002). Cell Commun Adhes. 9, 205-219; Hoshino H et al (2011). J Histochem Cytochem. 59, 572-583) molecular systems that any interaction of MAdCAM with α4β7 is dependent on three dication binding sites present in the integrin beta 7 sub unit I-like domain and that these metal binding sites can coordinate with Ca2+, Mn2+, and Mg2+. Using cell adhesion assays, flow cytometry, and/or flow chamber assays in the presence of high levels of Ca2+ with or without Mg2+ or Mn2+, the MAdCAM/α4β7 interaction is shown to be of a lower functional affinity and permits rolling adhesion of lymphocytes, whereas in low Ca2+ but higher Mg2+ or Mn2+ which activates the integrin, the MAdCAM/α4β7 interaction is of a higher functional affinity and mediates firm lymphocyte adhesion (Chen J et al (2003). Nat Struct Biol. 10, 995-1001). A number of groups have shown that various cell:cell, cell:membrane prep, and/or cell:protein based adhesion/interaction assays can be utilized, with FACS, cell flow chamber based counts, or IHC based read-outs to monitor the impact of anti-MAdCAM or anti-α4β7 antibodies upon the interaction of MAdCAM with α4β7, allowing one to identify blocking or non-blocking antibodies (Nakache, M et al (1989). Nature. 337, 179-181; Streeter, P R et al (1988). Nature. 331. 41-46; Yang Y et al (1995). Scand J Immunol. 42. 235-247; Leung E et al (2004). Immunol Cell Biol. 82. 400-409; Pullen N et al (2009). B J Pharmacol. 157. 281-293; Soler D et al (2009). J Pharmacol Exp Ther. 330. 864-875; Qi J et al (2012). J Biol Chem. 287. 15749-15759).

This has been exemplified in the mouse system setting with the identification of anti-mouse MAdCAM antibodies such as MECA-89 (non-blocking) and MECA-367 (blocking)) Nakache, M et al (1989). Nature. 337, 179-181; Streeter, P R et al (1988). Nature. 331. 41-46; Yang Y et al (1995). Scand J Immunol. 42. 235-247). In a human system, antibodies have been identified that block the interaction of human MAdCAM with human α4β7 such as anti-human MAdCAM PF-00547659 (Pullen N et al (2009). B J Pharmacol. 157. 281-293) and anti-human α4β7 vedolizumab (Soler D et al (2009). J Pharmacol Exp Ther. 330. 864-875), as well as antibodies that do not block the interaction such as anti-human MAdCAM clone 17F5 (Soler D et al (2009). J Pharmacol Exp Ther. 330. 864-875), and anti-human α4β7 clone J19 (Qi J et al (2012). J Biol Chem. 287. 15749-15759). Thus, the antibody can either be blocking or non-blocking based upon the desired effect. In some embodiments, the antibody is a non-blocking MAdCAM antibody. In some embodiments, the antibody is a blocking MAdCAM antibody. One non-limiting example of demonstrating whether an antibody is blocking or non-blocking can be found in Example 6, but any method can be used. Each of the references described herein are incorporated by reference in its entirety.

Figure 4:
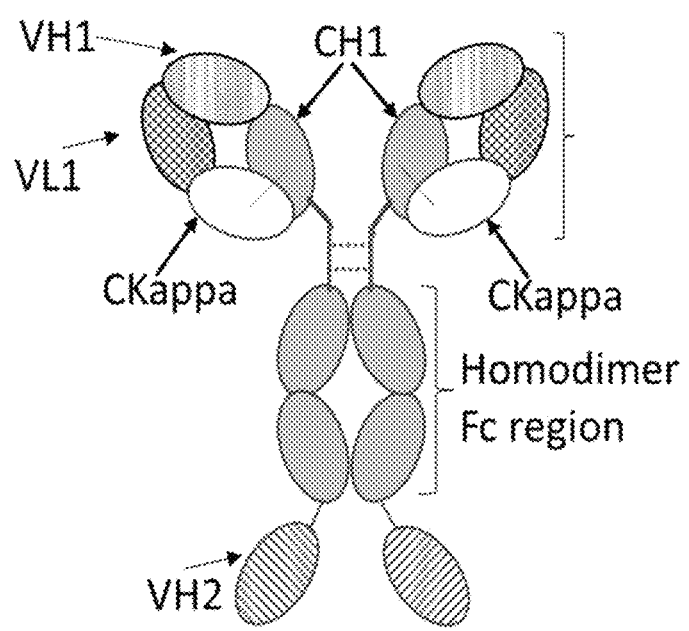
FIG. 4 depicts a non-limiting illustration of the therapeutic compounds provided herein.

In another example, and as depicted in FIG. 4, the N-terminus of the homodimer contains two identical Fab domains comprised of two identical light chains, which are separate polypeptides, interfaced with the n-terminal VH-CH1 domains of each heavy chain via the VH/VL interaction and Ckappa or Clambda interaction with CH1. The native disulphide bond between the Ckappa or Clambda with CH1 is present providing a covalent anchor between the light and heavy chains. At the c-terminus of this design are two identical VH units (though non-antibody moieties could also be substituted here or at any of the four terminal attachment/fusion points) where by (in this example) the c-terminus of the CH3 domain of the Fc, is followed by a flexible, hydrophilic linker typically comprised of (but not limited to) serine, glycine, alanine, and/or threonine residues, which is followed by a soluble independent VH3 germline family based VH domain. Two such units exist at the c-terminus of this molecule owing to the homodimeric nature centered at the Fc.

Figure 5:
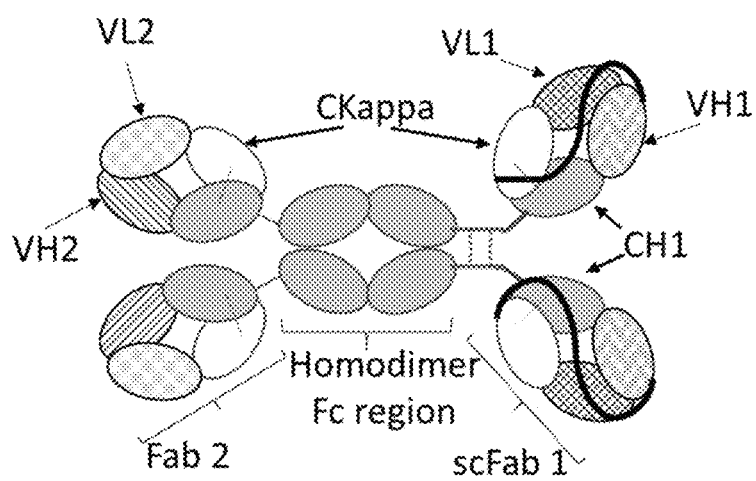
FIG. 5 depicts a non-limiting illustration of the therapeutic compounds provided herein.

In another non-limiting example, as depicted in FIG. 5, the N-terminus of the homodimer contains two identical Fab domains comprised of two identical light chains, which, unlike FIG. 3 and FIG. 4, are physically conjoined with the heavy chain at the N-terminus via a linker between the c-terminus of Ckappa or Clambda and the N-terminus of the VH. The linker may be 36-80 amino acids in length and comprised of serine, glycine, alanine and threonine residues. The physically conjoined n-terminal light chains interface with the n-terminal VH-CH1 domains of each heavy chain via the VH/VL interaction and Ckappa or Clambda interaction with CH1. The native disulphide bond between the Ckappa or Clambda with CH1 is present providing additional stability between the light and heavy chains. At the c-terminus of this design are two identical Fab units where by (in this example) the c-terminus of the CH3 domain of the Fc, is followed by a flexible, hydrophilic linker typically comprised of (but not limited to) serine, glycine, alanine, and/or threonine residues, which is followed by a CH1 domain, followed by a VH domain at the c-terminus. The light chain that is designed to pair with the c-terminal CH1/VH domains is expressed as a separate polypeptide, unlike the N-terminal light chain which is conjoined to the n-terminal VH/CH1 domains as described. The C-terminal light chains form an interface at between VH/VL and Ckappa or Clambda with CH1. The native disulphide anchors this light chain to the heavy chain. Again, any of the antibody moieties at any of the four attachment/fusion points can be substituted with a non-antibody moiety, e.g., a effector binding/modulating moiety that does not comprise an antibody molecule.

Figure 6:
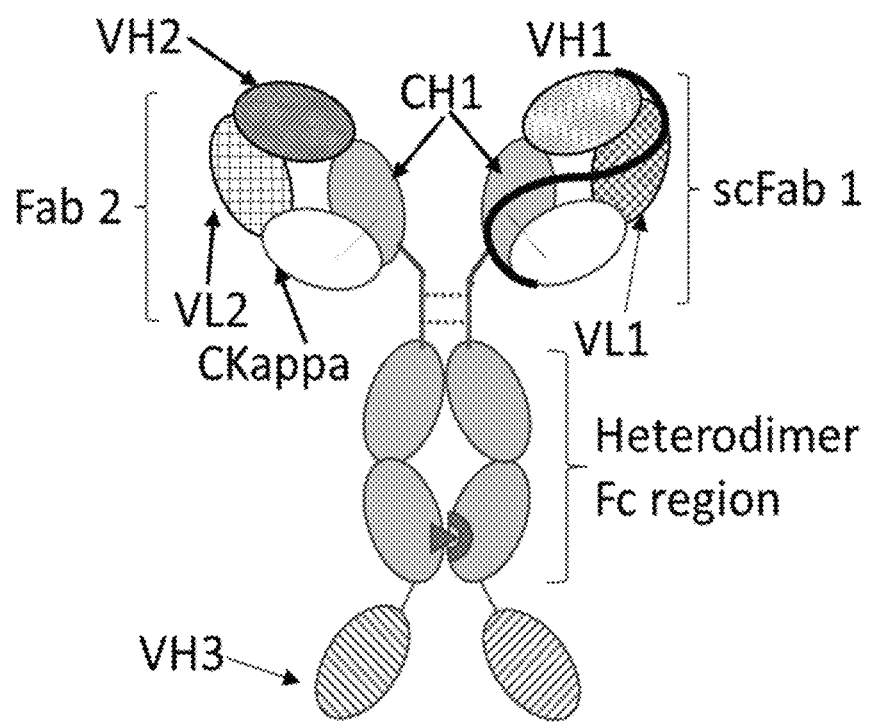
FIG. 6 depicts a non-limiting illustration of the therapeutic compounds provided herein.
Figure 7:
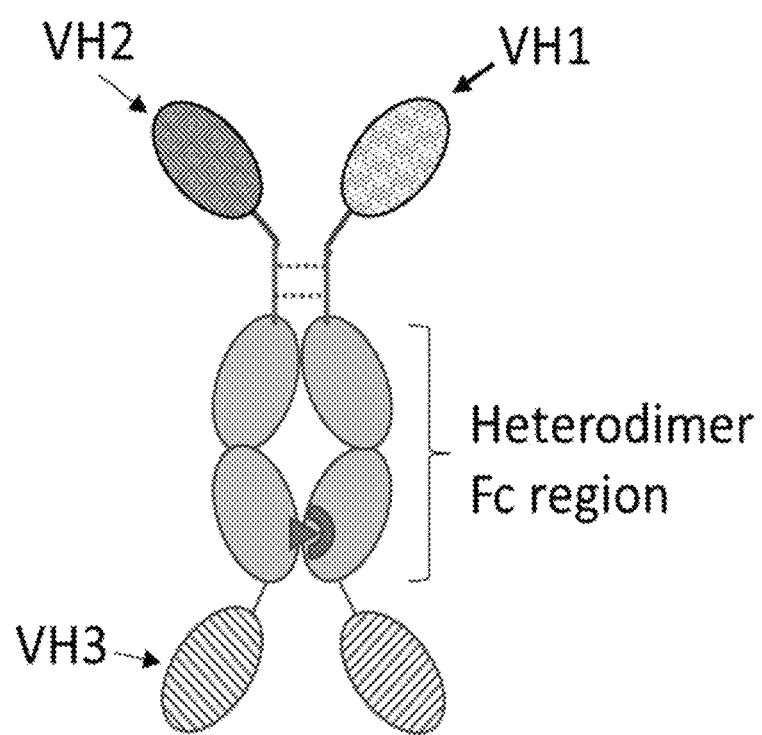
FIG. 7 depicts a non-limiting illustration of the therapeutic compounds provided herein.
Figure 8:
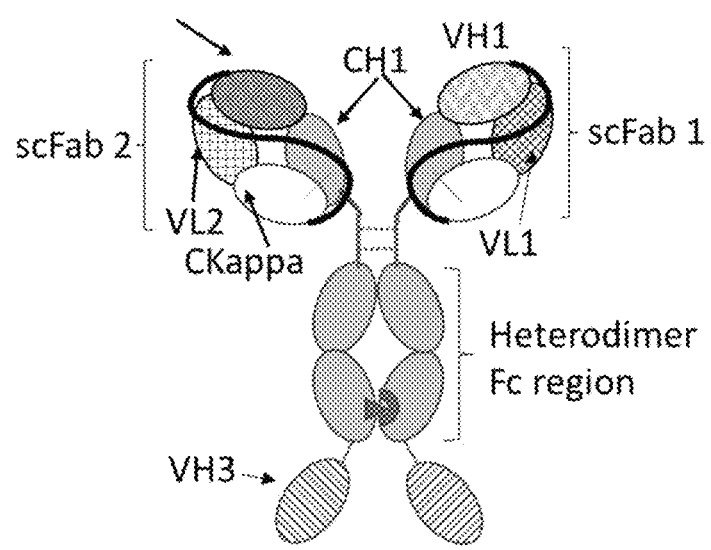
FIG. 8 depicts a non-limiting illustration of the therapeutic compounds provided herein.

The bispecific antibodies can also be asymmetric as shown in the following non-limiting examples. Non-limiting example are also depicted in FIG. 6, FIG. 7, and FIG. 8, which illustrate an asymmetric/heterodimer approach. Again, in any of these formats, any of the antibody moieties at any of the four attachment/fusion points can be substituted with a non-antibody moiety, e.g., a effector binding/modulating moiety that does not comprise an antibody molecule. In some embodiments, the dimerization interface centers around the human IgG1 CH2-CH3 domains, which dimerize via a contact interface spanning both CH2/CH2 and CH3/CH3. However, in order to achieve heterodimerization instead of homodimerization of each heavy chain, mutations are introduced in each CH3 domain. The heterodimerizing mutations include T366W mutation (kabat) in one CH3 domain and T366S, L368A, and Y407V (kabat) mutations in the other CH3 domain. The heterodimerizing interface may be further stabilized with de novo disulphide bonds via mutation of native residues to cysteine residues such as S354 and Y349 on opposite sides of the CH3/CH3 interface. The resulting bispecific antibodies shown have a total valence comprised of four binding units. With this approach, the overall molecule can be designed to have bispecificity at just one terminus and monospecificity at the other terminus (trispecificity overall) or bispecificity at either terminus with an overall molecular specificity of 2 or 4. In the illustrative examples below, the C-terminus comprises two identical binding domains which could, for example, provide bivalent monospecificity for a tissue tethering target. At the N-terminus of all three of the illustrative examples, both binding domains comprise different recognition elements/paratopes and which could achieve recognition of two different epitopes on the same effector moiety target, or could recognize for examples a T cell inhibitory receptor and CD3. In some embodiments, the N-terminal binding moieties may be interchanged with other single polypeptide formats such as scFv, single chain Fab, tandem scFv, VH or VHH domain antibody configurations for example. Other types of recognition element may be used also, such as linear or cyclic peptides.

An example of an asymmetric molecule is depicted in FIG. 6. Referring to FIG. 6, the N-terminus of the molecule is comprised of a first light chain paired with a first heavy chain via VH/VL and Ckappa or Clambda/CH1 interactions and a covalent tether comprised of the native heavy/light chain disulphide bond. On the opposite side of this heterodimeric molecule at the N-terminus is a second light chain and a second heavy chain which are physically conjoined via a linker between the c-terminus of Ckappa or Clambda and the N-terminus of the VH. The linker may be 36-80 amino acids in length and comprised of serine, glycine, alanine and threonine residues. The physically conjoined n-terminal light chains interface with the n-terminal VH-CH1 domains of each heavy chain via the VH/VL interaction and Ckappa or Clambda interaction with CH1. The native disulphide bond between the Ckappa or Clambda with CH1 is present providing additional stability between the light and heavy chains. At the c-terminus of the molecule are two identical soluble VH3 germline family VH domains joined via an N-terminal glycine/serine/alanine/threonine based linker to the c-terminus of the CH3 domain of both heavy chain 1 and heavy chain 2.

In some embodiments, an asymmetric molecule can be as illustrated as depicted in FIG. 7. For example, the N-terminus of the molecule is comprised of two different VH3 germlined based soluble VH domains linked to the human IgG1 hinge region via a glycine/serine/alanine/threonine based linker. The VH domain connected to the first heavy chain is different to the VH domain connected to the second heavy chain. At the c-terminus of each heavy chain is an additional soluble VH3 germline based VH domain, which is identical on each of the two heavy chains. The heavy chain heterodimerizes via the previously described knobs into holes mutations present at the CH3 interface of the Fc module.

In some embodiments, an asymmetric molecule can be as illustrated in FIG. 8. This example is similar to the molecule shown in FIG. 7, except both N-terminal Fab units are configured in a way that light chain 1 and light chain 2 are physically conjoined with heavy chain 1 and heavy chain 2 via a linker between the c-terminus of Ckappa or Clambda and the N-terminus of each respective VH. The linker in each case may be 36-80 amino acids in length and comprised of serine, glycine, alanine and threonine residues. The physically conjoined n-terminal light chains interface with the n-terminal VH-CH1 domains of each heavy chain via the VH/VL interaction and Ckappa or Clambda interaction with CH1. The native disulphide bond between the Ckappa or Clambda with CH1 is present providing additional stability between the light and heavy chains.

Bi-specific molecules can also have a mixed format. This is illustrated, for example, in FIG. 9, FIG. 10, and FIG. 11.

Figure 9:
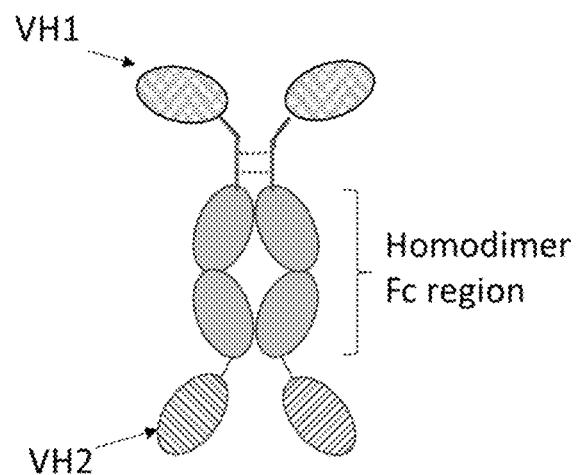
FIG. 9 depicts a non-limiting illustration of the therapeutic compounds provided herein.

For example, as illustrated in FIG. 9, illustrates a homodimer Fc based approach (see FIGS. 3, 4, and 5), combined with the moiety format selection of FIG. 7, whereby the total molecular valency is four, but specificity is restricted to two specificities. The N-terminus is comprised of two identical soluble VH3 germline based VH domains and the c-terminus is comprised of two identical soluble VH3 germlined based VH domains of different specificity to the N-terminal domains. Therefore, each specificity has a valence of two. Again, in this format, any of the antibody moieties at any of the four attachment/fusion points can be substituted with a non-antibody moiety, e.g., an effector binding/modulating moiety that does not comprise an antibody molecule.

Figure 10:
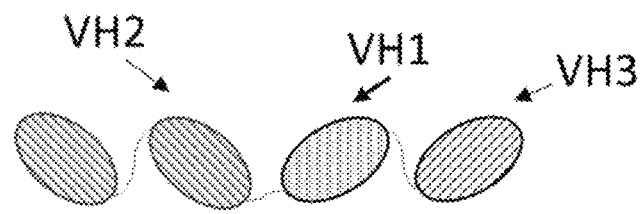
FIG. 10 depicts a non-limiting illustration of the therapeutic compounds provided herein.

FIG. 10 illustrates another example. In this example, the molecule is comprised of four VH3 germline based soluble VH domains. The first two domains have the same specificity (for example an inhibitory receptor), the 3rd domain from the N-terminus may have specificity for a tissue antigen and the fourth domain from the N-terminus may have specificity for human serum albumin (HSA), thereby granting the molecule extended half-life in the absence of an Ig Fc domain. Three glycine, serine, alanine and/or threonine rich linkers exists between domains 1 and 2, domains 2 and 3, and domains 3 and 4. This format may be configured with up to tetraspecificity, but monovalent in each case, or to have bispecificity with bivalency in each case. The order of domains can be changed. Again, in this format, any of the antibody moieties can be substituted with a non-antibody moiety, e.g., a effector binding/modulating moiety that does not comprise an antibody molecule.

Figure 11:
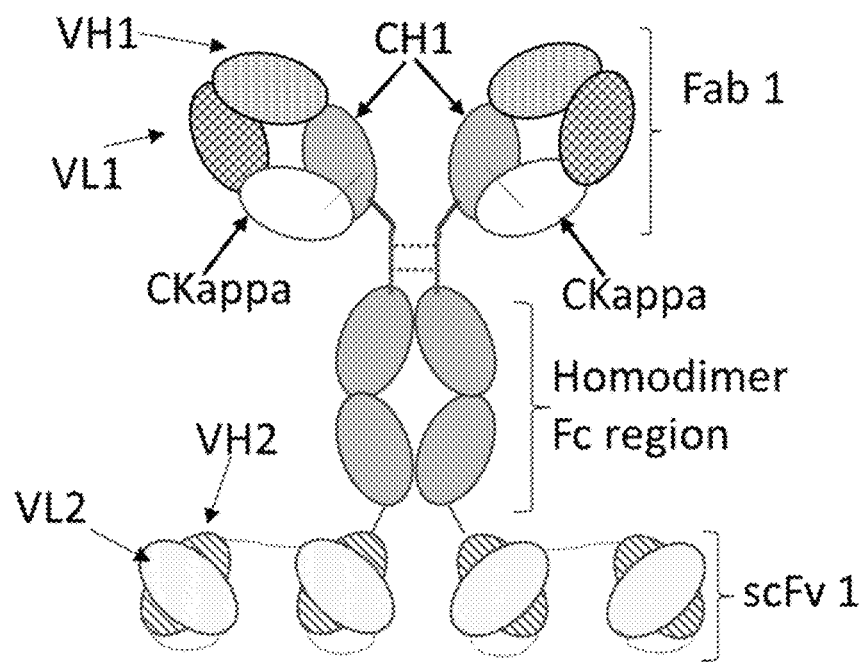
FIG. 11 depicts a non-limiting illustration of the therapeutic compounds provided herein.

FIG. 11 illustrates yet another approach. This example is similar to FIGS. 3 and 4, in that it is Fc homodimer based with two identical Fab units (bivalent monospecificity) at the N-terminus of the molecule. This example differs in that the C-terminus of each heavy chain is appended with a tandem-scFv. Thus, in each case the c-terminus of the CH3 domain of the Fc is linked via a glycine/serine/alanine/threonine based linker to the N-terminus of a first VH domain, which is linked via the C-terminus by a 12-15 amino acid glycine/serine rich linker to the N-terminus of a first VL domain, which linked via a 25-35 amino acid glycine/serine/alanine/threonine based linker at the c-terminus to the N-terminus of a second VH domain, which is linked via the c-terminus with a 12-15 amino acid glycine/serine based linker to the N-terminus of a 2nd VL domain. In this Fc homodimer based molecule there are therefore two identical tandem scFvs at the c-terminus of the molecule offering either tetravalency for a single tissue antigen for example or bivalency to two different molecules. This format could also be adapted with a heterodimer Fc core allowing two different tandem-scFvs at the c-terminus of the Fc allowing for monovalent tetraspecificity at the c-terminus while retaining either bivalent monospecificity at the N-terminus or monovalent bispecificity at the N-terminal via usage of single chain Fab configurations as in FIGS. 5, 6, and 7. This molecule can therefore be configured to have 2, 3, 4, 5, or 6 specificities. The domain order of scFvs within the tandem-scFv units may be configured to be from N to C terminus either VH-Linker-VL or VL-Linker-VH. Again, in this format, any of the antibody moieties at any of the four attachment/fusion points can be substituted with a non-antibody moiety, e.g., a effector binding/modulating moiety that does not comprise an antibody molecule.

Figure 12:
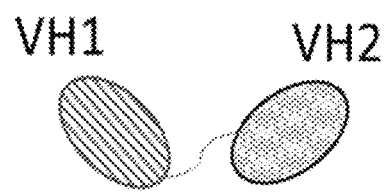
FIG. 12 depicts a non-limiting illustration of the therapeutic compounds provided herein.
Figure 13:
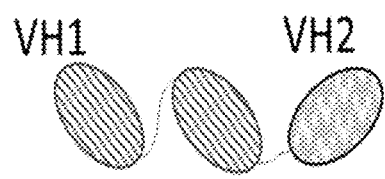
FIG. 13 depicts a non-limiting illustration of the therapeutic compounds provided herein.
Figure 14:
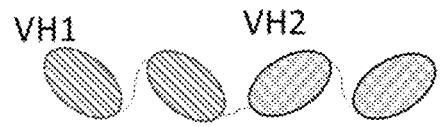
FIG. 14 depicts a non-limiting illustration of the therapeutic compounds provided herein.

Bi-specific antibodies can also be constructed to have, for example, shorter systemic PK while having increased tissue penetration. These types of antibodies can be based upon, for example, a human VH3 based domain antibody format. These are illustrated, for example, in FIGS. 12, 13, and 14. FIGS. 12, 13, and 14 each comprised a soluble VH3 germline family based VH domain modules. Each domain is approximately 12.5 kDa allowing for a small overall MW, which, without being bound to any particular theory, should be beneficial for enhanced tissue penetration. In these examples, none of the VH domains recognize any half-life extending targets such as FcRn or HSA. As illustrated in FIG. 12, the molecule is comprised of two VH domains joined with a flexible hydrophilic glycine/serine based linker between the C-terminus of the first domain and N-terminus of the second domain. In this example one domain may recognize a T cell co-stimulatory receptor and the second may recognize a tissue tethering antigen. As illustrated in FIG. 13, the molecule is comprised of three VH domains with N-C terminal linkages of hydrophilic glycine/serine based linkers. The molecule may be configured to be trispecific but monovalent for each target. It may be bispecific with bivalency for one target and monovalency for another. As illustrated in FIG. 14, the molecule is comprised of four VH domains with N-C terminal Glycine/Serine rich linkers between each domain. This molecule may be configured to be tetraspecific, trispecific, or bispecific with varying antigenic valencies in each case. Again, in this format, any of the antibody moieties at can be substituted with a non-antibody moiety, e.g., a effector binding/modulating moiety that does not comprise an antibody molecule.

Figure 15:
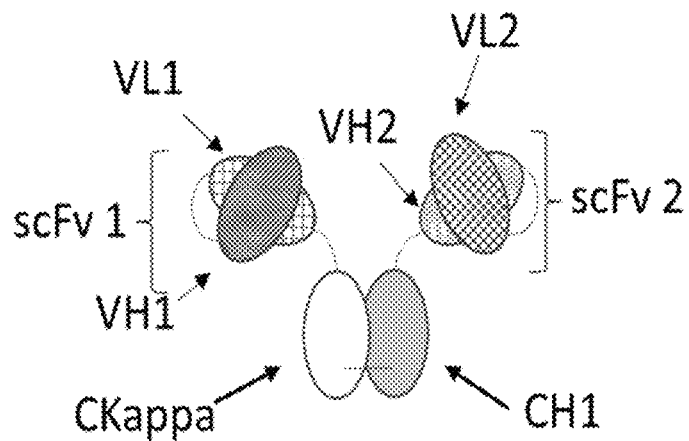
FIG. 15 depicts a non-limiting illustration of the therapeutic compounds provided herein.
Figure 16:
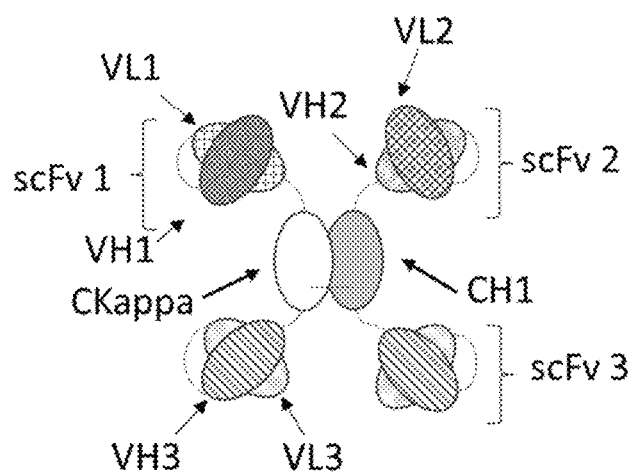
FIG. 16 depicts a non-limiting illustration of the therapeutic compounds provided herein.

Other embodiments of bi-specific antibodies are illustrated in FIGS. 15 and 16. FIGS. 15 and 16 are comprised of the naturally heterodimerizing core of the human IgG CH1/Ckappa interface, including the c-terminal heavy/light disulphide bond which covalently anchors the interaction. This format does not contain an Fc or any moieties for half life extension. As illustrated in FIG. 15, the molecule, at the N-terminus of the constant kappa domain is appended with an scFv fragment consisting of an N-terminal VH domain, linked at its C-terminus to the N-terminus of a VL domain via a 12-15 amino acid gly/ser based linker, which is linked by its C-terminus to the N-terminus of the constant kappa domain via the native VL-Ckappa elbow sequence. The CH1 domain is appended at the N-terminus with an scFv fragment consisting of an N-terminal VL domain linked at its c-terminus via a 12-15 amino acid gly/ser linker to the N-terminus of a VH domain, which is linked at its c-terminus to the N-terminus of the CH1 domains via the natural VH-CH1 elbow sequence. As illustrated in FIG. 16, the molecule has the same N-terminal configuration to Example 13. However the C-terminus of the constant kappa and CH1 domains are appended with scFv modules which may be in either the VH-VL or VL-VH configuration and may be either specific for the same antigen or specific for two different antigens. The VH/VL inter-domain linkers may be 12-15 amino acids in length and consisting of gly/ser residues. The scFv binding sub-units may be swapped for soluble VH domains, or peptide recognition elements, or even tandem-scFv elements. This approach can also be configured to use variable lambda and/or constant lambda domains. Again, in this format, any of the antibody moieties at any of the attachment/fusion points can be substituted with a non-antibody moiety, e.g., a effector binding/modulating moiety that does not comprise an antibody molecule.

Figure 17:
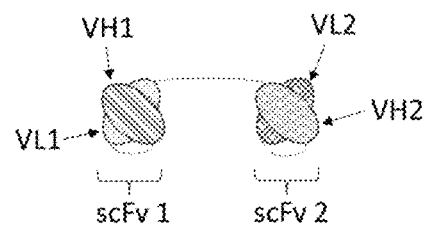
FIG. 17 depicts a non-limiting illustration of the therapeutic compounds provided herein.

FIG. 17 illustrates another embodiment. FIG. 17 represents a tandem scFv format consisting of a first N-terminal VL domain linked at its C-terminus to the N-terminus of a first VH domain with a 12-15 amino acid gly/ser rich linker, followed at the first VH c-terminus by a 25-30 amino acid gly/ser/ala/thr based linker to the N-terminus of a second VL domain. The second VL domain is linked at the C-terminus to the N-terminus of a 2nd VH domain by a 12-15 amino acid gly/ser linker. Each scFv recognizes a different target antigen such as a co-stimulatory T cell molecule and a tissue tethering target. Again, in this format, any of the antibody moieties can be substituted with a non-antibody moiety, e.g., a effector binding/modulating moiety that does not comprise an antibody molecule.

Figure 18:
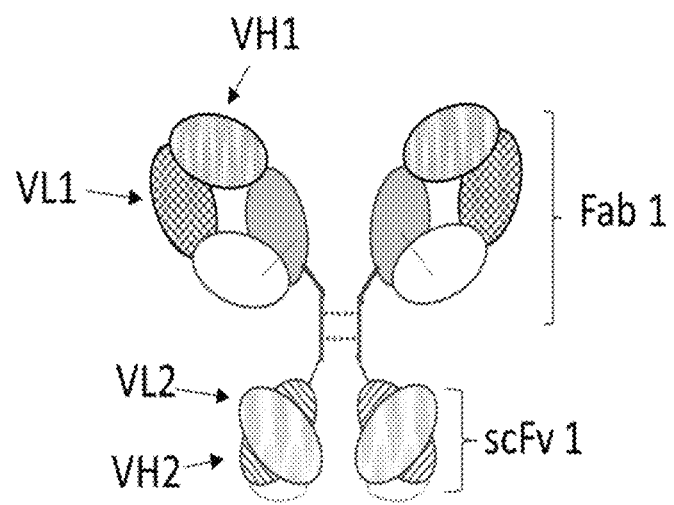
FIG. 18 depicts a non-limiting illustration of the therapeutic compounds provided herein.

FIG. 18 illustrates another embodiment. FIG. 18 is a F(ab')2 scFv fusion. This consists of two identical Fab components joined via two disulphide bonds in the native human IgG1 hinge region c-terminal of the human IgG CH1 domain. The human IgG1 CH2 and CH3 domains are absent. At the c-terminus of heavy chains 1 and 2 are two identical scFv fragments linked via a gly/ser/ala/thr rich linker to the c-terminus of the huIgG1 hinge region. In the configuration shown, the VH is N-terminal in each scFv unit and linked bia a 12-15 amino acid gly/ser rich linker to the N-terminus of a VL domain. An alternative configuration would be N-term-VL-Linker-VH-C-term. In this design, the construct is bispecific with bivalency for reach target. Again, in this format, any of the antibody moieties at any of the four attachment/fusion points can be substituted with a non-antibody moiety, e.g., a effector binding/modulating moiety that does not comprise an antibody molecule.

CD39 molecule, as that term as used herein, refers to a polypeptide having sufficient CD39 sequence that, as part of a therapeutic compound, it phosphohydrolyzes ATP to AMP. In some embodiments, a CD39 molecule phosphohydrolizes ATP to AMP equivalent to, or at least, 10, 20, 30, 40, 50, 60, 70, 80, 90, or 95% of the rate of a naturally occurring CD39, e.g., the CD39 from which the CD39 molecule was derived. In some embodiments, a CD39 molecule has at least 60, 70, 80, 90, 95, 99, or 100% sequence identity, or substantial sequence identity, with a naturally occurring CD39.

Any functional isoform can be used (with CD39 or other proteins discussed herein). Exemplary CD39 sequence include Genbank accession #NP_001767.3 or a mature form from the following sequence:

```
                                          (SEQ ID NO: 1)
MEDTKESNVKTFCSKNILAILGFSSIIAVIALLAVGLTQNKALPENVKYG

IVLDAGSSHTSLYIYKWPAEKENDTGVVHQVEECRVKGPGISKFVQKVNE

IGIYLTDCMERAREVIPRSQHQETPVYLGATAGMRLLRMESEELADRVLD

VVERSLSNYPFDFQGARIITGQEEGAYGWITINYLLGKFSQKTRWFSIVP

YETNNQETFGALDLGGASTQVTFVPQNQTIESPDNALQFRLYGKDYNVYT

HSFLCYGKDQALWQKLAKDIQVASNEILRDPCFHPGYKKVVNVSDLYKTP

CTKRFEMTLPFQQFEIQGIGNYQQCHQSILELFNTSYCPYSQCAFNGIFL

PPLQGDFGAFSAFYFVMKFLNLTSEKVSQEKVTEMMKKFCAQPWEEIKTS

YAGVKEKYLSEYCFSGTYILSLLLQGYHFTADSWEHIHFIGKIQGSDAGW

TLGYMLNLTNMIPAEQPLSTPLSHSTYVFLMVLFSLVLFTVAIIGLLIFH

KPSYFWKDMV.
```

In some embodiments, a CD39 molecule comprises a soluble catalytically active form of CD39 found to circulate in human or murine serum, see, e.g., Metabolism of circulating ADP in the bloodstream is mediated via integrated actions of soluble adenylate kinase-1 and NTPDase1/CD39 activities, Yegutkin et al. FASEB J. 2012 September; 26(9): 3875-83. A soluble recombinant CD39 fragment is also described in Inhibition of platelet function by recombinant soluble ecto-ADPase/CD39, Gayle, et al., J Clin Invest. 1998 May 1; 101(9): 1851-1859.

CD73 molecule, as that term as used herein, refers to a polypeptide having sufficient CD73 sequence that, as part of a therapeutic compound, it dephosphorylates extracellular AMP to adenosine. In some embodiments, a CD73 molecule dephosphorylates extracellular AMP to adenosine equivalent to, or at least, 10, 20, 30, 40, 50, 60, 70, 80, 90, or 95% of the rate of a naturally occurring CD73, e.g., the CD73 from which the CD73 molecule was derived. In some embodiments, a CD73 molecule has at least 60, 70, 80, 90, 95, 99, or 100% sequence identity, or substantial sequence identity, with a naturally occurring CD73. Exemplary CD73 sequences include GenBank AAH65937.1 5'-nucleotidase, ecto (CD73) [*Homo sapiens*] or a mature form from the following sequence, (SEQ ID NO: 2)
MCPRAARAPATLLLALGAVLWPAAGAWELTILHTNDVHSRLEQTSEDSSK

CVNASRCMGGVARLFTKVQQIRRAEPNVLLLDAGDQYQGTIWFTVYKGAE

VAHFMNALRYDAMALGNHEFDNGVEGLIEPLLKEAKFPILSANIKAKGPL

ASQISGLYLPYKVLPVGDEVVGIVGYTSKETPFLSNPGTNLVFEDEITAL

QPEVDKLKTLNVNKIIALGHSGFEMDKLIAQKVRGVDVVVGGHSNTFLYT

GNPPSKEVPAGKYPFIVTSDDGRKVPVVQAYAFGKYLGYLKIEFDERGNV

ISSHGNPILLNSSIPEDPSIKADINKWRIKLDNYSTQELGKTIVYLDGSS

QSCRFRECNMGNLICDAMINNNLRHADETFWNHVSMCILNGGGIRSPIDE

RNNGTITWENLAAVLPFGGTFDLVQLKGSTLKKAFEHSVHRYGQSTGEFL

QVGGIHVVYDLSRKPGDRVVKLDVLCTKCRVPSYDPLKMDEVYKVILPNF

LANGGDGFQMIKDELLRHDSGDQDINVVSTYISKMKVIYPAVEGRIKFST

GSHCHGSFSLIFLSLWAVIFVLYQ.

In some embodiments, a CD73 molecule comprises a soluble form of CD73 which can be shed from the membrane of endothelial cells by proteolytic cleavage or hydrolysis of the GPI anchor by shear stress see, e.g., Reference: Yegutkin G, Bodin P, Burnstock G. Effect of shear stress on the release of soluble ecto-enzymes ATPase and 5'-nucleotidase along with endogenous ATP from vascular endothelial cells. Br J Pharmacol 2000; 129: 921-6. For CD73 function see Colgan et al., Physiological roles for ecto-5'-nucleotidase (CD73), Purinergic Signalling, June 2006, 2:351.

Cell surface molecule binder, as that term is used herein, refers to a molecule, typically a polypeptide, that binds, e.g., specifically, to a cell surface molecule on a cell, e.g., an immunosuppressive immune cell, e.g., a Treg. In some embodiments, the cell surface binder has sufficient sequence from a naturally occurring ligand of the cell surface molecule, that it can specifically bind the cell surface molecule (a cell surface molecule ligand). In some embodiments, the cell surface binding is an antibody molecule that binds, e.g., specifically binds, the cell surface molecule.

Donor specific targeting moiety, as that term is used herein, refers to a moiety, e.g., an antibody molecule, that as a component of a therapeutic compound, localizes the therapeutic compound preferentially to an implanted donor tissue, e.g., an organ, as opposed to tissue of a recipient. As a component of a therapeutic compound, the donor specific targeting moiety provides site-specific immune privilege for a transplant tissue, e.g., an organ, from a donor.

In some embodiments, a donor specific targeting moiety it binds to the product, e.g., a polypeptide product, of an allele present at a locus, which allele is not present at the locus in the (recipient) subject. In some embodiments, a donor specific targeting moiety binds to an epitope on product, which epitope is not present in the (recipient) subject.

In some embodiments, a donor specific targeting moiety, as a component of a therapeutic compound, preferentially binds to a donor target or antigen, e.g., has a binding affinity for the donor target that is greater for donor antigen or tissue, e.g., at least 2, 4, 5, 10, 50, 100, 500, 1,000, 5,000, or 10,000 fold greater, than its affinity for than for subject antigen or tissue. In some embodiments, a donor specific targeting moiety, has a binding affinity for a product of an allele of a locus present in donor tissue (but not present in the subject) at least 2, 4, 5, 10, 50, 100, 500, 1,000, 5,000, or 10,000 fold greater, than its affinity for the product of the allele of the locus present in the subject (which allele is not present in donor tissue). Affinity of a therapeutic compound of which the donor specific moiety is a component, can be measured in a cell suspension, e.g., the affinity for suspended cells having the allele is compared with its affinity for suspended cells not having the allele. In some embodiments, the binding affinity for the donor allele cells is below 10 nM. In some embodiments, the binding affinity for the donor allele cells is below 100 pM, 50 pM, or 10 pM.

In some embodiments, the specificity for a product of a donor allele is sufficient that when the donor specific targeting moiety is coupled to an immune-down regulating effector: i) immune attack of the implanted tissue, e.g., as measured by histological inflammatory response, infiltrating T effector cells, or organ function, in the clinical setting— e.g. creatinine for the kidney, is substantially reduced, e.g., as compared to what would be seen in an otherwise similar implant but lacking the donor specific targeting moiety is coupled to an immune-down regulating effector; and/or ii) immune function in the recipient, outside or away from the implanted tissue, is substantially maintained. In some embodiments, one or more of the following is seen: at therapeutic levels of therapeutic compound, peripheral blood lymphocyte counts are not substantially impacted, e.g., the level of T cells is within 25, 50, 75, 85, 90, or 95% of normal, the level of B cells is within 25, 50, 75, 85, 90, or 95% of normal, and/or the level of granuloctyes (PMNs) cells is within 25, 50, 75, 85, 90, or 95% of normal, or the level of monocytes is within 25, 50, 75, 85, 90, or 95% of normal; at therapeutic levels of therapeutic compound, the ex vivo proliferative function of PBMCs (peripheral blood mononuclear cells) against non-disease relevant antigens is substantially normal or is within 70, 80, or 90% of normal; at therapeutic levels of therapeutic compound, the incidence or risk of risk of opportunistic infections and cancers associated with immunosuppression is not substantially increased over normal; or at therapeutic levels of therapeutic compound, the incidence or risk of risk of opportunistic infections and cancers associated with immunosuppression is substantially less than would be seen with standard of care, or non-targeted, immunosuppression. In some embodiments, the donor specific targeting moiety comprises an antibody molecule, a target specific binding polypeptide, or a target ligand binding molecule.

Effector, as that term is used herein, refers to an entity, e.g., a cell or molecule, e.g., a soluble or cell surface molecule, which mediates an immune response.

Effector ligand binding molecule, as used herein, refers to a polypeptide that has sufficient sequence from a naturally occurring counter-ligand of an effector, that it can bind the effector with sufficient specificity that it can serve as an effector binding/modulating molecule. In some embodiments, it binds to effector with at least 10, 20, 30, 40, 50, 60, 70, 80, 90, or 95% of the affinity of the naturally occurring counter-ligand. In some embodiments, it has at least 60, 70, 80, 90, 95, 99, or 100% sequence identity, or substantial sequence identity, with a naturally occurring counter-ligand for the effector.

Effector specific binding polypeptide, as used herein, refers to a polypeptide that can bind with sufficient specificity that it can serve as an effector binding/modulating moiety. In some embodiments, a specific binding polypeptide comprises a effector ligand binding molecule.

Elevated risk, as used herein, refers to the risk of a disorder in a subject, wherein the subject has one or more of a medical history of the disorder or a symptom of the disorder, a biomarker associated with the disorder or a symptom of the disorder, or a family history of the disorder or a symptom of the disorder.

Functional antibody molecule to an effector or inhibitory immune checkpoint molecule, as that term is used herein, refers to an antibody molecule that when present as the ICIM binding/modulating moiety of a multimerized therapeutic compound, can bind and agonize the effector or inhibitory immune checkpoint molecule. In some embodiments, the anti-effector or inhibitory immune checkpoint molecule antibody molecule, when binding as a monomer (or binding when the therapeutic compound is not multimerized), to the effector or inhibitory immune checkpoint molecule, does not antagonize, substantially antagonize, prevent binding, or prevent substantial binding, of an endogenous counter ligand of the inhibitory immune checkpoint molecule molecule to inhibitory immune checkpoint molecule. In some embodiments, the anti-effector or inhibitory immune checkpoint molecule antibody molecule when binding as a monomer (or binding when the therapeutic compound is not multimerized), to the inhibitory immune checkpoint molecule, does not agonize or substantially agonize, the effector or inhibitory molecule.

ICIM binding/modulating moiety, as that term is used herein, refers to an effector binding/modulating moiety that, as part of a therapeutic compound, binds and agonizes a cell surface inhibitory molecule, e.g., an inhibitory immune checkpoint molecule, e.g., PD-1, or binds or modulates cell signaling, e.g., binds a FCRL, e.g., FCRL1-6, or binds and antagonizes a molecule that promotes immune function.

IIC binding/modulating moiety, as that term is used herein, refers to an effector binding/modulating moiety that, as part of a therapeutic compound, binds an immunosuppressive immune cell. In some embodiments, the IIC binding/modulating moiety increases the number or concentration of an immunosuppressive immune cell at the binding site.

An "inhibitory immune checkpoint molecule ligand molecule," as that term is used herein, refers to a polypeptide having sufficient inhibitory immune checkpoint molecule ligand sequence, e.g., in the case of a PD-L1 molecule, sufficient PD-L1 sequence, that when present as an ICIM binding/modulating moiety of a multimerized therapeutic compound, can bind and agonize its cognate inhibitory immune checkpoint molecule, e.g., again in the case of a PD-L1 molecule, PD-1.

In some embodiments, the inhibitory immune checkpoint molecule ligand molecule, e.g., a PD-L1 molecule, when binding as a monomer (or binding when the therapeutic compound is not multimerized), to its cognate ligand, e.g., PD-1, does not antagonize or substantially antagonize, or prevent binding, or prevent substantial binding, of an endogenous inhibitory immune checkpoint molecule ligand to the inhibitory immune checkpoint molecule. E.g., in the case of a PD-L1 molecule, the PD-L1 molecule does not antagonize binding of endogenous PD-L1 to PD-1.

In some embodiments, the inhibitory immune checkpoint molecule ligand when binding as a monomer, to its cognate inhibitory immune checkpoint molecule does not agonize or substantially agonize the inhibitory immune checkpoint molecule. By way of example, e.g., a PD-L1 molecule when binding to PD-1, does not agonize or substantially agonize PD-1.

In some embodiments, an inhibitory immune checkpoint molecule ligand molecule has at least 60, 70, 80, 90, 95, 99, or 100% sequence identity, or substantial sequence identity, with a naturally occurring inhibitory immune checkpoint molecule ligand.

Exemplary inhibitory immune checkpoint molecule ligand molecules include: a PD-L1 molecule, which binds to inhibitory immune checkpoint molecule PD-1, and in embodiments has at least 60, 70, 80, 90, 95, 99, or 100% sequence identity, or substantial sequence identity, with a naturally occurring PD-L1, e.g., the PD-L1 molecule comprising the sequence of MRIFAVFIFMTYWHLLNAF-TVTVPKDLYVVEYGSNMTIECKFPVEKQLDLAAL-IVYWE MEDKNIIQFVH-GEEDLKVQHSSYRQRARLLKDQLSLG-NAALQITDVKLQDAGVYRCMI SSYGGA-DYKRITVKVNAPYNKINQRILVVDPVTSEHELTCQAE-GYPKAEVIWTSSDHQVL SGKTTTTNSKREEKLFNVTSTLRINTTTNEIFYC-TFRRLDPEENHTAELVIPELPLAHPPNE RTHLVIL-GAILLCLGVALTFI-FRLRKGRMMDVKKCGIQDTNSKKQSDTHLEET (SEQ ID NO: 3), or an active fragment thereof; in some embodiments, the active fragment comprises residues 19 to 290 of the PD-L1 sequence; a HLA-G molecule, which binds to any of inhibitory immune checkpoint molecules KIR2DL4, LILRB1, and LILRB2, and in embodiments has at least 60, 70, 80, 90, 95, 99, or 100% sequence identity, or substantial sequence identity, with a naturally occurring HLA-G. Exemplary HLA-G sequences include, e.g., a mature form found in the sequence at GenBank P17693.1 RecName: Full=HLA class I histocompatibility antigen, alpha chain G; AltName: Full=HLA G antigen; AltName: Full=MHC class I antigen G; Flags: Precursor, or in the sequence (SEQ ID NO: 4)
MVVMAPRTLFLLLSGALTLTETWAGSHSMRYFSAAVSRPGRGEPRFIAMG

YVDDTQFVRFDSDSACPRMEPRAPWVEQEGPEYWEEETRNTKAHAQTDRM

NLQTLRGYYNQSEASSHTLQWMIGCDLGSDGRLLRGYEQYAYDGKDYLAL

NEDLRSWTAADTAAQISKRKCEAANVAEQRRAYLEGTCVEWLHRYLENGK

EMLQRADPPKTHVTHHPVEDYEATLRCWALGFYPAEIILTWQRDGEDQTQ

DVELVETRPAGDGTFQKWAAVVVPSGEEQRYTCHVQHEGLPEPLMLRWKQ

SSLPTIPEVIGIVA.

Inhibitory molecule counter ligand molecule, as that term is used herein, refers to a polypeptide having sufficient inhibitory molecule counter ligand sequence such that when present as the ICIM binding/modulating moiety of a multimerized therapeutic compound, can bind and agonize a cognate inhibitory molecule. In some embodiments, the inhibitory molecule counter ligand molecule, when binding as a monomer (or binding when the therapeutic compound is not multimerized), to the inhibitory molecule, does not antagonize, substantially antagonize, prevent binding, or prevent substantial binding, of an endogenous counter ligand of the inhibitory molecule to the inhibitory molecule. In some embodiments, the inhibitory molecule counter ligand molecule when binding as a monomer (or binding when the therapeutic compound is not multimerized), to the inhibitory molecule, does not agonize or substantially agonize, the inhibitory molecule.

Sequence identity, percentage identity, and related terms, as those terms are used herein, refer to the relatedness of two sequences, e.g., two nucleic acid sequences or two amino acid or polypeptide sequences. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) J. Mol. Biol. 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215: 403-10. BLAST nucleotide searches can be performed with the NBLAST program, score=100, wordlength=12 to obtain nucleotide sequences homologous to for example any a nucleic acid sequence provided herein. BLAST protein searches can be performed with the XBLAST program, score=50, wordlength=3 to obtain amino acid sequences homologous to protein molecules provided herein. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules and compounds of the present embodiments may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). CD39 molecule, a CD73 molecule, a Cell surface molecule binder, Donor specific targeting moiety Effector ligand binding molecule, ICIM binding/modulating moiety IIC binding/modulating moiety, an inhibitory immune checkpoint molecule ligand molecule, Inhibitory molecule counter ligand molecule, SM binding/modulating moiety, SM binding/modulating moiety, as that term is used herein, refers to an effector binding/modulating moiety that, as part of a therapeutic compound, promotes an immunosuppressive local microenvironment, e.g., by providing in the proximity of the target, a substance that inhibits or minimizes attack by the immune system of the target. In some embodiments, the SM binding/modulating moiety comprises, or binds, a molecule that inhibits or minimizes attack by the immune system of the target. In some embodiments, a therapeutic compound comprises an SM binding/modulating moiety that binds and accumulates a soluble substance, e.g., an endogenous or exogenous substance, having immunosuppressive function. In some embodiments, a therapeutic compound comprises an SM binding/modulating moiety that binds and inhibits, sequesters, degrades or otherwise neutralizes a substance, e.g., a soluble substance, typically and endogenous soluble substance, that promotes immune attack. In some embodiments, a therapeutic compound comprises an SM binding/modulating moiety that comprises an immune-suppressive substance, e.g. a fragment of protein known to be immunosuppressive. By way of example, an effector molecule binding moiety that binds, or comprises, a substance e.g., a CD39 molecule or a CD73 molecule, that depletes a component, that promotes immune effector cell function, e.g., ATP or AMP.

Specific targeting moiety, as that term is used herein, refers to donor specific targeting moiety or a tissue specific targeting moiety.

Subject, as that term is used herein, refers to a mammalian subject, e.g., a human subject. In some embodiments, the subject is a non-human mammal, e.g., a horse, dog, cat, cow, goat, or pig.

Target ligand binding molecule, as used herein, refers to a polypeptide that has sufficient sequence from a naturally occurring counter-ligand of a target ligand that it can bind the target ligand on a target tissue (e.g., donor tissue or subject target tissue) with sufficient specificity that it can serve as a specific targeting moiety. In some embodiments, it binds to target tissue or cells with at least 10, 20, 30, 40, 50, 60, 70, 80, 90, or 95% of the affinity of the naturally occurring counter-ligand. In some embodiments, it has at least 60, 70, 80, 90, 95, 99, or 100% sequence identity, or substantial sequence identity, with a naturally occurring counter-ligand for the target ligand.

Target site, as that term is used herein, refers to a site which contains the entity, e.g., epitope, bound by a targeting moiety. In some embodiments, the target site is the site at which immune privilege is established.

Tissue specific targeting moiety, as that term is used herein, refers to a moiety, e.g., an antibody molecule, that as a component of a therapeutic molecule, localizes the therapeutic molecule preferentially to a target tissue, as opposed to other tissue of a subject. As a component of a therapeutic compound, the tissue specific targeting moiety provides site-specific immune privilege for a target tissue, e.g., an organ or tissue undergoing or at risk for autoimmune attack. In some embodiments, a tissue specific targeting moiety binds to a product, e.g., a polypeptide product, which is not present outside the target tissue, or is present at sufficiently low levels that, at therapeutic concentrations of therapeutic molecule, unacceptable levels of immune suppression are absent or substantially absent. In some embodiments, a tissue specific targeting moiety binds to an epitope, which epitope is not present outside, or not substantially present outside, the target site.

In some embodiments, a tissue specific targeting moiety, as a component of a therapeutic compound, preferentially binds to a target tissue or target tissue antigen, e.g., has a binding affinity for the target tissue or antigen that is greater for target antigen or tissue, e.g., at least 2, 4, 5, 10, 50, 100, 500, 1,000, 5,000, or 10,000 fold greater, than its affinity for than for non-target tissue or antigen present outside the target tissue. Affinity of a therapeutic compound of which the tissue specific moiety is a component, can be measured in a cell suspension, e.g., the affinity for suspended cells having the target antigen is compared with its affinity for suspended cells not having the target antigen. In some embodiments, the binding affinity for the target antigen bearing cells is below 10 nM.

In some embodiments, the binding affinity for the target antigen bearing cells is below 100 pM, 50 pM, or 10 pM. In some embodiments, the specificity for a target antigen is sufficient, that when the tissue specific targeting moiety is coupled to an immune-down regulating effector: i) immune attack of the target tissue, e.g., as measured by histological inflammatory response, infiltrating T effector cells, or organ function, in the clinical setting—e.g. creatinine for kidney, is substantially reduced, e.g., as compared to what would be seen in an otherwise similar implant but lacking the tissue specific targeting moiety is coupled to an immune-down regulating effector; and/or ii) immune function in the recipient, outside or away from the target tissue, is substantially maintained.

In some embodiments, one or more of the following is seen: at therapeutic levels of therapeutic compound, peripheral blood lymphocyte counts are not substantially impacted, e.g., the level of T cells is within 25, 50, 75, 85, 90, or 95% of normal, the level of B cells is within 25, 50, 75, 85, 90, or 95% of normal, and/or the level of granulocytes (PMNs) cells is within 25, 50, 75, 85, 90, or 95% of normal, or the level of monocytes is within 25, 50, 75, 85, 90, or 95% of normal 1; at therapeutic levels of therapeutic compound, the ex vivo proliferative function of PBMCs (peripheral blood mononuclear cells) against non-disease relevant antigens is substantially normal or is within 70, 80, or 90% of normal; at therapeutic levels of therapeutic compound, the incidence or risk of risk of opportunistic infections and cancers associated with immunosuppression is not substantially increased over normal; or at therapeutic levels of therapeutic compound, the incidence or risk of risk of opportunistic infections and cancers associated with immunosuppression is substantially less than would be seen with standard of care, or non-targeted, immunosuppression. In some embodiments, the tissue specific targeting moiety comprises an antibody molecule. In some embodiments, the donor specific targeting moiety comprises an antibody molecule, a target specific binding polypeptide, or a target ligand binding molecule. In some embodiments, the tissue specific targeting moiety binds a product, or a site on a product, that is present or expressed exclusively, or substantially exclusively, on target tissue.

ICIM Binding/Modulating Moieties: Effector Binding/Modulating Moieties that Bind Inhibitory Receptors Methods and compounds described herein provide for a therapeutic compound having an effector binding/modulating moiety comprising an ICIM binding/modulating moiety, that directly binds and activates an inhibitory receptor on the surface of an immune cell, e.g., to reduce or eliminate, or substantially eliminate, the ability of the immune cell to mediate immune attack. Coupling of the ICIM binding/modulating moiety to a targeting entity, promotes site-specific or local down regulation of the immune cell response, e.g., confined substantially to the locations having binding sites for the targeting moiety. Thus, normal systemic immune function is substantially retained. In some embodiments, an ICIM binding/modulating moiety comprises an inhibitory immune checkpoint molecule counter ligand molecule, e.g., a natural ligand, or fragment of a natural ligand (e.g., PD-L1 or HLA-G) of the inhibitory immune checkpoint molecule. In some embodiments, an ICIM binding/modulating moiety comprises a functional antibody molecule, e.g., a functional antibody molecule comprising an scFv binding domain, that engages inhibitory immune checkpoint molecule.

In some embodiments, the ICIM binding/modulating moiety, comprising, e.g., a functional antibody molecule, or inhibitory immune checkpoint molecule ligand molecule, binds the inhibitory receptor but does not prevent binding of a natural ligand of the inhibitory receptor to the inhibitory receptor. In embodiments a format is used wherein a targeting moiety is coupled, e.g., fused, to an ICIM binding/modulating moiety, comprising, e.g., an scFv domain, and configured so that upon binding of an inhibitory receptor while in solution (e.g., in blood or lymph) (and presumably in a monomeric format), the therapeutic molecule: i) fails to agonize, or fails to substantially agonize (e.g., agonizes at less than 30, 20, 15, 10, or 5% of the level seen with a full agonizing molecule) the inhibitory receptor on the immune cell; and/or ii) fails to antagonize, or fails to substantially antagonize (e.g., antagonizes at less than 30, 20, 15, 10, or 5% of the level seen with a full antagonizing molecule) the inhibitory receptor on the immune cell. A candidate molecule can be evaluated for its ability to agonize or not agonize by its ability to either increase or decrease the immune response in an in vitro cell based assay wherein the target is not expressed, e.g., using an MLR-based assay (mixed lymphocyte reaction).

In some embodiments, candidate ICIM binding/modulating moieties can reduce, completely or substantially eliminate systemic immunosuppression and systemic immune activation. In some embodiments, the targeting domain of the therapeutic compound, when bound to target, will serve to cluster or multimerize the therapeutic compound on the surface of the tissue desiring immune protection. In some embodiments, the ICIM binding/modulating moiety, e.g., an ICIM binding/modulating moiety comprising a scFv domain, requires a clustered or multimeric state to be able to deliver an agonistic and immunosuppressive signal, or substantial levels of such signal, to local immune cells. This type of therapeutic can, for example, provide to a local immune suppression whilst leaving the systemic immune system unperturbed or substantially unperterbed. That is, the immune suppression is localized to where the suppression is needed as opposed to being systemic and not localized to a particular area or tissue type.

In some embodiments, upon binding to the target e.g., a target organ, tissue or cell type, the therapeutic compound coats the target, e.g., target organ, tissue or cell type. When circulating lymphocytes attempt to engage and destroy the target, this therapeutic will provide an 'off' signal only at, or to a greater extent at, the site of therapeutic compound accumulation.

A candidate therapeutic compound can be evaluated for the ability to bind, e.g., specifically bind, its target, e.g., by ELISA, a cell based assay, or surface plasmon resonance. by. This property should generally be maximized, as it mediates the site-specificity and local nature of the immune privilege. A candidate therapeutic compound can be evaluated for the ability to down regulate an immune cell when bound to target, e.g., by a cell based activity assay. This property should generally be maximized, as it mediates the site-specificity and local nature of the immune privilege. The level of down regulation effected by a candidate therapeutic compound in monomeric (or non-bound) form can be evaluated, e.g., by, e.g., by a cell based activity assay. This property should generally be minimized, as could mediate systemic down regulation of the immune system. The level of antagonism of a cell surface inhibitory molecule, e.g., an inhibitory immune checkpoint molecule, effected by a candidate therapeutic compound in monomeric (or non-bound) form can be evaluated, e.g., by, e.g., by a cell based activity assay. This property should generally be minimized, as could mediate systemic unwanted activation of the immune system. Generally, the properties should be selected and balanced to produce a sufficiently robust site specific immune privilege without unacceptable levels of non-site specific agonism or antagonism of the inhibitory immune checkpoint molecule.

Exemplary Inhibitory Immune Checkpoint Molecules

Exemplary inhibitory molecules (e.g., an inhibitory immune checkpoint molecule) (together with their counter ligands) can be found in Table 1. This table lists molecules to which exemplary ICIM binding moieties can bind.

TABLE 1

Cell surface inhibitory molecules, e.g., inhibitory
immune checkpoint molecules (column A), counter ligands
(column B) and cell types affected (column C).

| A | B | C |
|---|---|---|
| PD-1 Alkaline phosphatase | PD-L1, PD-L2 | T cells, B cells |
| B7-H3 | Unknown | T cells |
| B7-H4 | Neuropilin 1, neuropilin 2, Plexin4A | T cells |
| BTLA | HVEM | T cells, B cells |
| CTLA-4 | CD80, CD86 | T cells |
| IDO1 | Tryptophan | Lymphocytes |
| TDO2 | Tryptophan | Lymphocytes |
| KIR2DL1, KIR2DL2/3, KIR3DL1, KIR3DL2 | HLA MHC class I | NK cells |
| LAG3 | HLA MHC class II | T cells |
| TIM-3 | Galectin-9 | T cells |
| VISTA | Unknown | T cells, myeloid cells |
| TIGIT | CD155 | T cells |
| KIR2DL4 | HLA-G | NK cells |
| LILRB1 | HLA-G | T cells, NK cells, B cells, monocytes, dendritic cells |
| LILRB2 | HLA-G | Monocytes, dendritic cells, neutrophils, some tumor cells |
| NKG2A | nonclassical MHC glycoproteins class I | T cells, NK cells |
| FCRL1-6 | FCRL1 - 2 not known FCRL4 = IgA FCRL5 = IgG FCRL6 = MHC Class II | B cells |
|  | BUTYROPHILINS, for example BTN1A1, BTN2A2, BTNL2, BTNL1, BTNL8 | Modulation of immune cells |

The PD-L1/PD-1 Pathway

Programmed cell death protein 1, (often referred to as PD-1) is a cell surface receptor that belongs to the immunoglobulin superfamily. PD-1 is expressed on T cells and other cell types including, but not limited to, B cells, myeloid cells, dendritic cells, monocytes, T regulatory cells, iNK T cells. PD-1 binds two ligands, PD-L1 and PD-L2, and is an inhibitory immune checkpoint molecule. Engagement with a cognate ligand, PD-L1 or PD-L2, in the context of engagement of antigen loaded MCH with the T Cell Receptor on a T cell minimizes or prevents the activation and function of T cells. The inhibitory effect of PD-1 can include both promoting apoptosis (programmed cell death) in antigen specific T-cells in lymph nodes and reducing apoptosis in regulatory T cells (suppressor T cells).

In some embodiments, a therapeutic compound comprises an ICIM binding/modulating moiety which agonizes PD-1 inhibition. An ICIM binding/modulating moiety can include an inhibitory molecule counter ligand molecule, e.g., comprising a fragment of a ligand of PD-1 (e.g., a fragment of PD-L1 or PD-L2) or another moiety, e.g., a functional antibody molecule, comprising, e.g., an scFv domain that binds PD-1.

In some embodiments, a therapeutic compound comprises a targeting moiety that is preferentially binds a donor antigen not present in, present in substantially lower levels in the subject, e.g., a donor antigen from Table 2, and is localized to donor graft tissue in a subject. In some embodiments, it does not bind, or does not substantially bind, other tissues. In some embodiments, a therapeutic compound can include a targeting moiety that is specific for HLA-A2 and specifically binds donor allograft tissue but does not bind, or does not substantially bind, host tissues. In some embodiments, the therapeutic compound comprises an ICIM binding/modulating moiety, e.g., an inhibitory molecule counter ligand molecule, e.g., comprising a fragment of a ligand of PD-1 (e.g., a fragment of PD-L1 or PD-L2) or another moiety, e.g., a functional antibody molecule, comprising, e.g., an scFv domain that binds PD-1, such that the therapeutic compound, e.g., when bound to target, activates PD-1. The therapeutic compound targets an allograft and provides local immune privilege to the allograft.

In some embodiments, a therapeutic compound comprises a targeting moiety that is preferentially binds to an antigen of Table 3, and is localized to the target in a subject, e.g., a subject having an autoimmune disorder, e.g., an autoimmune disorder of Table 3. In some embodiments, it does not bind, or does not substantially bind, other tissues. In some embodiments, the therapeutic compound comprises an ICIM binding/modulating moiety, e.g., an inhibitory molecule counter ligand molecule, e.g., comprising a fragment of a ligand of PD-1 (e.g., a fragment of PD-L1 or PD-L2) or another moiety, e.g., a functional antibody molecule, comprising, e.g., an scFv domain that binds PD-1, such that the therapeutic compound, e.g., when bound to target, activates PD-1. The therapeutic compound targets a tissue subject to autoimmune attack and provides local immune privilege to the tissue.

PD-L1 and PDL2, or polypeptides derived therefrom, can provide candidate ICIM binding moieties. However, in monomer form, e.g., when the therapeutic compound is circulating in blood or lymph, this molecule could have an undesired effect of antagonizing the PD-L1/PD-1 pathway, and may only agonize the PD-1 pathway when clustered or multimerized on the surface of a target, e.g., a target organ. In some embodiments, a therapeutic compound comprises an ICIM binding/modulating moiety comprising a functional antibody molecule, e.g., a scFv domain, that is inert, or substantially inert, to the PD-1 pathway in a soluble form but which agonizes and drives an inhibitory signal when multimerized (by the targeting moiety) on the surface of a tissue.

The HLA-G: KIR2DL4/LILRB1/LILRB2 Pathway

KIR2DL4, LILRB1, and LILRB2 are inhibitory molecules found on T cells, NK cells, and myeloid cells. HLA-G is a counter ligand for each.

KIR2DL4 is also known as CD158D, G9P, KIR-103AS, KIR103, KIR103AS, KIR, KIR-2DL4, killer cell immunoglobulin like receptor, and two Ig domains and long cytoplasmic tail 4.

LILRB1 is also known as LILRB1, CD85J, ILT-2, ILT2, LIR-1, LIR1, MIR-7, MIR7, PIR-B, PIRB, leukocyte immunoglobulin like receptor B1. LILRB2 is also known as CD85D, ILT-4, LIR-2, LIR2, MIR-10, MIR10, and ILT4.

A therapeutic compound comprising an HLA-G molecule can be used to provide inhibitory signals to an immune cell comprising any of KIR2DL4, LILRB1, and LILRB2, e.g., with multimerized therapeutic compound molecules comprising an HLA-G molecule and thus provide site-specific immune privilege.

A therapeutic compound comprising an agonistic anti-KIR2DL4, anti-LILRB1, or anti-LILRB2 antibody molecule can be used to provide inhibitory signals to an immune cell comprising any of KIR2DL4, LILRB1, and LILRB2.

HLA-G only delivers an inhibitory signal when multimerized, for example, when expressed on the surface of a cell or when conjugated to the surface of a bead. In embodiments, a therapeutic compound comprising an HLA-G molecule which therapeutic compound does not multimerize in solution (or does not multimerize sufficiently to result in significant levels of inhibitory molecule agonization), is provided. The use of HLA-G molecules that minimize mulitmerization in solution will minimize systemic agonization of immune cells and unwanted immune suppression.

While not wishing to be bound by theory it is believed that HLA-G is not effective in down regulation unless multimerized, that binding of the therapeutic compound to target, through the targeting moiety, multimerizes the ICIM binding entity, and that the multimerized ICIM binding entity, binds and clusters inhibitory molecules on the surface of an immune cell, thus mediating a negative signal that down regulates the immune cell. Thus, infiltrating immune cells attempting to damage the target tissue, including antigen presenting cells and other myeloid cells, NK cells and T cells, are down regulated.

While HLA-G molecules minimize antagonism when in monomeric form are desirable, the redundancy of LILRB1 and LILRB2 will minimize, the impact on systemic even with some monomeric antagonism.

In some embodiments, the therapeutic compound comprises an ICIM binding/modulating moiety that comprises a HLA-G molecule, e.g., an B2M-free isoform (e.g., HLA-G5), see Carosella et al., Advances in Immunology, 2015, 127:33. In a B2M-free format, HLA-G preferentially binds LILRB2.

Suitable sequences for the construction of HLA-G molecules include GenBank P17693.1 RecName: Full=HLA class I histocompatibility antigen, alpha chain G; AltName: Full=HLA G antigen; AltName: Full=MHC class I antigen G; Flags: Precursor, or MVVMAPRTLFLLLSGALTLTETWAGSHSMRYFSAAVSRPGRGEPRFIAMGYVDDTQFVRFDSDSACPRMEPRAPWVEQEGPEYWEEETRNTKAHAQTDRMNLQTLRGYYNQSEAS SHTLQWMIGCDLGSDGRLLRGYEQYAYDGKDYLALNEDLRSWTAADTAAQISKRKCE AANVAEQRRAYLEGTCVEWLHRYLENGKEMLQRADPPKTHVTHHPVFDYEATLRCW ALGFYPAEIILTWQRDGEDQTQDVELVETRPAGDGTFQKWAAVVVPSGEEQRYTCHVQ HEGLPEPLMLRWKQSSLPTIPIMGIVAGLVVLAAVVTGAAVAAVLWRKKSSD (SEQ ID NO: 5). A candidate HLA-G molecule can be tested for suitability for use in methods and compounds, e.g., by methods analogous to those described in "Synthetic HLA-G proteins for therapeutic use in transplantation," LeMaoult et al., 2013 The FASEB Journal 27:3643.

In some embodiments, a therapeutic compound comprises a targeting moiety that is preferentially binds a donor antigen not present in, present in substantially lower levels in the subject, e.g., a donor antigen from Table 2, and is localized to donor graft tissue in a subject. In some embodiments, it does not bind, or does not substantially bind, other tissues. In some embodiments, a therapeutic compound can include a targeting moiety that is specific for HLA-A2 and specifically binds a donor allograft but does not bind host tissues and is combined with an ICIM binding/modulating moiety that comprises a HLA-G molecule that binds KIR2DL4, LILRB1, or LILRB2, such that the therapeutic compound, e.g., when bound to target, activates KIR2DL4, LILRB1, or LILRB2. The therapeutic compound targets an allograft and provides local immune privilege to the allograft.

In some embodiments, a therapeutic compound comprises a targeting moiety that is preferentially binds a tissue specific antigen, e.g., an antigen from Table 3, and is localized to the target site in a subject, e.g., a subject having an autoimmune disorder, e.g., an anutoimmune disorder from Table 3. In some embodiments, it does not bind, or does not substantially bind, other tissues. In embodiments the therapeutic compound comprises an ICIM binding/modulating moiety that comprises a HLA-G molecule binds KIR2DL4, LILRB1, or LILRB2, such that the therapeutic compound, e.g., when bound to target, activates KIR2DL4, LILRB1, or LILRB2. The therapeutic compound targets an tissue subject to autoimmune attack and provides local immune privilege to the tissue.

It is likely possible to engineer a stable and soluble HLA-G-B2M fusion protein that can also bind LILRB1. For example, the crystal structure of HLA-G was determined using HLA-G/B2M monomers (Clements et al. 2005 PNAS 102:3360)

FCRL Family

FCRL1-6 generally inhibit B cell activation or function. These type 1 transmembrane glycoproteins are composed of different combinations of 5 types of immunoglobulin-like domains, with each protein consisting of 3 to 9 domains, and no individual domain type conserved throughout all of the FCRL proteins. In general, FCRL expression is restricted to lymphocytes, with the primary expression in B-lymphocytes. Generally, FCRLs function to repress B-cell activation.

An ICIM binding/modulating moiety can comprise an agonistic anti-BCMA antibody molecule. In some embodiments, the therapeutic compound comprises an anti-FCRL antibody molecule and an anti-B cell receptor (BCR) antibody molecule. While not wishing to be bound be theory is believed that a therapeutic compound comprising anti-body molecules of both specificities will bring the FCRL into close proximity with the BCR and inhibit BCR signaling.

Butyrophilins and Butyrophilin-Like Molecules

Effector binding/modulating moiety can comprise an agonist or antagonist of a butyrophilin. In some embodiments, an effector binding/modulating moiety an agonistic or functional BTN1A1 molecule, BTN2A2 molecule, BTNL2 molecule, or BTNL1 molecule.

A functional BTNXi molecule (where Xi=1A1, 2A2, L2 or L1), as that term as used herein, refers to a polypeptide having sufficient BTNXi sequence that, as part of a therapeutic compound, it inhibits T cells. In some embodiments, a BTNXi molecule has at least 60, 70, 80, 90, 95, 99, or 100% sequence identity, or substantial sequence identity, with a naturally occurring butyrophilin or butyrophilin-like molecule.

In some embodiments, an effector binding/modulating moiety an antagonistic BTNL8 molecule.

An antagonistic BTNL8 molecule, as that term as used herein, refers to a polypeptide having sufficient BTNL8 sequence that, as part of a therapeutic compound, it inhibits the activation, proliferation, or secretion of cytokine by a resting T cell. In some embodiments, a BTNL8 molecule has at least 60, 70, 80, 90, 95, 99, or 100% sequence identity, or substantial sequence identity, with a naturally occurring butyrophilin.

IIC Binding/Modulating Moieties: Effector Binding/Modulating Moieties that Recruit Immunosuppressive T Cells In some embodiments, a therapeutic compound comprises an effector binding/modulating moiety, e.g., an IIC binding/modulating moiety, that binds, activates, or retains immunosuppressive cells, e.g., immunosuppressive T cells, at the site mediated by the targeting moiety, providing site-specific immune privilege. The IIC binding/modulating moiety, e.g., an IIC binding/modulating moiety comprising an antibody molecule, comprising, e.g., an scFv binding domain, binds immunosuppressive cell types, e.g., Tregs, e.g., Foxp3+ CD25+ Tregs. Organ, tissue or specific cell type tolerance is associated with an overwhelming increase of Tregs proximal and infiltrating the target organ; in embodiments, the methods and compounds described herein synthetically re-create and mimic this physiological state. Upon accumulation of Tregs, an immunosuppressive microenvironment is created that serves to protect the organ of interest from the immune system.

GARP-Binders as a Treg and TGFB Targeting Molecule

GARP is a membrane protein receptor for latent TGF-beta expressed on the surface of activated Tregs (Tran et al. 2009 PNAS 106:13445 and Wang et al. 2009 PNAS 106:13439). In some embodiments, a therapeutic compound comprises an IIC binding entity that binds one or both of soluble GARP and GARP-expressing cells, such as activated human Tregs, and a targeting moiety that targets the therapeutic compound to the target tissue of interest. IIC binding/modulating moieties that comprises a GARP-Binder include, e.g., an IIC binding/modulating moiety that comprises an anti-GARP antibody molecule, e.g., an anti-GARP scFv domain. While not wishing to be bound by theory, it is believed that the therapeutic compound that comprises a GARP binder effects accumulation of GARP-expressing Tregs at the site targeted by the targeting moiety of the therapeutic compound, e.g., a transplant or site of organ injury. Again, while not wishing to be bound by theory, it is believed that a therapeutic compound that comprises a GARP binder effects can also effect accumulation of soluble GARP at site of organ injury, which will serve to bind and activate TGFB 1, an immunosuppressive cytokine, in a local manner (Fridrich et al. 2016 PLoS One 11:e0153290; doi: 10.1371/journal.pone.0153290 and Hahn et al. 2013 Blood 15:1182). Thus, an effector binding/modulating moiety that comprises a GARP binder can act as either a IIC binding/modulating moiety or an SM binding/modulating moiety.

CTLA4 as a Treg Targeting and T Effector Cell Silencing Molecule

In some embodiments, an effector binding/modulating moiety, e.g., comprises an antibody molecule, e.g., an scFv domain, that binds CTLA4 expressed on the surface of Tregs. The therapeutic molecule accumulates or retains CTLA4+ Tregs at the target site, with local immunosuppression the consequence.

Though expressed more highly on Tregs, CTLA4 is also expressed on activated T cells. A therapeutic compound comprising an effector binding/modulating moiety, e.g., an anti-CTLA4 antibody, or a functional anti-CTLA4 antibody, can down regulate the CTLA4 expressing T cell. Thus, in a therapeutic compound comprising an effector binding/modulating moiety that binds CTLA4, the effector moiety can also act as an ICIM binding/modulating moiety.

In some embodiments, the anti-CTLA4 binder is neither antagonizing or agonizing when in monomeric format, and is only agonizing when clustered or multimerized upon binding to the target.

While not wishing to be bound by theory it is believed that the binding of the therapeutic compound, via the targeting moiety, to the target, effects multimerization of therapeutic compound. In the case of memory and activated T cells, CTLA4 bound by the effector binding/modulating moiety of the therapeutic compound, is clustered, and an inhibitory signal by engagement of CTLA4 expressed by memory and activated T cells In some embodiments, the anti-CTLA4 binder is neither antagonizing or agonizing when in monomeric format, and is only agonizing when clustered or multimerized upon binding to the target.

GITR-Binders

GITR(CD357) is a cell surface marker present on Tregs. Blockade of the GITR-GITRL interaction maintains Treg function. In some embodiments, a therapeutic compound comprises an IIC binding entity that binds GITR-expressing Treg cells and a targeting moiety that targets the therapeutic compound to the target tissue of interest.

In some embodiments, a therapeutic compound comprises an anti-GITR antibody molecule, e.g., anti-GITR antibody molecule that inhibit binding of GITR to GITRL.

In some embodiments, a therapeutic compound comprises an anti-GITR antibody molecule, anti-GITR antibody molecule that inhibit binding of GITR to GITRL, and PD-1 agonist or other effector described herein.

While not wishing to be bound by theory, it is believed that the therapeutic compound that comprises a GITR binder effects accumulation of GITR-expressing Tregs at the site targeted by the targeting moiety of the therapeutic compound, e.g., a transplant or site of organ injury.

Butyrophilins/Butyrophilin-Like Molecules

Effector binding/modulating moiety can comprise an agonistic BTNL2 molecule. While not wishing to be bound by theory it is believed that agonistic BNL2 molecules induce Treg cells.

An agonistic BTNL2 molecule as that term as used herein, refers to a polypeptide having sufficient BTNL2 sequence that, as part of a therapeutic compound, it induces Treg cells. In some embodiments, a BTNL2 molecule has at least 60, 70, 80, 90, 95, 99, or 100% sequence identity, or substantial sequence identity, with a naturally occurring butyrophilin.

In some embodiments, an effector binding/modulating moiety an antagonistic BTNL8 molecule.

Therapeutic Compounds Comprising an SM Binding/Modulating Moiety: Manipulation of Local Microenvironment A therapeutic compound can comprise an effector binding/modulating moiety that promotes an immuno-suppressive local microenvironment, e.g., by providing in the proximity of the target, a substance that inhibits or minimizes attack by the immune system of the target, referred to herein a SM binding/modulating moiety.

In some embodiments, the SM binding/modulating moiety comprises a molecule that inhibits or minimizes attack by the immune system of the target (referred to herein as an SM binding/modulating moiety). In some embodiments, a therapeutic compound comprises an SM binding/modulating moiety that binds and accumulates a soluble substance, e.g., an endogenous or exogenous substance having immunosuppressive function. In some embodiments, a therapeutic compound comprises an SM binding/modulating moiety, e.g., a CD39 molecule or a CD73 molecule or alkaline phosphatase molecule, that binds, inhibits, sequesters, degrades or otherwise neutralizes a soluble substance, typically and endogenous soluble substance, e.g., ATP in the case of a CD39 molecule or alkaline phosphatase molecule, or AMP in the case of a CD73 molecule, that promotes immune attack. In some embodiments, a therapeutic compound comprises an SM binding/modulating moiety that comprises an immune-suppressive substance, e.g. a fragment of protein that is immunosuppressive.

Donor Tissue

Therapeutic compounds and methods described herein can be used in conjunction with a transplantation of donor tissue into a subject and can minimizes rejection of, minimizes immune effector cell mediated damage to, prolongs acceptance of, or prolongs the functional life of, donor transplant tissue. The tissue can be xenograft or allograft tissue. Transplanted tissue can comprise all or part of an organ, e.g., a liver, kidney, heart, pancreas, thymus, skin or lung. In embodiments, therapeutic compounds described herein reduce, or eliminate the need for systemic immune suppression. Therapeutic compounds and methods described herein can also be used to treat GVHD. In some embodiments, host cells are coated with a therapeutic compound that comprises, as an effector binding/modulating moiety, a PD-L1 molecule.

Table 2 provides target molecules for transplant indications. A target molecule is the target to which a targeting moiety binds. As discussed elsewhere herein, In some embodiments, a targeting moiety is selected that binds a product of an allele present on donor tissue and which is not expressed by the subject (recipient) or at expressed at a different level (e.g. reduced or substantially reduced).

TABLE 2

Target Molecules for Transplant Indications

| Indication | Organ/cell type | Target |
|---|---|---|
| Allograft transplant tissue, e.g., allograft solid organ transplant, GvHD | All | HLA-A, HLA-B, HLA-C, HLA-DP, HLA-DQ or HLA-DR |

TABLE 2-continued

Target Molecules for Transplant Indications

| Indication | Organ/cell type | Target |
|---|---|---|
| Transplant | Kidney | Antigens expressed in the kidney where immune cells infiltrate, for example including but not limited to the tubular interstitial region eg Uromodulin, SLC22A2, SLC22A6, FXYD4, SLC5A10, SLC6A13, AQP6, SLC13A3, TMEM72, BSND, NPR3, and the proximal and distal tubular epithelium, such as OAT1, OCT2 |

Auto-Immune Disorders

Therapeutic compounds and methods described herein can be used to treat a subject having or at risk for having an unwanted autoimmune response, e.g., an auto immune response in Type 1 Diabetes, Multiple Sclerosis, Cardiomyositis, vitiligo, alopecia, inflammatory bowel disease (IBD, e.g. Crohn's disease or ulcerative colitis), Sjogren's syndrome, focal segmented glomerular sclerosis (FSGS), scleroderma/systemic sclerosis (SSc) or rheumatoid arthritis. In some embodiments, the treatment minimizes rejection of, minimizes immune effector cell mediated damage to, prolongs the survival of subject tissue undergoing, or a risk for, autoimmune attack. Table 3 provides target molecules for several autoimmune indications and organ/cell types. A target molecule is the target to which a targeting moiety binds.

TABLE 3

Target Molecules for autoimmune indications

| Indication | Organ/cell type | Target Molecule |
|---|---|---|
| Type 1 Diabetes and Transplant | Pancreas/Pancreatic islets, beta cells | SEZ6L2, LRP11, DISP2, SLC30A8, FXYD2 TSPAN7 TMEM27 (reference Hald et al. 2012 Diabetelogia 55: 154); FXYD2; GPR119; HEPACAM2 |
| Multiple Sclerosis | CNS/myelin sheath of oligodendrocytes | MOG, PLP, MBP |
| Cardiomyositis, rheumatoid arthritis | Cardiomyocytes, monocytes, macrophages, myeloid cells | SIRPA (CD172a) |
| Inflammatory bowel disease (ulcerative colitis, Crohn's disease) or GVHD; Celiac disease | Intestine | MAdCAM |
| Autoimmune hepatitis (AIH); Primary Sclerosing Cholangitis (PSC); Primary Biliary Sclerosis; (PBC); transplant | liver | MAdCAM |
| Focal Segmented Glomerular Sclerosis (FSGS) and other diseases that can affect kidney for example lupus nephritis, systemic scleroderma, membranous glomerular nephropathy (MGN); Membranous nephropathy (MN); Minimal Change Disease (MCD); IgA nephropathy; ANCA-associated vasculitis (AAV) | Kidney, podocytes, tubules, epithelial cells | COL1A1, Cadherin 2, VCAM-1, Thy1, Podocin, KIM1 (Hodgin et al, Am J Pathol 177: 1675 2010); PLA2R; OAT1; OCT2; K-cadherin 6 |

TABLE 3-continued

Target Molecules for autoimmune indications

| Indication | Organ/cell type | Target Molecule |
| --- | --- | --- |
| Sjogren's syndrome | Salivary glands, epithelial cells, kidney | FCGR3B, HLAB, KIM1 (Hu et al Arth and Rheum 56: 3588 2007) |
| Scleroderma, systemic sclerosis (SSc) | skin, kidney, lung, Fibroblasts, connective tissue | Collagen I, III, VI, VII, fibronectin (Wang et al Arth and Rheum 54: 2271 2006) |
| vitiligo | Skin, epidermis, Langerhans cells, keratinocytes, melanocytes | COL17A1, CD1A, CD207, desmoglein 1-4, keratin 1 |
| Alopecia areata | Skin, Hair follicle/hair bulb, dermis | CD133 (Yang and Cotsarelis, J Dermatol Sci 57: 2 2010) |

Other examples of autoimmune disorders and diseases that can be treated with the compounds described herein include, but are not limited to, Myocarditis, Postmyocardial infarction syndrome, Postpericardiotomy syndrome, Subacute bacterial endocarditis, Anti-Glomerular Basement Membrane nephritis, Interstitial cystitis, Lupus nephritis, membranous glomerulonephropathy, Chronic Kidney Disease ("CKD"), Autoimmune hepatitis, Primary biliary cirrhosis, Primary sclerosing cholangitis, Antisynthetase syndrome, alopecia areata, autoimmune angioedema, autoimmune progesterone dermatitis, autoimmune urticaria, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear iga disease (lad), morphea, pemphigus vulgaris, pityriasis lichenoides et varioliformis *acuta*, mucha-habermann disease, psoriasis, systemic scleroderma, vitiligo, Addison's disease, Autoimmune polyendocrine syndrome (APS) type 1, Autoimmune polyendocrine syndrome (APS) type 2, Autoimmune polyendocrine syndrome (APS) type 3, Autoimmune pancreatitis (AIP), Diabetes mellitus type 1, Autoimmune thyroiditis, Ord's thyroiditis, Graves' disease, Autoimmune Oophoritis, Endometriosis, Autoimmune orchitis, Sjogren's syndrome, Autoimmune enteropathy, Coeliac disease, Crohn's disease, Microscopic colitis, Ulcerative colitis, thrombocytopenia, Adiposis, dolorosa, Adult-onset Still's, disease, Ankylosing, Spondylitis, CREST syndrome, Drug-induced lupus, Enthesitis-related arthritis, Eosinophilic fasciitis, Felty syndrome, IgG4-related disease, Juvenile, Arthritis, Lyme disease (Chronic), Mixed connective tissue disease (MCTD), Palindromic rheumatism, Parry Romberg syndrome, Parsonage-Turner syndrome, Psoriatic arthritis, Reactive arthritis, Relapsing polychondritis, Retroperitoneal fibrosis, Rheumatic fever, Rheumatoid arthritis, Sarcoidosis, Schnitzler syndrome, Systemic Lupus Erythematosus (SLE), Undifferentiated connective tissue disease (UCTD), Dermatomyositis, Fibromyalgia, Inclusion body myositis, Myositis, Myasthenia gravis, Neuromyotonia, Paraneoplastic cerebellar degeneration, Polymyositis, Acute disseminated encephalomyelitis (ADEM), Acute motor axonal neuropathy, Anti-N-Methyl-D-Aspartate (anti-NMDA) Receptor Encephalitis, Balo concentric sclerosis, Bickerstaff's encephalitis, Chronic inflammatory demyelinating polyneuropathy, Guillain-Barre syndrome, Hashimoto's encephalopathy, Idiopathic inflammatory demyelinating diseases, Lambert-Eaton myasthenic syndrome, Multiple sclerosis, Oshtoran syndrome, Pediatric Autoimmune Neuropsychiatric Disorder Associated with Streptococcus (PANDAS), Progressive inflammatory neuropathy, Restless leg syndrome, Stiff person syndrome, Sydenham chorea, Transverse myelitis, Autoimmune retinopathy, Autoimmune uveitis, Cogan syndrome, Graves ophthalmopathy, Intermediate uveitis, Ligneous conjunctivitis, Mooren's ulcer, Neuromyelitis optica, Opsoclonus myoclonus syndrome, Optic neuritis, Scleritis, Susac's syndrome, Sympathetic ophthalmia, Tolosa-Hunt syndrome, Autoimmune inner ear disease (AIED), Meniere's disease, Behcet's disease, Eosinophilic granulomatosis with polyangiitis (EGPA), Giant cell arteritis, Granulmatosis with polyangiitis (GPA), IgA vasculitis (IgAV), Kawasaki's disease, Leukocytoclastic vasculitis, Lupus vasculitis, Rheumatoid vasculitis, Microscopic polyangiitis (MPA), *Polyarteritis nodosa* (PAN), Polymyalgia rheumaticia, Vasculitis, Primary Immune Deficiency, and the like.

Other examples of potential autoimmune disorders and diseases, as well as autoimmune comorbidities that can be treated with the compounds described herein include, but are not limited to, Chronic fatigue syndrome, Complex regional pain syndrome, Eosinophilic esophagitis, Gastirtis, Interstitial lung disease, POEMS syndrome, Raynaud's phenomenon, Primary immunodeficiency, Pyoderma gangrenosum, Agammaglobulinemia, Anyloidosis, Anyotrophic lateral sclerosis, Anti-tubular basement membrane nephritis, Atopic allergy, Atopic dermatitis, Autoimmune peripheral neuropathy, Blau syndrome, Castleman's disease, Chagas disease, Chronic obstructive pulmonary disease, Chronic recurrent multifocal osteomyelitis, Complement component 2 deficiency, Contact dermatitis, Cushing's syndrome, Cutaneous leukocytoclastic angiitis, Dego' deiase, Eczema, Eosinophilic gastroenteritis, Eosinophilic pneumonia, Erythroblastosis fetalsis, Fibrodysplasia ossificans progressive, Gastrointestinal pemphigoid, Hypogammaglobulinemia, Idiopathic giant-cell myocarditis, Idiopathic pulmonary fibrosis, IgA nephropathy, Immunregulatory lipoproteins, IPEX syndrome, Ligenous conjunctivitis, Majeed syndrome, Narcolepsy, Rasmussen's encephalitis, Schizophrenia, Serum sickness, Spondyloathropathy, Sweet's syndrome, Takayasu's arteritis, and the like.

In some embodients, the autoimmune disorder does not comprise pemphigus Vulgaris, pemphigus. In some embodiments, the autoimmune disorder does not comprise pemphigus foliaceus. In some embodiments, the autoimmune disorder does not comprise bullous pemphigoid. In some embodiments, the autoimmune disorder does not comprise Goodpasture's Disease. In some embodiments, the autoimmune disorder does not comprise psoriasis. In some embodiments, the autoimmune disorder does not comprise a skin disorder. In some embodiments, the disorder does not comprise a neoplastic disorder, e.g., cancer.

Therapeutic Compounds

A therapeutic compound comprises a specific targeting moiety functionally associated with an effector binding/modulating moiety. In some embodiments, the specific targeting moiety and effector binding/modulating moiety are linked to one another by a covalent or noncovalent bond, e.g., a covalent or non-covalent bond directly linking the one to the other. In other embodiments, a specific targeting moiety and effector binding/modulating moiety are linked, e.g., covalently or noncovalently, through a linker moiety. E.g., in the case of a fusion polypeptide, a polypeptide sequence comprising the specific targeting moiety and a polypeptide sequence can be directly linked to one another or linked through one or more linker sequences. In some embodiments, the linker moiety comprises a polypeptide. Linkers are not, however, limited to polypeptides. In some embodiments, a linker moiety comprises other backbones, e.g., a non-peptide polymer, e.g., a PEG polymer. In some embodiments, a linker moiety can comprise a particle, e.g., a nanoparticle, e.g., a polymeric nanoparticle. In some embodiments, a linker moiety can comprise a branched molecule, or a dendrimer. However, in embodiments where the effector binding/modulating moiety comprises an ICIM binding/modulating moiety (which binds an effector like PD-1) structures that result in clustering in the absence of target binding should be avoided as they may cause clustering in the absence of target binding. Thus in embodiments, the therapeutic compound has a structure, e.g., the copies of an ICIM are sufficiently limited, such that clustering in the absence of target binding is minimized or substantially eliminated, or eliminated, or is sufficiently minimized that substantial systemic immune suppression does not occur.

In some embodiments, a therapeutic compound comprises a polypeptide comprising a specific targeting moiety covalently or non-covalently conjugated to an effector binding/modulating moiety. In some embodiments, a therapeutic molecule comprises a fusion protein having comprising a specific targeting moiety fused, e.g., directly or through a linking moiety comprising one or more amino acid residues, to an effector binding/modulating moiety. In some embodiments, a therapeutic molecule comprises a polypeptide comprising a specific targeting moiety linked by a non-covalent bond or a covalent bond, e.g., a covalent bond other than a peptide bond, e.g., a sulfhydryl bond, to an effector binding/modulating moiety.

In some embodiments, a therapeutic compound comprises polypeptide, e.g., a fusion polypeptide, comprising:

1.a) a specific targeting moiety comprising a target specific binding polypeptide;

1.b) a specific targeting moiety comprising a target ligand binding molecule;

1.c) a specific targeting moiety comprising an antibody molecule;

1.d) a specific targeting moiety comprising a single chain antibody molecule, e.g., a scFv domain; or 1.e) a specific targeting moiety comprising a first of the light or heavy chain variable region of an antibody molecule, and wherein the other variable region is covalently or non covalently associated with the first;
and 2.a) an effector binding/modulating moiety comprising an effector specific binding polypeptide;

2.b) an effector binding/modulating moiety comprising an effector ligand binding molecule;

2.c) an effector binding/modulating moiety comprising an antibody molecule;

2.d) an effector binding/modulating moiety comprising a single chain antibody molecule, e.g., a scFv domain; or 2.e) an effector binding/modulating moiety comprising a first of the light or heavy chain variable region of an antibody molecule, and wherein the other variable region is covalently or non covalently associated with the first.

In some embodiments, a therapeutic compound comprises 1.a and 2.a.

In some embodiments, a therapeutic compound comprises 1.a and 2.b.

In some embodiments, a therapeutic compound comprises 1.a and 2.c.

In some embodiments, a therapeutic compound comprises 1.a and 2.d.

In some embodiments, a therapeutic compound comprises 1.a and 2.e.

In some embodiments, a therapeutic compound comprises 1.b and 2.a.

In some embodiments, a therapeutic compound comprises 1.b and 2.b.

In some embodiments, a therapeutic compound comprises 1.b and 2.c.

In some embodiments, a therapeutic compound comprises 1.b and 2.d.

In some embodiments, a therapeutic compound comprises 1.b and 2.e.

In some embodiments, a therapeutic compound comprises 1.c and 2.a.

In some embodiments, a therapeutic compound comprises 1.c and 2.b.

In some embodiments, a therapeutic compound comprises 1.c and 2.c.

In some embodiments, a therapeutic compound comprises 1.c and 2.d.

In some embodiments, a therapeutic compound comprises 1.c and 2.e.

In some embodiments, a therapeutic compound comprises 1.d and 2.a.

In some embodiments, a therapeutic compound comprises 1.d and 2.b.

In some embodiments, a therapeutic compound comprises 1.d and 2.c.

In some embodiments, a therapeutic compound comprises 1.d and 2.d.

In some embodiments, a therapeutic compound comprises 1.d and 2.e.

In some embodiments, a therapeutic compound comprises 1.e and 2.a.

In some embodiments, a therapeutic compound comprises 1.e and 2.b.

In some embodiments, a therapeutic compound comprises 1.e and 2.c.

In some embodiments, a therapeutic compound comprises 1.e and 2.d.

In some embodiments, a therapeutic compound comprises 1.e and 2.e.

Therapeutic compounds disclosed herein can, for example, comprise a plurality of effector binding/modulating and specific targeting moieties. Any suitable linker or platform can be used to present the plurality of moieties. The linker is typically coupled or fused to one or more effector binding/modulating and targeting moieties.

In some embodiments, two (or more) linkers associate, either covalently or noncovelaently, e.g., to form a hetero or homo-dimeric therapeutic compound. E.g., the linker can comprise an Fc region and two Fc regions associate with one another. In some embodiments of a therapeutic compound comprising two linker regions, the linker regions can self associate, e.g., as two identical Fc regions. In some embodiments of a therapeutic compound comprising two linker regions, the linker regions are not capable of, or not capable of substantial, self association, e.g., the two Fc regions can be members of a knob and hole pair.

Non-limiting exemplary configurations of therapeutic compounds comprise the following (e.g., in N to C terminal order):

R1—Linker Region A—R2
R3—Linker Region B—R4, wherein,

R1, R2, R3, and R4, each independently comprises an effector binding/modulating moiety, e.g., an ICIM binding/modulating moiety, an IIC binding/modulating moiety, or an SM binding/modulating moiety; a specific targeting moiety; or is absent;

Linker Region A and Linker B comprise moieties that can associate with one another, e.g., Linker A and Linker B each comprises an Fc moiety provided that an effector binding/modulating moiety and a specific targeting moiety are present.

In some embodiments:

R1 comprises an effector binding/modulating moiety, e.g., an ICIM binding/modulating moiety, an IIC binding/modulating moiety, or an SM binding/modulating moiety, or is absent;

R2 comprises a specific targeting moiety, or is absent;

R3 comprises an effector binding/modulating moiety, e.g., an ICIM binding/modulating moiety, an IIC binding/modulating moiety, or an SM binding/modulating moiety, or is absent;

R4 comprises a specific targeting moiety, or is absent;

Linker Region A and Linker B comprise moieties that can associate with one another, e.g., Linker A and Linker B each comprises an Fc moiety, provided that one of R1 or R3 is present and one of R2 or R4 is present.

In some embodiments:

R1 comprises a specific targeting moiety, or is absent;

R2 comprises an effector binding/modulating moiety, e.g., an ICIM binding/modulating moiety, an IIC binding/modulating moiety, or an SM binding/modulating moiety, or is absent;

R3 comprises a specific targeting moiety, or is absent;

R4 comprises an effector binding/modulating moiety, e.g., an ICIM binding/modulating moiety, an IIC binding/modulating moiety, or an SM binding/modulating moiety, or is absent;

Linker Region A and Linker B comprise moieties that can associate with one another, e.g., Linker A and Linker B each comprises an Fc moiety, provided that one of R1 or R3 is present and one of R2 or R4 is present.

Non-limiting examples include, but are not limited to:

| R1 | Linker Region A | R2 | R3 | Linker Region B | R4 | Other |
|---|---|---|---|---|---|---|
| HCVR and LCVR | Fc Region | fcFv | HCVR and LCVR | Fc Region | scFv | Self Pairing Linker Regions |
| HCVR and LCVR | Fc Region | fcFv | HCVR and LCVR | Fc Region | scFv | Non-Self Pairing linker regions |
| HCVR and LCVR (or absent) | Fc Region | fcFv | HCVR and LCVR (or absent) | Fc Region | scFv | Self Pairing Linker Regions One of R1 or R3 is absent. |
| HCVR and LCVR (or absent) | Fc Region | fcFv | HCVR and LCVR (or absent) | Fc Region | scFv | Non-Self Pairing Linker Regions One of R1 or R3 is absent. |
| HCVR and LCVR | Fc Region | fcFv (or absent) | HCVR and LCVR | Fc Region | scFv (or absent) | Self Pairing linker regions One of R2 or R4 is absent. |
| HCVR and LCVR | Fc Region | fcFv (or absent) | HCVR and LCVR | Fc Region | scFv (or absent) | Non-Self Pairing linker regions One of R2 or R4 is absent. |
| HCVR and LCVR | Fc Region | fcFv | HCVR and LCVR | Fc Region | scFv | Self Pairing Linker Regions R1 and R3 are the same |
| HCVR and LCVR | Fc Region | fcFv | HCVR and LCVR | Fc Region | scFv | Non-Self Pairing linker regions R1 and R3 are different |
| HCVR and LCVR | Fc Region | fcFv | HCVR and LCVR | Fc Region | scFv | Self Pairing Linker Regions R2 and R4 are the same |

| R1 | Linker Region A | R2 | R3 | Linker Region B | R4 | Other |
|---|---|---|---|---|---|---|
| HCVR and LCVR | Fc Region | fcFv | HCVR and LCVR | Fc Region | scFv | Non-Self Pairing linker regions R2 and R4 are different |

HCVR and LCVR: refers to an moiety comprising an antigen binding portion of a heavy and light chian variable region, typically with the heavy chain fused to the Linker region.
Self pairing: wherein a liker region can pair with itself, e.g., an Fc region that can pair a copy of itself.
Non-Self Pairing: wherein a Linker Region does not pair with itself, or does not substantially pair with itself, e.g., an Fc region does not or does not significantly pair with itself, e.g., wherein Linker Region A and Linker Region B are members of a knob and hole pair.

In some embodiments:
R1, R2, R3 and R4 each independently comprise: an effector binding modulating moiety that activates an inhibitory receptor on an immune cell, e.g., a T cell or a B cell, e.g., a PD-L1 molecule or a functional anti-PD-1 antibody molecule (an agonist of PD-1); a specific targeting moiety; or is absent;
provided that an effector binding moiety and a specific targeting moiety are present.
In some embodiments, Linker A and Linker B comprise Fc moieties (e.g., self pairing Fc moieties).
In some embodiments:
R1 and R3 independently comprise an effector binding modulating moiety that activates an inhibitory receptor on an immune cell, e.g., a T cell or a B cell, e.g., a PD-L1 molecule or an functional anti-PD-1 antibody molecule (an agonist of PD-1); and
R2 and R4 independently comprise specific targeting moieties, e.g., scFv molecules against a tissue antigen.
In some embodiments, Linker A and Linker B comprise Fc moieties (e.g., self pairing Fc moieties).
In some embodiments:
R1 and R3 independently comprise a functional anti-PD-1 antibody molecule (an agonist of PD-1); and
R2 and R4 independently comprise specific targeting moieties, e.g., scFv molecules against a tissue antigen.
In some embodiments, Linker A and Linker B comprise Fc moieties (e.g., self pairing Fc moieties).
In some embodiments:
R1 and R3 independently comprise specific targeting moieties, e.g., an anti-tissue antigen antibody; and
R2 and R4 independently comprise a functional anti-PD-1 antibody molecule (an agonist of PD-1), e.g., an scFv molecule.
In some embodiments, Linker A and Linker B comprise Fc moieties (e.g., self pairing Fc moieties).
In some embodiments:
R1 and R3 independently comprise a PD-L1 molecule (an agonist of PD-1); and
R2 and R4 independently comprise specific targeting moieties, e.g., scFv molecules against a tissue antigen; and
In some embodiments, Linker A and Linker B comprise Fc moieties (e.g., self pairing Fc moieties).
In some embodiments:
R1 and R3 independently comprise specific targeting moieties, e.g., an anti-tissue antigen antibody; and
R2 and R4 independently comprise a PD-L1 molecule (an agonist of PD-1).
In some embodiments, Linker A and Linker B comprise Fc moieties (e.g., self pairing Fc moieties).

In some embodiments:
R1, R2, R3 and R4 each independently comprise: an SM binding/modulating moiety which modulates, e.g., binds and inhibits, sequesters, degrades or otherwise neutralizes a substance, e.g., a soluble molecule that modulates an immune response, e.g., ATP or AMP, e.g., a CD39 molecule or a CD73 molecule; a specific targeting moiety; or is absent;
provided that an SM binding/modulating moiety and a specific targeting moiety are present.
In some embodiments, Linker A and Linker B comprise Fc moieties (e.g., self pairing Fc moieties or Fc moieties that do not, or do not substantially self pair).
In some embodiments:
R1 and R3 independently comprise an SM binding/modulating moiety which modulates, e.g., binds and inhibits, sequesters, degrades or otherwise neutralizes a substance, e.g., a soluble molecule that modulates an immune response, e.g., ATP or AMP, e.g., a CD39 molecule or a CD73 molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1 and R3 independently comprise a CD39 molecule or a CD73 molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1 and R3 each comprises a CD39 molecule; and
R2 and R4 independently comprise specific targeting moieties, e.g., scFv molecules against a tissue antigen; and
In some embodiments, Linker A and Linker B comprise Fc moieties (e.g., self pairing Fc moieties or Fc moieties that do not, or do not substantially self pair).
In some embodiments:
R1 and R3 each comprises a CD73 molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
One of R1 and R3 comprises a CD39 molecule and the other comprises a CD73 molecule; and
R2 and R4 independently comprise specific targeting moieties, e.g., scFv molecules against a tissue antigen.

In some embodiments, Linker A and Linker B comprise Fc moieties (e.g., self pairing Fc moieties or Fc moieties that do not, or do not substantially self pair).
In some embodiments:
R1, R2, R3 and R4 each independently comprise: an HLA-G molecule; a specific targeting moiety; or is absent;
provided that an HLA-G molecule and a specific targeting moiety are present.
In some embodiments, Linker A and Linker B comprise Fc moieties (e.g., self pairing Fc moieties or Fc moieties that do not, or do not substantially self pair).
In some embodiments:
R1 and R3 each comprise an HLG-A molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1 and R3 each comprise an agonistic anti-LILRB1 antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1 and R3 each comprise an agonistic anti-KIR2DL4 antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1 and R3 each comprise an agonistic anti-LILRB2 antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1 and R3 each comprise an agonistic anti-NKG2A antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
one of R1 and R3 comprises a first moiety chosen from, and the other comprises a different moiety chosen from: an antagonistic anti-LILRB1 antibody molecule, an agonistic anti-KR2DL4 antibody molecule, and an agonistic anti-NKG2A antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
one of R1 and R3 comprises an antagonistic anti-LILRB1 antibody molecule and the other comprises an agonistic anti-KR2DL4 antibody molecule; and
R2 and R4 independently comprise specific targeting moieties, e.g., scFv molecules against a tissue antigen.

In some embodiments, Linker A and Linker B comprise Fc moieties (e.g., self pairing Fc moieties or Fc moieties that do not, or do not substantially self pair).
In some embodiments:
one of R1 and R3 comprises an antagonistic anti-LILRB1 antibody molecule and the other comprises an agonistic anti-NKG2A antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In some embodiments:
R1, R2, R3 and R4 each independently comprise: an effector binding modulating moiety that activates an inhibitory receptor on a B cell, e.g., an anti-FCRL antibody molecule, e.g., an agonistic anti-FCRL antibody molecule; a specific targeting moiety; or is absent; provided that an effector binding moiety and a specific targeting moiety are present.
In some embodiments, Linker A and Linker B comprise Fc moieties (e.g., self pairing Fc moieties or Fc moieties that do not, or do not substantially self pair).
In embodiment the anti-FCRL molecule comprises: an anti-FCRL antibody molecule, e.g., an agonistic anti-FCRL antibody molecule, directed to FCRL1, FCRL2, FCRL3, FCRL4, FCRL5, or FCRL6.
In some embodiments:
R1 and R3 each comprises an agonistic anti-FCRL antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
In embodiment the anti-FCRL molecule comprises: an anti-FCRL antibody molecule, e.g., an agonistic anti-FCRL antibody molecule directed to FCRL1, FCRL2, FCRL3, FCRL4, FCRL5, or FCRL6.
In some embodiments:
R1 and R3 independently comprise specific targeting moieties, e.g., antibody molecules against a tissue antigen; and
R2 and R4 each comprises an anti-FCRL antibody molecule, e.g., an agonistic anti-FCRL antibody molecule, e.g., an scFv molecule.
In some embodiments, Linker A and Linker B comprise Fc moieties (e.g., self pairing Fc moieties or Fc moieties that do not, or do not substantially self pair).
In embodiment the anti-FCRL molecule comprises: an anti-FCRL antibody molecule, e.g., an agonistic anti-FCRL antibody molecule directed to FCRL1, FCRL2, FCRL3, FCRL4, FCRL5, or FCRL6.
In some embodiments:
One of R1, R2, R3 and R4 comprises an anti-BCR antibody molecule, e.g., an antagonistic anti-BCR antibody molecule, one comprises an anti FCRL antibody molecule, and one comprises a specific targeting moiety.
In some embodiments, Linker A and Linker B comprise Fc moieties (e.g., self pairing Fc moieties or Fc moieties that do not, or do not substantially self pair).
In some embodiments, the anti-FCRL molecule comprises: an anti-FCRL antibody molecule, e.g., an agonistic anti-FCRL antibody molecule directed to FCRL1, FCRL2, FCRL3, FCRL4, FCRL5, or FCRL6.
In some embodiments:
One of R1, R2, R3 and R4 comprises a bispecific antibody molecule comprising an anti-BCR antibody molecule, e.g., an antagonistic anti-BCR antibody molecule, and an anti FCRL antibody molecule, and one comprises a specific targeting moiety; In some embodiments, Linker A and Linker B comprise Fc moieties (e.g., self pairing Fc moieties or Fc moieties that do not, or do not substantially self pair).

In embodiment the anti-FCRL molecule comprises: an anti-FCRL antibody molecule, e.g., an agonistic anti-FCRL antibody molecule directed to FCRL1, FCRL2, FCRL3, FCRL4, FCRL5, or FCRL6.

In some embodiments:

R1, R2, R3 and R4 each independently comprise:

i) an effector binding/modulating moiety, e.g., an ICIM binding/modulating moiety, an IIC binding/modulating moiety, ICSM binding/modulating moiety, or an SM binding/modulating moiety, that minimizes or inhibits T cell activity, expansion, or function (a T cell effector binding/modulating moiety);

ii) an effector binding/modulating moiety, e.g., an ICIM binding/modulating moiety, an IIC binding/modulating moiety, ICSM binding/modulating moiety, or an SM binding/modulating moiety, that minimizes or inhibits B cell activity, expansion, or function (a B cell effector binding/modulating moiety);

iii) a specific targeting moiety; or iv) is absent;

provided that, a T cell effector binding/modulating moiety, a B cell effector binding/modulating moiety, and a specific targeting moiety are present.

In some embodiments, Linker A and Linker B comprise Fc moieties (e.g., self pairing Fc moieties).

In some embodiments, one of R1, R2, R3, and R4 comprises an agonistic anti-PD-1 antibody and one comprises an HLA-G molecule.

In some embodiments, one of R1, R2, R3, and R4 comprises an SM binding/modulating moiety, e.g., a CD39 molecule or a CD73 molecule. In some embodiments, one of R1, R2, R3, and R4 comprises an entity that binds, activates, or maintains, a regulatory immune cell, e.g., a Treg cell or a Breg cell.

In some embodiments, one of R1, R2, R3, and R4 comprises an agonistic anti-PD-1 antibody, or one comprises an HLA-G molecule. In some embodiments, one of R1, R2, R3, and R4 comprises an agonistic anti-PD-1 antibody, one comprises an HLA-G molecule, and one comprises CD39 molecule or a CD73 molecule.

Linker Regions

As discussed elsewhere herein specific targeting and effector binding/modulating moieties can be linked by linker regions. Any linker region described herein can be used as a linker. For example, linker Regions A and B can comprise Fc regions. In some embodiments, a therapeutic compound comprises a Linker Region that can self-associate. In some embodiments, a therapeutic compound comprises a Linker Region that has a moiety that minimizes self association, and typically Linker Region A and Linker Region B are heterodimers. Linkers also include glycine/serine linkers. In some embodiments, the linker can comprise one or more repeats of GGGGS (SEQ ID NO: 6). In some embodiments, the linker comprises 1, 2, 3, 4, or 5 repeats. In some embodiments, the linker comprises GGGGSGGGGS (SEQ ID NO: 7). In some embodiments, the linker comprises GGGGSGGGGSGGGGS (SEQ ID NO: 8). These linkers can be used in any of the therapeutic compounds or compositions provided herein.

In some embodiments, the therapeutic compounds comprise, wherein the therapeutic compound is a polypeptide. In some embodiments, the polypeptide comprises at the N-terminus an antibody comprised of F(ab')2 on an IgG1 Fc backbone fused with scFvs on the C-terminus of the IgG Fc backbone. In some embodiments, the IgG Fc backbone is a IgG1 Fc backbone. In some embodiments, the IgG1 backbone is replaced with a IgG4 backbone, IgG2 backbone, or other similar IgG backbone. The IgG backbones described in this paragraph can be used throughout this application where a Fc region is referred to as part of the therapeutic compound. Thus, in some embodiments, the antibody comprised of F(ab')2 on an IgG1 Fc backbone can be an anti-MAdCAM antibody or an anti-PD-1 antibody on an IgG1 Fc or any other targeting moiety or effector binding/modulating moiety provided herein. In some embodiments, the The scFV segments fused to the C-terminus could be an anti-PD-1 antibody, if the N-terminus region is an anti-MAdCAM antibody, or anti-MAdCAM antibody, if the N-terminus region is an anti-PD-1 antibody. In this non-limiting example, the N-terminus can be the targeting moiety, such as any one of the ones provided for herein, and the C-terminus can be the effector binding/modulating moiety, such as any of the ones provided for herein. Alternatively, in some embodiments, the N-terminus can be the effector binding/modulating moiety, such as any one of the ones provided for herein, and the C-terminus can be the targeting moiety, such as any of the ones provided for herein.

In some embodiments, the N-terminus can be the targeting moiety, such as any one of the ones provided for herein, and the C-terminus can be the effector binding/modulating moiety, such as any of the ones provided for herein.

In some embodiments, the therapeutic compound comprises two polypeptides that homodimerize. In some embodiments, the N-terminus of the polypeptide comprises an effector binding/modulating moiety that is fused to a human IgG1 Fc domain (e.g. CH2 and/or CH3 domains). In some embodiments, the C-terminus of the Fc domain is another linker that is fused to the targeting moiety. Thus, in some embodiments, the molecule could be represented using the formula of R1-Linker A-Fc Region-Linker B-R2, wherein R1 can be an effector binding/modulating moiety, R2 is a targeting moiety, Linker A and Linker B are independently linkers as provided for herein. In some embodiments, Linker 1 and Linker 2 are different.

In some embodiments, the molecule could be represented using the formula of R1-Linker A-Fc Region-Linker B-R2, wherein R1 can be a targeting moiety, R2 is an effector binding/modulating moiety, Linker A and Linker B are independently linkers as provided for herein. In some embodiments, Linker A and Linker B are different. The linkers can be chosen from the non-limiting examples provided for herein. In some embodiments, R1 and R2 are independently selected from F(ab')2 and scFV antibody domains. In some embodiments, R1 and R2 are different antibody domains. In some embodiments, the scFV is in the VL-VH domain orientation.

In some embodiments, the therapeutic compound is a bispecific antibody. In some embodiments, the bispecific antibodies are comprised of four polypeptide chains comprising the following:

Chain 1: nt-VH1-CH1-CH2-CH3-Linker A-scFv[VL2-Linker B-VH2]-ct

Chain 2: nt-VH1-CH1-CH2-CH3-Linker A-scFv[VL2-Linker B-VH2]-ct

Chain 3: nt-VL1-CL-ct

Chain 4: nt-VL1-CL-ct, wherein chains 1 and 2 are identical to each other, and chains 3 and 4 are identical to each other, wherein chain 1 forms a homodimer with chain 2; and chain 3 and 4 associate with chain 1 and chain 2. That is, when each light chain associates with each heavy chain, VL1 associates with VH1 and CL associates with CH1 to form two functional Fab units. Without being bound to any particular theory, each scFv unit is intrinsically functional since VL2 and VH2 are covalently linked in tandem with a linker as provided herein (e.g. GGGGSG (SEQ ID NO: 6), GGGGSGGGGSGGGGSGGGGS (SEQ ID NO: 9), GGGGSGGGGSGGGGS (SEQ ID NO: 8) or GGGGSGGGGS (SEQ ID NO: 7). The sequences of Linker A and Linker B, which are independent of one another can be the same or different and as otherwise described throughout the present application. Thus, in some embodiments, Linker A comprises GGGGS (SEQ ID NO: 6) GGGGSGGGGS (SEQ ID NO: 7), GGGGSGGGGSGGGGS (SEQ ID NO: 8), or GGGGSGGGGSGGGGSGGGGS (SEQ ID NO: 9). In some embodiments, Linker B comprises GGGGS (SEQ ID NO: 6) GGGGSGGGGS (SEQ ID NO: 7), GGGGSGGGGSGGGGS (SEQ ID NO: 8), or GGGGSGGGGSGGGGSGGGGS (SEQ ID NO: 9). The scFv may be arranged in the NT-VH2-VL2-CT or NT-VL2-VH2-CT orientation. NT or nt stands for N-terminus and CT or ct stands for C-terminus of the protein. CH1, CH2, and CH3 are the domains from the IgG Fc region, and CL stands for Constant Light chain, which can be either kappa or lambda family light chains. The other definitions stand for the way they are normally used in the art.

In some embodiments, the VH1 and VL1 domains are derived from the effector molecule and the VH2 and VL2 domains are derived from the targeting moiety. In some embodiments the VH1 and VL1 domains are derived from a targeting moiety and the VH2 and VL2 domains are derived from an effector binding/modulating moiety.

In some embodiments, the VH1 and VL1 domains are derived from an anti-PD-1 antibody, and the VH2 and VL2 domains are derived from an anti-MAdCAM antibody. In some embodiments the VH1 and VL1 domains are derived from an anti-MAdCAM antibody and the VH2 and VL2 domains are derived from an anti-PD-1 antibody.

In some embodiments, Linker A comprises 1, 2, 3, 4, or 5 GGGGS (SEQ ID NO: 6) repeats. In some embodiments, Linker B comprises 1, 2, 3, 4, or 5 GGGGS repeats. For the avoidance of doubt, the sequences of Linker A and Linker B, which are used throughout this application, are independent of one another. Therefore, in some embodiments, Linker A and Linker B can be the same or different. In some embodiments, Linker A comprises GGGGS (SEQ ID NO: 6) GGGGSGGGGS (SEQ ID NO: 7), GGGGSGGGGSGGGGS (SEQ ID NO: 8), or GGGGSGGGGSGGGGSGGGGS (SEQ ID NO: 9). In some embodiments, Linker B comprises GGGGS (SEQ ID NO: 6) GGGGSGGGGS (SEQ ID NO: 7), GGGGSGGGGSGGGGS (SEQ ID NO: 8), or GGGGSGGGGSGGGGSGGGGS (SEQ ID NO: 9).

In some embodiments, the therapeutic compound comprises a light chain and a heavy chain. In some embodiments, the light and heavy chain begin at the N-terminus with the VH domain of a targeting moiety followed by the CH1 domain of a human IgG1, which is fused to a Fc region (e.g. CH2-CH3) of human IgG1. In some embodiments, at the c-terminus of the Fc region is fused to a linker as provided herein, such as but not limited to, GGGGS (SEQ ID NO: 6), GGGGSGGGGS (SEQ ID NO: 7) or GGGGSGGGGSGGGGS (SEQ ID NO: 8). The linekr can then be fused to an effector binding/modulating moiety, such as any one of the effector moieties provided for herein. The polypeptides can homodimerize because through the heavy chain homodimerization, which results in a therapeutic compound having two effector moieties, such as two anti-PD-1 antibodies. In this orientation, the targeting moiety is an IgG format, there are two Fab arms that each recognize binding partner of the targeting moiety, for example, MAd-CAM being bound by the anti-MAdCAM targeting moiety.

In some embodiments, if the therapeutic compound comprises a Fc portion, the Fc domain, (portion) bears mutations to render the Fc region "effectorless," that is unable to bind FcRs. The mutations that render Fc regions effectorless are known. In some embodiments, the mutations in the Fc region, which is according to the known numbering system, are selected from the group consisting of: K322A, L235A, L236A, G237A, L235F, L236E, N297, P331S, or any combination thereof. In some embodiments, the Fc mutations comprises a mutation at L235 and/or L236 and/or G237. In some embodiments, the Fc mutations comprise L235A and/or L236A mutations, which can be referred to as. In some embodiments, the Fc mutations comprise L235A, L236A, and G237A mutations.

Disclosed herein are Linker Region polypeptides, therapeutic peptides, and nucleic acids encoding the polypeptides (e.g. therapeutic compounds), vectors comprising the nucleic acid sequences, and cells comprising the nucleic acids or vectors Therapeutic compounds can comprise a plurality of specific targeting moieties. In some embodiments, the therapeutic compound comprises a plurality one specific targeting moiety, a plurality of copies of a donor specific targeting moiety or a plurality of tissue specific targeting moieties. In some embodiments, a therapeutic compound comprises a first and a second donor specific targeting moiety, e.g., a first donor specific targeting moiety specific for a first donor target and a second donor specific targeting moiety specific for a second donor target, e.g., wherein the first and second target are found on the same donor tissue. In some embodiments, the therapeutic compound comprises e.g., a first specific targeting moiety for a tissue specific target and a second specific targeting moiety for a second target, e.g., wherein the first and second target are found on the same or different target tissue, In some embodiments, a therapeutic compound comprises a plurality of effector binding/modulating moieties each comprising an ICIM binding/modulating moiety, the number of ICIM binding/modulating moieties is sufficiently low that clustering of the ICIM binding/modulating moiety's ligand on immune cells (in the absence of target binding) is minimized, e.g., to avoid systemic agonizing of immune cells in the absence of binding of the therapeutic compound to target.

Polypeptides Derived from Reference, e.g., Human Polypeptides

In some embodiments, a component of a therapeutic molecule is derived from or based on a reference molecule, e.g., in the case of a therapeutic molecule for use in humans, from a naturally occurring human polypeptide. E.g., In some embodiments, all or a part of a CD39 molecule, a CD73 molecule, a cell surface molecule binder, a donor specific targeting moiety, an effector ligand binding molecule, an ICIM binding/modulating moiety, an IIC binding/modulating moiety, an inhibitory immune checkpoint molecule ligand molecule, an inhibitory molecule counter ligand molecule, a SM binding/modulating moiety, a specific targeting moiety, a target ligand binding molecule, or a tissue specific targeting moiety, can be based on or derived from a naturally occurring human polypeptide. E.g., a PD-L1 molecule can be based on or derived from a human PD-L1 sequence.

In some embodiments, a therapeutic compound component, e.g., a PD-L1 molecule:
a) comprises all or a portion of, e.g., an active portion of, a naturally occurring form of the human polypeptide;
b) comprises all or a portion of, e.g., an active portion of, a human polypeptide having a sequence appearing in a database, e.g., GenBank database, on Jan. 11, 2017, a naturally occurring form of the human polypeptide that is not associated with a disease state;
c) comprises a human polypeptide having a sequence that differs by no more than 1, 2, 3, 4, 5, 10, 20, or 30 amino acid residues from a sequence of a) or b);
d) comprises a human polypeptide having a sequence that differs at no more than by 1, 2, 3, 4, 5 10, 20, or 30% its amino acids residues from a sequence of a) or b);
e) comprises a human polypeptide having a sequence that does not differ substantially from a sequence of a) or b); or
f) comprises a human polypeptide having a sequence of c), d), or e) that does not differ substantially in a biological activity, e.g., ability to enhance or inhibit an immune response, from a human polypeptide having the sequence of a) or b).

In some embodiments, therapeutic compounds can comprise a plurality of effector binding/modulating moieties. For example, a therapeutic compound can comprise two or more of the following selected from:
(a) an ICIM binding/modulating moiety; (b) an IIC binding/modulating moiety; or (c) an SM binding/modulating moiety. In some embodiments, for example, a therapeutic compound can comprise a plurality, e.g., two, ICIM binding/modulating moieties (wherein they are the same or different); by way of example, two that activate or agonize PD-1; a plurality, e.g., two, IIC binding/modulating moieties; (wherein they are the same or different); or a plurality, e.g., two, SM binding/modulating moieties (wherein they are the same or different). In some embodiments, the therapeutic compound can comprise an ICIM binding/modulating moiety and an IIC binding/modulating moiety; an ICIM binding/modulating moiety and an SM binding/modulating moiety; an IIC binding/modulating moiety and an SM binding/modulating moiety. In some embodiments, the therapeutic compound comprises a plurality of targeting moieties. In some embodiments, the targeting moieties can be the same or different.

Pharmaceutical Compositions and Kits

In another aspect, the present embodiments provide compositions, e.g., pharmaceutically acceptable compositions, which include a therapeutic compound described herein, formulated together with a pharmaceutically acceptable carrier. As used herein, "pharmaceutically acceptable carrier" includes any and all solvents, dispersion media, isotonic and absorption delaying agents, and the like that are physiologically compatible.

The carrier can be suitable for intravenous, intramuscular, subcutaneous, parenteral, rectal, local, ophthalmic, topical, spinal or epidermal administration (e.g. by injection or infusion). As used herein, the term "carrier" means a diluent, adjuvant, or excipient with which a compound is administered. In some embodiments, pharmaceutical carriers can also be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. The carriers can be used in pharmaceutical compositions comprising the therapeutic compounds provided for herein.

The compositions and compounds of the embodiments provided for herein may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions. In some embodiments, the mode of administration is parenteral (e.g., intravenous, subcutaneous, intraperitoneal, intramuscular). In some embodiments, the therapeutic molecule is administered by intravenous infusion or injection. In another embodiment, the therapeutic molecule is administered by intramuscular or subcutaneous injection. In another embodiment, the therapeutic molecule is administered locally, e.g., by injection, or topical application, to a target site.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high therapeutic molecule concentration. Sterile injectable solutions can be prepared by incorporating the active compound (i.e., therapeutic molecule) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, a therapeutic compound can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of a therapeutic compound is 0.1-30 mg/kg, more preferably 1-25 mg/kg. Dosages and therapeutic regimens of the therapeutic compound can be determined by a skilled artisan. In certain embodiments, the therapeutic compound is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the therapeutic compound is administered at a dose from about 10 to 20 mg/kg every other week. The therapeutic compound can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the infusion rate of about 110 to 130 mg/m2 achieves a level of about 3 mg/kg. In other embodiments, the therapeutic compound can be administered by intravenous infusion at a rate of less than 10 mg/min, e.g., less than or equal to 5 mg/min to reach a dose of about 1 to 100 mg/m2, e.g., about 5 to 50 mg/m2, about 7 to 25 mg/m2, or, about 10 mg/m2. In some embodiments, the therapeutic compound is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions may include a "therapeutically effective amount" or a "prophylactically effective amount" of a therapeutic molecule. A "therapeutically effective amount" refers to an amount effective, at dosages and for periods of time necessary, to achieve the desired therapeutic result. A therapeutically effective amount of a therapeutic molecule may vary according to factors such as the disease state, age, sex, and weight of the individual, and the ability of the therapeutic compound to elicit a desired response in the individual. A therapeutically effective amount is also one in which any toxic or detrimental effects of a therapeutic molecule t is outweighed by the therapeutically beneficial effects. A "therapeutically effective dosage" preferably inhibits a measurable parameter, e.g., immune attack at least about 20%, more preferably by at least about 40%, even more preferably by at least about 60%, and still more preferably by at least about 80% relative to untreated subjects. The ability of a compound to inhibit a measurable parameter, e.g., immune attack, can be evaluated in an animal model system predictive of efficacy in transplant rejection or autoimmune disorders. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the embodiments is a kit comprising a therapeutic compound described herein. The kit can include one or more other elements including: instructions for use; other reagents, e.g., a label, a therapeutic agent, or an agent useful for chelating, or otherwise coupling, a therapeutic molecule to a label or other therapeutic agent, or a radioprotective composition; devices or other materials for preparing the a therapeutic molecule for administration; pharmaceutically acceptable carriers; and devices or other materials for administration to a subject.

In some embodiments, embodiments provided herein also include, but are not limited to:

1. A therapeutic compound comprising:
   i) a specific targeting moiety selected from:
      a) a donor specific targeting moiety which, e.g., preferentially binds a donor target; or
      b) a tissue specific targeting moiety which, e.g., preferentially binds target tissue of a subject; and
   ii) an effector binding/modulating moiety selected from:
      (a) an immune cell inhibitory molecule binding/modulating moiety (ICIM binding/modulating moiety);
      (b) an immunosuppressive immune cell binding/modulating moiety (IIC binding/modulating moiety); or
      (c) an effector binding/modulating moiety that, as part of a therapeutic compound, promotes an immuno-suppressive local microenvironment, e.g., by providing in the proximity of the target, a substance that inhibits or minimizes attack by the immune system of the target (SM binding/modulating moiety).

2. The therapeutic compound of embodiment 1, wherein the effector binding/modulating moiety directly binds and activ 3. The therapeutic compound of embodiment 2, wherein the effector binding/modulating moiety is an inhibitory immune checkpoint molecule.

4. The therapeutic compound of any of embodiments 1-3, wherein the effector binding/modulating moiety is expressed by an immune cell.

5. The therapeutic compound of embodiment 4, wherein the immune cell contributes to an unwanted immune response.

6. The therapeutic compound of embodiments 4 or 5, wherein the immune cell causes a disease pathology.

7. The therapeutic compound of embodiment 1, wherein the ability of the therapeutic molecule to agonize the molecule to which the effector binding/modulating binds is greater, e.g., 2, 5, 10, 100, 500, or 1,000 times greater, when the therapeutic compound is bound to a target through the targeting moiety than when the therapeutic compound is not bound to target through the targeting moiety.

8. The therapeutic compound of embodients 1-7, wherein when binding as a monomer (or binding when the therapeutic compound is not multimerized), to its cognate ligand, e.g., an inhibitory immune checkpoint molecule, does not agonize or substantially agonize, the cognate ligand.

9. The therapeutic compound of embodiments 1-8, wherein at a therapeutically effective dose of the therapeutic compound, there is significant, systemic agonization of the molecule to which the effector binding/modulating moiety binds.

10. The therapeutic compound of embodiments 1-9, wherein at a therapeutically effective dose of the therapeutic compound, the agonization of the molecule to which the effector binding/modulating moiety binds occurs substantially only at a target site to which the targeting moiety binds to.

11. The therapeutic compound of embodiments 1-9, wherein binding of the therapeutic compound to its cognate ligand, e.g., an inhibitory immune checkpoint molecule, does not inhibit, or does not substantially inhibit, binding of an endogenous counter ligand to the cognate ligand, e.g., an inhibitory immune checkpoint molecule.

12. The therapeutic compound of embodiments 1-11, wherein binding of the effector binding/modulating moiety to its cognate ligand, inhibits the binding of an endogenous counter ligand to the cognate ligand of the effector binding/modulating moiety by less than 60, 50, 40, 30, 20, 10, or 5%.

14. The therapeutic compound of embodiments 1-11, wherein binding of the effector binding/modulating moiety to the cognate ligand, results in substantially no antagonism of the cognate ligand of the effector binding/modulating molecule.

15. The therapeutic compound of embodiment 1, wherein the effector binding/modulating moiety comprises an ICIM binding/modulating moiety.

16. The therapeutic compound of embodiment 15, wherein the effector binding/modulating moiety comprises an ICIM binding/modulating moiety comprising an inhibitory immune checkpoint molecule ligand molecule.

17. The therapeutic compound of embodiment 16, wherein the inhibitory immune molecule counter-ligand molecule comprises a PD-L1 molecule.

18. The therapeutic compound of embodiment 15, wherein the ICIM is wherein the inhibitory immune molecule counter ligand molecule engages a cognate inhibitory immune checkpoint molecule selected from PD-1, KIR2DL4, LILRB1, LILRB, or CTLA-4.

19. The therapeutic compound of embodiment 18, wherein the ICIM is an antibody.

20. The therapeutic compound of embodiment 18, wherein the ICIM comprises an antibody that binds to PD-1, KIR2DL4, LILRB1, LILRB, or CTLA-4.

21. The therapeutic compound of embodiment 20, wherein the antibody is an antibody that binds to PD-1.

22. The therapeutic compound of embodiment 20, wherein the antibody is an antibody that binds to PD-1 and is a PD-1 agonist.

23. The therapeutic compound of embodiment 20, wherein the antibody is an antibody that binds to PD-1 and is a PD-1 agonist when tethered at a target site.

24. The therapeutic compound of embodiment 16, wherein the inhibitory immune molecule counter-ligand molecule comprises a HLA-G molecule.

25. The therapeutic compound of embodiment 15, wherein the ICIM is wherein the inhibitory immune molecule counter ligand molecule engages a cognate inhibitory immune checkpoint molecule selected from PD-1, KIR2DL4, LILRB1, LILRB, or CTLA-4.

26. The therapeutic compound of embodiment 15, wherein the inhibitory immune molecule counter ligand molecule engages a cognate inhibitory immune checkpoint molecule selected from Table 1.

27. The therapeutic compound of embodiment 15, wherein when binding as a monomer, to its cognate inhibitory immune checkpoint molecule, does not agonize or substantially agonize the inhibitory immune checkpoint molecule.

28. The therapeutic compound of embodiment 15, wherein the inhibitory immune molecule counter ligand has at least 60, 70, 80, 90, 95, 99, or 100% homology with a naturally occurring inhibitory immune checkpoint molecule ligand.

29 The therapeutic compound of embodiment 1, wherein the effector binding/modulating moiety comprises a ICIM binding/modulating moiety which comprises a functional antibody molecule to a cell surface inhibitory molecule.

30. The therapeutic compound of embodiment 1, wherein the cell surface inhibitory molecule is an inhibitory immune checkpoint molecule.

31. The compound of of embodiment 30, wherein the inhibitory immune checkpoint molecule is selected from PD-1, KIR2DL4, LILRB1, LILRB2, CTLA-4, or selected from Table 1.

32. The therapeutic compound of any of embodiments 1-31, wherein the level of systemic immune suppression at a therapeutically effective dose of the therapeutic compound, is less than that given by the standard of care with a systemic immune suppressant (if relevant), or is less than that given by an equimolar amount of free (not as a component of a therapeutic compound), effector binding/modulating molecule.

33. The therapeutic compound of embodiment 1-32, wherein the level of systemic immune activation, e.g., at a therapeutically effective dose of the therapeutic compound, is less than that given by a equimolar amount of free (not as a component of a therapeutic compound), effector binding/modulating molecule.

34. The therapeutic compound of any one of embodiments 1-33, further comprising a second effector binding/modulating moiety.

35. The therapeutic compound of embodiment 34, wherein the second effector binding/modulating moiety, binds a different target than the effector binding/modulating moiety.

36. The therapeutic compound embodiments 34 or 35, wherein the second effector binding/modulating moiety comprises a IIC binding/modulating moiety.

The therapeutic compound embodiments 34 or 35, wherein the second effector binding/modulating moiety comprises an SM binding/modulating moiety.

37. The therapeutic compound of embodiment 1, wherein the effector binding/modulating moiety comprises an IIC binding/modulating moiety.

38. The therapeutic compound of embodiment 1, wherein the effector binding/modulating moiety comprises an IIC binding/modulating moiety, which, increases, recruits or accumulates an immunosuppressive immune cell at the target site.

39. The therapeutic compound of embodiment 1, wherein the effector binding/modulating moiety comprises a cell surface molecule binder which binds or specifically binds, a cell surface molecule on an immunosuppressive immune cell.

40. The therapeutic compound of embodiment 1, wherein the effector binding/modulating moiety comprises a cell surface molecule ligand molecule that binds or specifically binds, a cell surface molecule on an immunosuppressive immune cell.

41. The therapeutic compound of embodiment 1, wherein the effector binding/modulating moiety comprises an antibody molecule that binds a cell surface molecule on an immunosuppressive immune cell.

42. The therapeutic compound of any of embodiments 38-41, wherein the immunosuppressive immune cell comprises a T regulatory cell, such as a a Foxp3+CD25+ T regulatory cell.

43. The therapeutic compound of any of embodiments 1-42, wherein the effector binding/modulating moiety binds GARP, and e.g., comprises an antibody molecule that binds GARP on GARP expressing immunosuppressive cells, e.g., Tregs.

44. The therapeutic compound of embodiment 1, wherein the effector binding/modulating moiety comprises an SM binding/modulating moiety.

45. The therapeutic compound of embodiment 44, wherein SM binding/modulating moiety promotes an immuno-suppressive local microenvironment.

46. The therapeutic compound of any of embodiments 44 and 45, wherein the effector molecule binding moiety increases the availability, e.g., by increasing the local concentration or amount, of a substance which inhibits immune cell function, e.g., a substance that inhibits the activation of an immune cell or the function of an activated immune cell.

47. The therapeutic compound of any of embodiments 44-46, wherein the effector molecule binding moiety binds and accumulate a soluble substance, e.g., an endogenous or exogenous substance, having immunosuppressive function.

48. The therapeutic compound of any of embodiments 44-47, wherein the effector molecule binding moiety decreases the availability, e.g., by decreasing the local concentration or amount, or sequestering, of a substance which promotes immune cell function, e.g., a substance that promotes the activation of an immune cell or the function of an activated immune cell.

49. The therapeutic compound of any one of embodiments 44-48, wherein SM binding/modulating moiety promotes an immuno-suppressive local microenvironment, e.g., by providing in the proximity of the target, a substance that inhibits or minimizes attack by the immune system of the target.

50. The therapeutic compound of any one of embodiments 44-49, wherein the SM binding/modulating moiety comprises a molecule that inhibits or minimizes attack by the immune system of the target.

51. The therapeutic compound any one of embodiments 44-50, wherein the SM binding/modulating moiety binds and/or accumulate a soluble substance, e.g., an endogenous or exogenous substance having immunosuppressive function.

52. The therapeutic compound any one of embodiments 44-51, wherein the SM binding/modulating moiety binds and/or inhibits, sequesters, degrades or otherwise neutralizes a substance, e.g., a soluble substance, typically and endogenous soluble substance, that promotes immune attack.

53. The therapeutic compound any one of embodiments 44-52, wherein the effector molecule binding moiety decreases the availability of ATP or AMP.

54. The therapeutic compound any one of embodiments 44-53, wherein SM binding/modulating moiety binds, or comprises, a substance, e.g., CD39 or CD73, that depletes a component that promotes immune effector cell function, e.g., ATP or AMP.

55. The therapeutic compound any one of embodiments 44-54, wherein the SM binding/modulating moiety comprises a CD39 molecule.

56. The therapeutic compound any one of embodiments 44-54, wherein the SM binding/modulating moiety comprises a CD73 molecule.

57. The therapeutic compound any one of embodiments 44-54, wherein the SM binding/modulating moiety comprises an anti-CD39 molecule.

58. The therapeutic compound any one of embodiments 44-54, wherein the SM binding/modulating moiety comprises an anti-CD73 antibody molecule.

59. The therapeutic compound any one of embodiments 44-54, wherein the effector molecule binding moiety comprises an immune-suppressive substance, e.g. a fragment an immunosuppressive protein.

60. The therapeutic compound any one of embodiments 44-54, wherein SM binding/modulating moiety comprises alkaline phosphatase molecule.

61. The therapeutic compound of embodiment 1, wherein the compound has the formula from N-terminus to C-terminus:

R1—Linker Region A—R2 or R3—Linker Region B—R4, wherein,
R1, R2, R3, and R4, each independently comprises an effector binding/modulating moiety, e.g., an ICIM binding/modulating moiety, an IIC binding/modulating moiety, or an SM binding/modulating moiety; a specific targeting moiety; or is absent; provided that an effector binding/modulating moiety and a specific targeting moiety are present.

62. The therapeutic compound of embodiment 61, wherein each of Linker Region A and Linker Region B comprises an Fc region.

63. The therapeutic compound of embodiment 61, wherein one of R1 and R2 is anti-PD-1 antibody and one of R1 and R2 is an anti-MAdCAM antibody.

64. The therapeutic compound of embodiment 61, wherein one of R1 is anti-PD-1 antibody and one R2 is an anti-MAdCAM antibody.

65. The therapeutic compound of embodiment 61, wherein one of R1 is anti-MAdCAM antibody and one R2 is an anti-PD-1 antibody.

66. The therapeutic compound of embodiment 61, wherein one of R3 and R4 is anti-PD-1 antibody and one of R3 and R4 is an anti-MAdCAM antibody.

67. The therapeutic compound of embodiment 61, wherein one of R3 is anti-PD-1 antibody and one R4 is an anti-MAdCAM antibody.
68. The therapeutic compound of embodiment 61, wherein one of R3 is anti-MAdCAM antibody and one R4 is an anti-PD-1 antibody.
69. The therapeutic compound of any of embodiments 61-68, wherein the linker is absent.
70. The therapeutic compound of any of embodiments 61-68, wherein the linker is a Fc region.
71. The therapeutic compound of any of embodiments 61-68, wherein the linker is a glycine/serine linker, such as 1, 2, 3, 4, or 5 repeats of GGGGS (SEQ ID NO: 6).
72. The therapeutic compound of any of embodiments 61-68, wherein the linker comprises a Fc region and a glycine/serine linker, such as 1, 2, 3, 4, or 5 repeats of GGGGS (SEQ ID NO: 6).
73. The therapeutic compound of any of embodiments 61-72, wherein the PD-1 antibody is a PD-1 agonist.
74. The therapeutic compound of embodiment 61, wherein:
R1 and R3 independently comprise a functional anti-PD-1 antibody molecule (an agonist of PD-1); and R2 and R4 independently comprise specific targeting moieties, e.g., scFv molecules against a tissue antigen.
75. The therapeutic compound of any of embodiments 73 and 74, wherein:
R1 and R3 independently comprise specific targeting moieties, e.g., an anti-tissue antigen antibody; and R2 and R4 independently comprise a functional anti-PD-1 antibody molecule (an agonist of PD-1).
76. The therapeutic compound of any of embodiments 73 and 74, wherein:
R1, R2, R3 and R4 each independently comprise: an SM binding/modulating moiety which modulates, e.g., binds and inhibits, sequesters, degrades or otherwise neutralizes a substance, e.g., a soluble molecule that modulates an immune response, e.g., ATP or AMP, e.g., a CD39 molecule or a CD73 molecule; a specific targeting moiety; or is absent;
provided that an SM binding/modulating moiety and a specific targeting moiety are present.
77. The therapeutic compound of embodiment 61, wherein:
R1 and R3 independently comprise a CD39 molecule or a CD73 molecule; and
R2 and R4 independently comprise specific targeting moieties, e.g., scFv molecules against a tissue antigen.
78. The therapeutic compound of embodiment 77, wherein:
R1 and R3 each comprises a CD39 molecule; and
R2 and R4 independently comprise specific targeting moieties, e.g., scFv molecules against a tissue antigen.
79. The therapeutic compound of embodiments 61 or 77, wherein:
R1 and R3 each comprises a CD73 molecule; and
R2 and R4 independently comprise specific targeting moieties, e.g., scFv molecules against a tissue antigen.
80. The therapeutic compound of embodiment 61, wherein:
one of R1 and R3 comprises a CD39 molecule and the other comprises a CD73 molecule; and
R2 and R4 independently comprise specific targeting moieties, e.g., scFv molecules against a tissue antigen.
81. The therapeutic compound of embodiment 61, wherein:
R1, R2, R3 and R4 each independently comprise: an HLA-G molecule; a specific targeting moiety; or is absent;
provided that an HLA-G molecule and a specific targeting moiety are present.

82. The therapeutic compound of embodiments 61 or 81, wherein:
R1 and R3 each comprise an HLG-A molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
83. The therapeutic compound of any of embodiments 81 and 82, wherein:
R1 and R3 each comprise an agonistic anti-LILRB1 antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
84. The therapeutic compound of any of embodiments 81 and 82, wherein:
R1 and R3 each comprise an agonistic anti-KIR2DL4 antibody molecule; and
R2 and R4 independently comprise specific targeting moieties, e.g., scFv molecules against a tissue antigen.
In some embodiments, Linker A and Linker B comprise Fc moieties (e.g., self pairing Fc moieties or Fc moieties that do not, or do not substantially self pair).
85. The therapeutic compound of any of embodiments 81-84, wherein:
R1 and R3 each comprise an agonistic anti-LILRB2 antibody molecule; and
R2 and R4 independently comprise specific targeting moieties, e.g., scFv molecules against a tissue antigen.
86. The therapeutic compound of any of embodiments 81-84, wherein:
R1 and R3 each comprise an agonistic anti-NKG2A antibody molecule; and
R2 and R4 independently comprise specific targeting moieties, e.g., scFv molecules against a tissue antigen.
87. The therapeutic compound of any of embodiments 81-84, wherein:
one of R1 and R3 comprises a first moiety chosen from, and the other comprises a different moiety chosen from: an antagonistic anti-LILRB1 antibody molecule, an agonistic anti-KR2DL4 antibody molecule, and an agonistic anti-NKG2A antibody molecule; and
R2 and R4 independently comprise specific targeting moieties, e.g., scFv molecules against a tissue antigen.
88. The therapeutic compound of any of embodiments 81-84, wherein:
one of R1 and R3 comprises an antagonistic anti-LILRB1 antibody molecule and the other comprises an agonistic anti-KR2DL4 antibody molecule; and
R2 and R4 independently comprise specific targeting moieties, e.g., scFv molecules against a tissue antigen.
89. The therapeutic compound of any of embodiments 81-84, wherein:
one of R1 and R3 comprises an antagonistic anti-LILRB1 antibody molecule and the other comprises an agonistic anti-NKG2A antibody molecule; and
R2 and R4 independently comprise specific targeting moieties, e.g., scFv molecules against a tissue antigen.
90. The therapeutic compound of any of embodiments 81-84, wherein:
one of R1, R2, R3 and R4 comprises an anti-BCR antibody molecule, e.g., an antagonistic anti-BCR antibody molecule, one comprises an anti FCRL antibody molecule, and one comprises specific targeting moiety.

91. The therapeutic compound of embodiment 90, wherein: the anti-FCRL molecule comprises: an anti-FCRL antibody molecule, e.g., an agonistic anti-FCRL antibody molecule, directed to FCRL1, FCRL2, FCRL3, FCRL4, FCRL5, or FCRL6.

92. The therapeutic compound of any of embodiments 81-84, wherein:
R1, R2, R3 and R4 each independently comprise:
i) an effector binding/modulating moiety, e.g., an ICIM binding/modulating moiety, an IIC binding/modulating moiety, or an SM binding/modulating moiety, that minimizes or inhibits T cell activity, expansion, or function (a T cell effector binding/modulating moiety);
ii) an effector binding/modulating moiety, e.g., an ICIM binding/modulating moiety, an IIC binding/modulating moiety, or an SM binding/modulating moiety, that minimizes or inhibits B cell activity, expansion, or function (a B cell effector binding/modulating moiety);
iii) a specific targeting moiety; or
iv) is absent; provided that, a T cell effector binding/modulating moiety, a B cell effector binding/modulating moiety, and a specific targeting moiety are present.

93. The therapeutic compound of embodiment 92, wherein: one of R1, R2, R3, and R4 comprises an agonistic anti-PD-1 antibody and one comprises an HLA-G molecule.

94. The therapeutic compound embodiments 92-93, wherein:
one of R1, R2, R3, and R4 comprises an SM binding/modulating moiety, e.g., a CD39 molecule or a CD73 molecule.

95. The therapeutic compound of any of embodiments 92-94, wherein:
one of R1, R2, R3, and R4 comprises an entity that binds, activates, or maintains, a regulatory immune cell, e.g., a Treg cell or a Breg cell.

96. The therapeutic compound of any of embodiments 92-95, wherein:
one of R1, R2, R3, and R4 comprises an agonistic anti-PD-1 antibody or one comprises an HLA-G molecule.

97. The therapeutic compound of embodiment 96, wherein: one of R1, R2, R3, and R4 comprises an agonistic anti-PD-1 antibody, one comprises an HLA-G molecule, and one comprises CD39 molecule or a CD73 molecule.

98. The therapeutic compound of any of embodiments 1-97, wherein the effector binding/modulating moiety comprises a polypeptide.

99. The therapeutic compound of any of embodiments 1-98, wherein the effector binding/modulating moiety comprises a polypeptide having at least 5, 10, 20, 30, 40, 50, 150, 200 or 250 amino acid residues.

100. The therapeutic compound of any of embodiments 1-99, wherein the effector binding/modulating moiety has a molecular weight of 5, 10, 15, 20, or 40 Kd.

101. The therapeutic compound of any of embodiments 1-100, wherein the effector binding/modulating moiety does not comprise an inhibitor of the expression of apolipoprotien CIII, protein kinase A, Src kinase, or Beta1 integrin.

102. The therapeutic compound of any of embodiments 1-100, wherein the effector binding/modulating moiety does not comprise an inhibitor of the activity of apolipoprotien CIII, protein kinase A, Src kinase, or Beta1 integrin.

103. The therapeutic compound of any of embodiments 1-101, wherein the therapeutic compound does not specifically target a tissue selected from lung, skin, pancreas, retina, prostate, ovary, lymph node, adrenal gland, liver or gut tissue.

104. The therapeutic compound of any of embodiments 1-101, wherein the therapeutic compound does not specifically target tubular cells, e.g., proximal tubular epithelial cells 105. The therapeutic compound of any of embodiments 1-101, wherein the therapeutic compound does not specifically target TIE-2, APN, TEM4, TEM6, ICAM-1, nucleolin P2Z receptor, Trk-A, FLJ10849, HSPA12B, APP, or OX-45.

106. The therapeutic compound of any of embodiments 1-101, wherein the therapeutic compound does not specifically target a luminally expressed protein.

107. The therapeutic compound of any of embodiments 1-101, wherein the donor target does not comprise a heart specific target.

108. The therapeutic compound of any of embodiments 1-101, wherein the therapeutic compound does not specifically target lung tissue.

109. The therapeutic compound of any of embodiments 1-101, wherein the therapeutic compound does not specifically target kidney tissue.

110. The therapeutic compound of any of embodiments 1-101, wherein the therapeutic compound does not specifically pancreas lung tissue.

111. The therapeutic compound of any of embodiments 1-101, wherein the therapeutic compound does not specifically target gut tissue.

112. The therapeutic compound of any of embodiments 1-101, wherein the therapeutic compound does not specifically target prostate tissue.

113. The therapeutic compound of any of embodiments 1-101, wherein the therapeutic compound does not specifically target brain tissue.

114. The therapeutic compound of any of embodiments 1-101, wherein the therapeutic compound does not specifically target CD71.

115. The therapeutic compound of any of embodiments 1-101, wherein the therapeutic compound does not specifically target CD90.

116. The therapeutic compound of any of embodiments 1-101, wherein the therapeutic compound does not specifically target MAdCAM.

117. The therapeutic compound of any of embodiments 1-101, wherein the therapeutic compound does not specifically target albumin.

118. The therapeutic compound of any of embodiments 1-101, wherein the therapeutic compound does not specifically target carbonic anhydrase IV.

119. The therapeutic compound of any of embodiments 1-101, wherein the therapeutic compound does not specifically target ZG16-p.

120. The therapeutic compound of any of embodiments 1-101, wherein the therapeutic compound does not specifically target dipeptidyl peptidase IV.

121. The therapeutic compound of any of embodiments 1-101, wherein the therapeutic compound does not specifically target the luminal surface of a vascular endothelial cell membrane.

121. The therapeutic compound of any of embodiments 1-101, wherein the therapeutic compound does not specifically target heart tissue.

122. The therapeutic compound of any of embodiments 1-101, wherein the therapeutic compound does not specifically target a tumor, solid tumor, or the vascular of a solid tumor.

123. The therapeutic compound of any of embodiments 1-101, wherein the therapeutic compound does not specifically target skin tissue.

124. The therapeutic compound of any of embodiments 1-101, wherein the therapeutic compound does not specifically target epidermal tissue.
125. The therapeutic compound of any of embodiments 1-101, wherein the therapeutic compound does not specifically target the basement membrane.
126. The therapeutic compound of any of embodiments 1-101, wherein the therapeutic compound does not specifically target a Dsg polypeptide.
127. The therapeutic compound of any of embodiments 1-101, wherein the therapeutic compound does not specifically target Dsg1.
128. The therapeutic compound of any of embodiments 1-101, wherein the therapeutic compound does not specifically target Dsg3.
129. The therapeutic compound of any of embodiments 1-101, wherein the therapeutic compound does not specifically target BP180.
130. The therapeutic compound of any of embodiments 1-101, wherein the therapeutic compound does not specifically target desmoglein.
131. The therapeutic compound of any of embodiments 1-101, wherein the therapeutic compound does not comprise a complement modulator, e.g., a compliment inhibitor, such as, but not limited to, those described in U.S. Pat. No. 8,454,963, which is hereby incorporated by reference in its entirety.
133. The therapeutic compound of any of embodiments 1-101, wherein the therapeutic compound does not comprise an imaging agent.
134. The therapeutic compound of any of embodiments 1-101, wherein the therapeutic compound does not comprise an imaging agent selected from the group of: a radioactive agent, a radioisotope, a radiopharmaceutical, a contrast agent, a nanoparticle; an enzyme, a prosthetic group, a fluorescent material, a luminescent material, and a bioluminescent material, such as, but not limited to, those described in U.S. Pat. No. 8,815,235, which is hereby incorporated by reference in its entirety.
135. The therapeutic compound of any of embodiments 1-101, wherein the therapeutic compound does not comprise a radionuclide, such as, but not limited to, those described in U.S. Pat. No. 6,232,287, which is hereby incorporated by reference in its entirety.
136. The therapeutic compound of any of embodiments 1-101, which is not internalized by a donor cell to which it binds.
137. The therapeutic compound of any of embodiments 1-101, wherein the therapeutic compound does not enter the cell which is targeted by the specific targeting moiety.
138. The therapeutic compound of any of embodiments 1-101, wherein the therapeutic compound does not kill the cell which is targeted by the specific targeting moiety.
139. The therapeutic compound of any of embodiments 1-101, wherein the therapeutic compound does not enter the cell to which the effector binding/modulating moiety binds.
140. The therapeutic compound of any of embodiments 1-101, wherein the therapeutic compound does not kill the cell to which the effector binding/modulating moiety binds.
141. The therapeutic compound of any of embodiments 1-101, wherein the therapeutic compound does not comprise an autoantigenic peptide or polypeptide.
142. The therapeutic compound of any of embodiments 1-101, wherein the therapeutic compound does not comprise an autoantigenic peptide or polypeptide, e.g., does not comprise a peptide or polypeptide against which the subject has autoantibodies.
143. The therapeutic compound of any of embodiments 1-101, wherein the therapeutic compound does not comprise an antibody molecule derived from a mammal, e.g., a human, having an autoimmune disorder.
144. The therapeutic compound of any of embodiments 1-101, wherein the therapeutic compound does not comprise an antibody molecule derived from a mammal, e.g., a human, having acute mucocutaneous PV.
145. The therapeutic compound of any of embodiments 1-101, wherein the therapeutic compound does not comprise an antibody molecule derived from a mammal, e.g., a human, having Goodpasture's Disease
146. The therapeutic compound of any of embodiments 1-101, wherein the therapeutic compound does not comprise an antibody molecule derived from a mammal, e.g., a human, having pemphigus vulgaris.
141. The therapeutic compound of any of embodiments 1-146, comprising a donor specific targeting moiety.
142. The therapeutic compound of any of embodiments 141, that localizes preferentially to an implanted donor tissue, as opposed to tissue of a recipient.
143. The therapeutic compound of embodiments 141-142, wherein, the donor specific targeting moiety provides site-specific immune privilege for a transplant tissue, e.g., an organ, from a donor.
144. The therapeutic compound of embodiments 141-143, wherein the donor specific targeting moiety binds to a product, e.g., a polypeptide, of an allele present at a locus in the donor, which allele is not present at the locus in the recipient
145. The therapeutic compound of any of embodiments 141-144, wherein, the donor specific targeting moiety preferentially binds to an allele of a gene expressed on donor tissue, e.g., a transplant tissue, e.g., an organ, as compared with an allele of the gene expressed on subject tissue.
146. The therapeutic compound of embodiments 141-145, wherein, the donor specific targeting moiety has a binding affinity for an allele of a gene expressed on donor tissue, e.g., a transplant tissue, e.g., an organ, which is at least 2, 4, 5, 10, 50, 100, 500, 1,000, 5,000, or 10,000 fold greater than its affinity for an allele of the gene expressed on subject tissue.
147. The therapeutic compound of any of embodiments 141-146, wherein the donor specific targeting moiety binds to the product, e.g., a polypeptide, of an allele present at a locus in the donor, which allele is not present at the locus in the recipient.
148. The therapeutic compound of any one of embodiments 141-147, wherein the binding is sufficiently specific that, e.g., at a clinically effective dose of the therapeutic compound, unwanted, substantial, or clinically unacceptable, systemic immune suppression occurs.
149. The therapeutic compound of any one of embodiments 141-148, wherein the therapeutic compound accumulates at the target site, e.g., binding of the donor specific targeting moiety to results in accumulation of the therapeutic compound at the target site.
150. The therapeutic compound of any one of embodiments 141-149, wherein the donor specific targeting moiety binds a product of an allele of a locus selected from Table 2, e.g., the HLA locus, e.g., the HLA-A, HLA-B, HLA-C, HLA-DP, HLA-DQ or HLA-DR locus, which allele is present in the donor but not the recipient. HLA-A, HLA-B, HLA-C, HLA-DP, HLA-DQ or HLA-DR locus.
151. The therapeutic compound of any one of embodiments 141-150, wherein the donor specific targeting moiety binds an allele of HLA A, an allele of HLA-B, an allele of HLA-C, an allele of HLA-DP, an allele of HLA-, or an allele of HLA-.

152. The therapeutic compound of any one of embodiments 141-151, wherein the therapeutic compound is suitable for treating a subject that has, will have, or is in need of, a transplant.

153. The therapeutic compound of embodiment 152, wherein the transplant comprises all or part of an organ, e.g., a liver, kidney, heart, pancreas, thymus, skin or lung.

154. The therapeutic compound of any one of embodiments 141-153, wherein the donor specific targeting moiety comprises an antibody molecule.

155. The therapeutic compound of any one of embodiments 141-153, wherein the donor specific targeting moiety comprises a target specific binding polypeptide, or a target ligand binding molecule.

156. The therapeutic compound of any one of embodiments 1-155, comprising a tissue specific targeting moiety.

157. The therapeutic compound of embodiment 156, wherein the tissue specific targeting moiety is a molecule that specifically binds to MAdCAM.

158. The therapeutic compound of embodiment 156, wherein the tissue specific targeting moiety is an antibody that specifically binds to MAdCAM.

159. The therapeutic compound of any one of embodiments, 156-158, wherein the therapeutic compound is suitable for treating a subject having, or is at risk, or elevated risk, for having, an autoimmune disorder, e.g., an autoimmune disorder described herein.

160. The therapeutic compound of any of embodiments 156-159, wherein the therapeutic compound accumulates at the target site, e.g., binding of the tissue specific targeting moiety results in accumulation of the therapeutic compound at the target site.

161. The therapeutic compound of any of embodiments 156-160, wherein the therapeutic compound which localizes, preferentially to a target tissue, as opposed to other tissue of a subject.

162. The therapeutic compound of any of embodiments 156-161, wherein the therapeutic compound provides site-specific immune privilege for a subject target tissue, e.g., a target tissue undergoing, or at risk, or elevated risk, for, unwanted immune attack, e.g., in an autoimmune disorder.

163. The therapeutic compound of any of embodiments 156-161, wherein the tissue specific targeting moiety, as a component of the therapeutic compound, preferentially binds a subject target tissue undergoing unwanted immune attack, e.g., in an autoimmune disorder.

164. The therapeutic compound of any of embodiments 156-163, wherein a tissue specific targeting moiety binds to the product, e.g., a polypeptide, which is not present outside the target tissue, or is present at sufficiently low levels that, at therapeutic concentrations of therapeutic molecule, unacceptable levels of immune suppression are absent or substantially absent.

165. The therapeutic compound of any of embodiments 156-164, wherein, the tissue specific targeting moiety binds a product, or site on a product, which is more abundant in target tissue than in non-target tissue.

166. The therapeutic compound of any of embodiments 156-165, wherein, therapeutic compound binds a product, or a site on a product, that is present or expressed substantially exclusively on target tissue.

167 The therapeutic compound of any of embodiments 156-166, wherein the product, or site on a product, to which the specific targeting moiety binds, is sufficiently limited to the target tissue, that at therapeutically effective level of therapeutic compound, the subject does not suffer an unacceptable level, e.g., a clinically significant level, of systemic immune suppression.

168. The therapeutic compound of any of embodiments 156-167, wherein the therapeutic compound, preferentially binds to a target tissue or target tissue antigen, e.g., has a binding affinity for the target tissue or antigen that is greater for target antigen or tissue, e.g., at least 2, 4, 5, 10, 50, 100, 500, 1,000, 5,000, or 10,000 fold greater, than its affinity for than for non-target tissue or antigen present outside the target tissue.

169. The therapeutic compound of any of embodiments 156-168, wherein the tissue specific targeting moiety binds to a product, e.g., a polypeptide product, or site on a product, present at a preselected site, e.g., a site of unwanted immune response in an autoimmune disorder.

170. The therapeutic compound of any of embodiments 156-169, wherein therapeutic compound is suitable for the treatment of a subject having, or at risk, or elevated risk, for having, type 1 diabetes.

171. The therapeutic compound of any of embodiments 156-170, wherein the target tissue comprises pancreatic tissue, e.g., pancreatic islets or pancreatic beta cells, gut tissue (e.g. gut endothelial cells), kidney tissue (e.g. kidney epithelial cells), or liver tissue (e.g. liver epithelial cells).

172. The therapeutic compound of any of embodiments 156-171, wherein the effector binding/modulating moiety or targeting moiety binds a polypeptide selected from those described herein, such as those listed in Table 3, e.g., SEZ6L2, LRP11, DISP2, SLC30A8, FXYD2, TSPAN7, or TMEM27.

173. The therapeutic compound of any of embodiments 156-168, wherein therapeutic compound is suitable for the treatment of a subject having, or at risk, or elevated risk, for having, multiple sclerosis.

174. The therapeutic compound of embodiment 173, wherein the target tissue comprises CNS tissue, myelin sheath, or myelin sheath of oligodendrocytes.

175. The therapeutic compound of any of embodiments 173-174, wherein the effector binding/modulating moiety or targeting moiety binds a polypeptide selected from those described herein and including, but not limited to, Table 3, e.g., MOG, PLP, or MBP.

176. The therapeutic compound of any of embodiments 156-168, wherein therapeutic compound is suitable for the treatment of a subject having, or at risk, or elevated risk, for having, cardiomyositis.

177. The therapeutic compound of embodiment 176, wherein the target tissue comprises cardiomyocytes, monocytes, macrophages, or myeloid cells.

178. The therapeutic compound of embodiments 176-177, wherein the effector binding/modulating moiety binds or the targeting moiety a polypeptide as described herein, including, but not limited to those selected from Table 3, e.g., SIRPA (CD172a).

179. The therapeutic compound of any of embodiments 156-168, wherein therapeutic compound is suitable for the treatment of a subject having, or at risk, or elevated risk, for having, inflammatory bowel disease, autoimmune hepatitis (AIH); Primary Sclerosing Cholangitis (PSC); Primary Biliary Sclerosis; (PBC); or transplant.

180. The therapeutic compound of any of embodiments 156-168, wherein the subject with has, is at risk or elevated risk for having Crohn's disease or ulcerative colitis.

181. The therapeutic compound of embodiments 179 or 180, wherein the target tissue comprises gut cells, such as gut epithelial cells or liver cells, such as liver epithelial cells.

182. The therapeutic compound of embodiments 179-181, wherein the effector binding/modulating moiety binds a polypeptide as described herein, including, but not limited to those selected from Table 3, e.g., PD-1. 182. The therapeutic compound of embodiments 179-181, wherein the targeting moiety binds a polypeptide as described herein, including, but not limited to MAdCAM.

183. The therapeutic compound of any of embodiments 156-168, wherein therapeutic compound is suitable for the treatment of a subject having, or at risk, or elevated risk, for having, rheumatoid arthritis.

184. The therapeutic compound of embodiment 183, wherein the target tissue comprises cardiomyocytes, monocytes, macrophages, or myeloid cells.

185. The therapeutic compound of embodiments 183 or 184, wherein the effector binding/modulating moiety or targeting moiety binds a polypeptide selected from Table 3, e.g., SIRPA (CD172a).

186. The therapeutic compound of any of embodiments 156-185, wherein the tissue specific targeting moiety comprises an antibody molecule.

187. The therapeutic compound of any of embodiments 156-185, wherein the tissue specific targeting moiety comprises a target specific binding polypeptide, or a target ligand binding molecule.

188. The therapeutic compound of any of embodiments 156-185, wherein the tissue specific targeting moiety comprises a target specific binding polypeptide binds to MAdCAM.

189. The therapeutic compound of any of embodiments 1-188, wherein the therapeutic compound binds a cell surface molecule of an immune effector cell, e.g., a T cell, B cell, NK cell, or other immune cell, which cell propagates a pro-immune response.

190. The therapeutic compound of any of embodiments 1-189, wherein the therapeutic compound reduces the ability of an immune effector cell, e.g., a T cell, B cell, NK cell, or other immune cell, to propagate a pro-immune response.

191. The therapeutic compound of any of embodiments 1-190, wherein the specific targeting moiety targets a mammalian target, e.g., a mammalian polypeptide, and the effector binding/modulating moiety binds/modulates a mammalian immune component, e.g., a human immune cell, e.g., a mammalian B cell, T cell, or macrophage.

192. The therapeutic compound of any of embodiments 1-192, wherein the specific targeting moiety targets a human target, e.g., a human polypeptide, and the effector binding/modulating moiety binds/modulates a human immune component, e.g., a human immune cell, e.g., a ahuman B cell, T cell, or macrophage.

193. The therapeutic compound of any of embodiments 1-193, wherein the therapeutic compound is configured for use in a human.

194. The therapeutic compound of any of embodiments 1-191, wherein the therapeutic compound is configured for use in a non-human mammal.

195. The therapeutic compound of any of embodiments 1-194, wherein the therapeutic compound, e.g., the effector binding/modulating moiety, comprises a PD-1 agonist.

196. A method of treating a subject with inflammatory bowel disease, the method comprising administering a therapeutic compound of any of embodiments 1-195 to the subject to treat the inflammatory bowel disease.

197. The method of embodiment 196, wherein the subject with inflammatory bowel disease has Crohn's disease.

198. The method of embodiment 196, wherein the subject with inflammatory bowel disease has ulcerative colitis.

199. A method of treating a subject with auto-immune hepatitis, the method comprising administering a therapeutic compound of any of embodiments 1-195 to the subject to treat the auto-immune hepatitis.

200. A method of treating primary sclerosing cholangitis the method comprising administering a therapeutic compound of any of embodiments 1-195 to the subject to treat the primary sclerosing cholangitis.

201. A method of treating Type 1 diabetes the method comprising administering a therapeutic compound of any of embodiments 1-195, thereby treating the subject to treat the Type 1 diabetes.

202. A method of treating a transplant subject comprising administering a therapeutically effective amount of a therapeutic compound of any of embodiments 1-195 to the subject, thereby treating a transplant (recipient) subject.

203. A method of treating GVHD in a subject having a transplanted a donor tissue comprising administering a therapeutically effective amount of a therapeutic compound of any of embodiments 1-195 to the subject.

204. The method of embodiment 203, wherein the therapeutic compound is administered to the subject: prior to receiving the transplant; prior to developing a symptom of GVHD; after or concurrent with receiving the transplant; or after or concurrent with developing a symptom of GVHD.

205. A method of treating a subject having, or at risk, or elevated risk, for having, an autoimmune disorder, comprising administering a therapeutically effective amount of a therapeutic compound of any embodiments 1-195, thereby treating the subject.

206. The method of embodiment 205, wherein the subject has received, will receive, or is in need of, allograft donor tissue.

207. The method of any of embodiments 205-206, wherein the donor tissue comprises a solid organ, e.g., a liver, kidney, heart, pancreas, thymus, or lung.

208. The method of any of embodiments 205-206, wherein the donor tissue comprises all or part of an organ, e.g., a liver, kidney, heart, pancreas, thymus, or lung.

209. The method of any of embodiments 205-206, wherein the donor tissue comprises skin.

210. The method of any of embodiments 205-206, wherein the donor tissue does not comprises skin.

211. The method of any of embodiments 205-210, wherein the donor tissue presents or expresses a product of an allele of a locus locus, which allele is not present or expressed in the subject.

212. The method of any of embodiments 205-210, wherein the donor tissue presents or expresses a product of an allele of a locus selected from Table 2, e.g., the HLA locus, e.g., the HLA-A, HLA-B, HLA-C, HLA-DP, HLA-DQ or HLA-DR locus, which allele is not present or expressed in the subject.

213 The method of any of embodiments 205-212, comprising introducing the transplant tissue into the subject.

214. The method of any of embodiments 196-213, comprising monitoring the subject for immune cell inactivation (e.g., to monitor unwanted agonization of an immune inhibitory checkpoint molecule) at a site distant from the target site, e.g., in the peripheral circulation or the lymphatic system.

215. The method of any of embodiments 196-214, comprising monitoring the subject for immune cell activation (e.g., to monitor unwanted antagonization of an immune inhibitory checkpoint molecule) at a site distant from the target site, e.g., in the peripheral circulation or the lymphatic system.

216. The method of any of embodiments 196-215, wherein responsive to the result of monitoring, selecting a course of treatment for the subject, e.g., increasing the dose of the therapeutic compound, decreasing the dose of the therapeutic compound, continuing treatment with the therapeutic compound without a change in dose.

217. The method of any of embodiments 196-216, comprising administering the compound of embodiments 1-195, to the recipient.

218. The method of any of embodiments 196-216, wherein administering comprises systemic administration, e.g., to the peripheral circulatory system.

219. The method of any of embodiments 196-216, wherein administering comprises local administration, e.g., to the target tissue, the donor tissue or the site of at which the target tissue or the donor tissue is, or will be located.

220. The method of any of embodiments 219, comprising administering the therapeutic compound to the recipient prior to introduction of the donor tissue into the recipient.

221. The method of any of embodiments 219, comprising administering the therapeutic compound, to the recipient after introduction of the donor tissue into the recipient.

222. The method of any of embodiments 213, comprising administering the therapeutic compound to the recipient concurrent with introduction of the donor tissue into the recipient.

223. The method of embodiment 213, comprising contacting the therapeutic compound with the donor tissue prior to introduction of the donor tissue into the recipient.

224. The method of any of embodiments 213, comprising providing the therapeutic compound to the subject, wherein the transplant tissue has been contacted with therapeutic compound prior to introduction into the subject.

225. The method of any of embodiments 213, comprising contacting the therapeutic compound with the donor tissue after introduction of the donor tissue into the recipient, e.g., by local administration to the donor tissue.

226. The method of any of embodiments 196-226, comprising administering a therapeutic compound as provided for herein such that therapeutic levels are present for at least 1, 5, 10, 14, or 28 days, for example, consecutive or non-consecutive days.

227. The method of any of embodiments 196-226, wherein the subject does not receive a non-targeted immune suppressive agent.

228. The method of any of embodiments 196-226, wherein for the subject has not received a non-targeted immune suppressive agent for at least 1, 15, 30, 60, or 90 days prior to the initial administration of the therapeutic compound.

229. The method of any of embodiments 213, wherein the subject has not received a non-targeted immune suppressive agent for at least 1, 15, 30, 60, or 90 days prior to introduction of the transplant tissue.

230. The method of any of embodiments 196-229, wherein the subject does not receive a non-targeted immune suppressive agent for at least 1, 15, 30, 60, 90, or 180 days after the initial administration of the therapeutic compound.

231. The method of any of embodiments 196-229, wherein the subject does not receive a non-targeted immune suppressive agent for at least 1, 15, 30, 60, 90, or 180 days after introduction of the transplant tissue.

232. The method of any of embodiments 196-231, comprising administering a non-targeted immune suppressive agent to the subject.

233. The method of any of embodiments 196-232, wherein for the subject receives a non-targeted immune suppressive agent for at least 1, 15, 30, 60, or 90 days prior to the initial administration of the therapeutic compound.

234. The method of embodiment 213, wherein the subject receives a non-targeted immune suppressive agent for at least 1, 15, 30, 60, or 90 days prior to introduction of the transplant tissue.

235. The method of embodiment 234, wherein the subject receives a non-targeted immune suppressive agent for at least 1, 15, 30, 60, 90 or 180 days after the initial administration of the therapeutic compound.

236. The method of any of embodiments 196-235, wherein the subject receives a non-targeted immune suppressive agent for at least 1, 15, 30, 60, 90 or 180 days after introduction of the transplant tissue.

237. The method of any of embodiments 196-235, wherein for the subject receives a non-targeted immune suppressive agent prior to the initial administration of the therapeutic compound but for no more than 1, 15, 30, 60, 90 or 180 days.

238. The method of embodiment 213, wherein the subject receives a non-targeted immune suppressive agent prior to introduction of the transplant tissue but for no more than 1, 15, 30, 60, 90 or 180 days.

239. The method of any of embodiments 196-238, wherein the subject receives a non-targeted immune suppressive agent after the initial administration of the therapeutic compound but for no more than 1, 15, 30, 60, 90 or 180 days.

240. The method of embodiment 213, wherein the subject receives a non-targeted immune suppressive agent after introduction of the transplant tissue but for no more than 1, 15, 30, 60, 90 or 180 days.

241. The method of embodiment 213, wherein the subject is monitored for rejection of the transplant tissue.

242. The method of any of embodiments 196-242, a dosage of a non-targeted immune suppressive agent is selected, or wherein responsive to the monitoring, a dosage of a non-targeted immune suppressive agent is selected.

243. The method of embodiment 242, wherein the dosage is administered.

244. The method of embodiment 243, wherein the selected dosage is zero, i.e., a non-targeted immune suppressive agent is not administered.

245. The method of embodiment 243, wherein the selected dosage is non-zero, i.e., a non-targeted immune suppressive agent is administered.

246. The method of embodiment 243, wherein the dosage is less than what would be administered in the absence of administration of a therapeutic compound.

247. The method of any of embodiments 196-246, wherein the subject is a mammal, e.g., a non-human mammal.

248. The method of any of embodiments 196-246, wherein the subject is a human.

249. The method of embodiment 213, wherein the donor and subject are mismatched at an HLA locus, e.g., a major or minor locus.

250. The method of embodiment 249, wherein the subject is a mammal, e.g., a non-human mammal.

251. The method of embodiment 249, wherein the subject is a human.

252. A method of treating a subject having, or at risk, or elevated risk, for having, an autoimmune disorder, comprising administering a therapeutically effective amount of a therapeutic compound of any embodiments 1-195, thereby treating the subject.

253. The method of embodiment 252, wherein provision of the therapeutic compound is initiated prior to the onset, or prior to identification of onset, of symptoms of the autoimmune disorder.

254. The method of any of embodiments 252-253, wherein provision of the therapeutic compound is initiated after onset, or after identification of onset, of symptoms of the autoimmune disorder.

255. The method of embodiments 252-254, wherein autoimmune disorder comprises type 1 diabetes.

256. The therapeutic compound of any of embodiments 252-255, wherein the target tissue comprises pancreatic islets or pancreatic beta cells, gut tissue (e.g. gut endothelial cells), kidney tissue (e.g. kidney epithelial cells), or liver tissue (e.g. liver epithelial cells).

257. The therapeutic compound of any of embodiments 252-256, wherein the effector binding/modulating moiety or targeting moiety binds a polypeptide selected from Table 3, e.g., MAdCAM, SEZ6L2, LRP11, DISP2, SLC30A8, FXYD2, TSPAN7, or TMEM27 polypeptide.

258. The method of any of embodiments 252-257, wherein provision of the therapeutic compound is initiated prior to the onset, or prior to identification of onset, of symptoms of type 1 diabetes.

259. The method of any of embodiments 252-258, wherein provision of the therapeutic compound is initiated prior to, or prior to identification of the subject having a preselected characteristic or symptom.

260. The method of any of embodiments 252-259, wherein provision of the therapeutic compound is initiated after onset, or after identification of onset, of symptoms of type 1 diabetes.

261. The method of any of embodiments 252-260, wherein provision of the therapeutic compound is initiated after, or after identification of the subject having a preselected characteristic or symptom.

262, The method of any of embodiments 252-261, wherein the therapeutic compound is a therapeutic compound of any of embodiments 1-195 263 The method of any of embodiments 252-257, wherein therapeutic compound is suitable for the treatment of a subject having, or at risk, or elevated risk, for having, multiple sclerosis.

264. The method of embodiment 263, wherein the target tissue comprises CNS tissue, myelin sheath, or myelin sheath of oligodendrocytes.

265. The method of any of embodiments 263 or 264, wherein the effector binding/modulating moiety or targeting moiety binds a polypeptide selected from Table 3, e.g., a MOG, PLP, or MBP polypeptide.

266. The method of any of embodiments 263-265, wherein provision of the therapeutic compound is initiated prior to the onset, or prior to identification of onset, of symptoms of multiple sclerosis.

267. The method of any of claim embodiments 263-265, wherein provision of the therapeutic compound is initiated prior to, or prior to identification of the subject a preselected characteristic or symptom.

268. The method of any of embodiments 263-265, wherein provision of the therapeutic compound is initiated after onset, or after identification of onset, of symptoms of multiple sclerosis.

269. The method of any of embodiments 263-265, wherein provision of the therapeutic compound is initiated after, or after identification of the subject having a preselected characteristic or symptom.

270. The method of any of embodiments 263-269, wherein the therapeutic compound is a therapeutic compound of any of embodiments 1-195

271. The method of any of embodiments 252-257, wherein the therapeutic compound is suitable for the treatment of a subject having, or at risk, or elevated risk, for having, cardiomyositis.

272. The method of embodiment 271, wherein the target tissue comprises cardiomyocytes, monocytes, macrophages, or myeloid cells.

273. The method of embodiments 271 or 272, wherein the effector binding/modulating moiety or targeting moiety binds a polypeptide selected from Table 3, e.g., a SIRPA (CD172a) polypeptide.

274. The method of any of embodiments 271-273, wherein provision of the therapeutic compound is initiated prior to the onset, or prior to identification of onset, of symptoms of cardiomyositis.

275. The method of any of embodiments 271-273, wherein provision of the therapeutic compound is initiated prior to, or prior to identification of the subject having a preselected characteristic or symptom.

276. The method of any of embodiments 271-273, wherein provision of the therapeutic compound is initiated after onset, or after identification of onset, of symptoms of cardiomyositis.

277. The method of any of embodiments 271-273, wherein provision of the therapeutic compound is initiated after, or after identification of the subject having a preselected characteristic or symptom.

278. The method of any of embodiments 271-277, wherein the therapeutic compound is a therapeutic compound of any of embodiments 1-195.

279. The method of any of embodiments 252-257, wherein therapeutic compound is suitable for the treatment of a subject having, or at risk, or elevated risk, for having, rheumatoid arthritis.

280. The method of embodiment 279, wherein the target tissue comprises cardiomyocytes, monocytes, macrophages, or myeloid cells.

281. The method of embodiments 279 or 280, wherein the effector binding/modulating moiety or targeting moiety binds a polypeptide selected from Table 3, e.g., a SIRPA (CD172a) polypeptide.

282. The method of embodiments 279-281, wherein provision of the therapeutic compound is initiated prior to the onset, or prior to identification of onset, of symptoms of rheumatoid arthritis.

283. The method of embodiments 279-281, wherein provision of the therapeutic compound is initiated prior to, or prior to identification of the subject having a preselected characteristic or symptom.

284. The method of embodiments 279-281, wherein provision of the therapeutic compound is initiated after onset, or after identification of onset, of symptoms of rheumatoid arthritis.

285. The method of embodiments 279-281, wherein provision of the therapeutic compound is initiated after, or after identification of the subject having a preselected characteristic or symptom.

286. The method of embodiments 279-285, wherein the therapeutic compound is a therapeutic compound of any of embodiments 1-195.

287. The method of any of embodiments 196-286, comprising monitoring the subject for immune cell inactivation (e.g., to monitor unwanted agonization of an immune inhibitory checkpoint molecule) at a site distant from the target site, e.g., in the peripheral circulation or the lymphatic system.
288. The method of any of embodiments 196-287, comprising monitoring the subject for immune cell activation (e.g., to monitor unwanted antagonization of an immune inhibitory checkpoint molecule) at a site distant from the target site, e.g., in the peripheral circulation or the lymphatic system.
289. The method of any of embodiments 196-288, wherein responsive to the result of monitoring, selecting a course of treatment for the subject, e.g., increasing the dose of the therapeutic compound, decreasing the dose of the therapeutic compound, continuing treatment with the therapeutic compound without a change in dose.
290. The method of any of embodiments 196-289, wherein the subject monitored for autoimmune attack of the target tissue.
291. The method of embodiment 290, wherein responsive to the monitoring, a dosage of the therapeutic compound is selected.
292. The method of embodiment 291, wherein the dosage is administered.
293. The method of embodiment 290, wherein the selected dosage is zero, i.e., administration of therapeutic compound is ceased.
294. The method of embodiment 290, wherein the selected dosage is non-zero.
295. The method of embodiment 290, wherein the selected dosage is an increased dosage.
296. The method of embodiment 290, wherein the selected dosage is an reduced dosage.
297. The method of any of embodiments 196-296, wherein administering comprises systemic administration, e.g., to the peripheral circulatory system.
298. The method of any of embodiments 196-297, wherein administering comprises local administration, e.g., to the target tissue.
299. The method of any of embodiments 196-298, comprising administering a therapeutic compound provided herein such that therapeutic levels are present for at least 1, 5, 10, 14, or 28 days, e.g, consecutive or non-consecutive days.
300. The method of any of embodiments 196-299, wherein the subject is a mammal, e.g., a non-human mammal.
301. The method of any of embodiments 196-299, wherein the subject is a human.
302. A nucleic acid molecule or a plurality of nucleic acid molecules encoding a therapeutic compound of any of embodiments 1-195.
303. A vector or a plurality of vectors comprising the nucleic acid molecules of embodiment 302.
304. A cell comprising the nucleic acid molecules of embodiment 302 or the vector of embodiment 303.
305. A method of making a therapeutic compound comprising culturing a cell of embodiment 304 to make the therapeutic compound.
306. A method of making a nucleic acid sequence encoding a therapeutic compound of any of embodiments 1-195, comprising
    a) providing a vector comprising sequence encoding a targeting moiety and inserting into the vector sequence encoding an effector binding/modulating moiety to form a sequence encoding a therapeutic compound; or
    b) providing a vector comprising sequence encoding an effector binding/modulating moiety and inserting into the vector sequence encoding a targeting moiety to form a sequence encoding a therapeutic compound,
thereby making a sequence encoding a therapeutic compound.
307. The method of embodiment 306, wherein the targeting moiety is selected in response to the need of a subject.
308. The method of embodiment 306 or 307, wherein the effector binding/modulating moiety is selected in response to the need of a subject.
309. The method of any of embodiments 306 or 307, further comprising expressing the sequence encoding the therapeutic compound to produce the therapeutic compound.
310. The method of any of embodiments 306-309, further comprising transferring the sequence, or a polypeptide made from the sequence, to another entity, e.g., a health care provider who will administer the therapeutic compound to a subject.
311. A method of treating a subject comprising:
    acquiring, e.g., receiving from another entity, a therapeutic compound, or a nucleic acid encoding a therapeutic compound, made by the method of any of provided herein, but not limited to embodiments 306-310;
    administering the therapeutic compound, or a nucleic acid encoding a therapeutic compound to the subject, thereby treating the subject.
312. The method of embodiment 311, further comprising identifying the therapeutic compound, or nucleic acid encoding a therapeutic compound to another entity, e.g., the entity that will make the therapeutic compound, or nucleic acid encoding a therapeutic compound.
313. The method of embodiments 311 or 312, further comprising requesting the therapeutic compound, or nucleic acid encoding a therapeutic compound from another entity, e.g., the entity that made the therapeutic compound, or nucleic acid encoding a therapeutic compound.
314. The method of any of embodiments 311-333, wherein the subject has an autoimmune disorder and the therapeutic compound does not comprise an autoantigenic peptide or polypeptide characteristic of the autoimmune disorder, e.g., does not comprise a peptide or polypeptide against which the subject has autoantibodies.

The following examples are illustrative, but not limiting, of the compounds, compositions and methods described herein. Other suitable modifications and adaptations known to those skilled in the art are within the scope of the following embodiments.

EXAMPLES

Example 1: HLA-Targeted Pd-1 Agonizing Therapeutic Compounds

Engineering of a HLA-Targeted PD-1-Agonizing Therapeutic

Binding domains specific for HLA-A2 are obtained by cloning the variable regions of the Ig heavy and light chains from the BB7.2 hybridoma (ATCC) and converting into a single-chain Ab (scFv). Activity and specificity of the scFv can be confirmed by assessing binding of BB7.2 to HLA-A2 expressing cells in comparison to cells expressing other HLA-A alleles. The minimal PD-L1 residues required for PD-1 binding activity are identified by systematically evaluating the requirement of amino acids 3' and 5' of the PD-L1 IgV domain corresponding to amino acids 68-114. Expression constructs are designed and proteins synthesized and purified, with PD-1 binding activity tested by Biacore. The minimum essential amino acids required for PD-1 binding by the PD-L1 IgV domain are referred to as PD-L1-IgV. To generate a BB7.2 scFv and PD-L1-IgV bi-specific molecule, a DNA fragment is synthesized encoding the bispecific single-chain antibody BB7.2×PD-L1-IgV with the domain arrangement $VL_{BB7.2}$-$VH_{BB7.2}$-PD-L1-IgV-IgG4 Fc and cloned into an expression vector containing a DHFR selection cassette.

Expression vector plasmid DNA is transiently transfected into 293T cells, and BB7.2×PD-L1-IgV bispecific antibodies are purified from supernatants using a protein A/G column. BB7.2×PD-L1-IgV bispecific antibody integrity is assessed by polyacrylamide gel. Binding of the BB7.2 scFv domain to HLA-A2 and PD-L1-IgV domain to PD-1 is assessed by ELISA and cell-based FACS assay.

The in vitro function of BB7.2×PD-L1-IgV bispecific antibodies is assessed using mixed lymphocyte reaction (MLR) assay. In a 96-well plate format, 100,000 irradiated human PBMCs from an HLA-$A2^+$ donor are aliquoted per well and used as activators. HLA-$A1^-$ responder T cells are then added together with increasing amounts of BB7.2×PD-L1-IgV bispecific antibody. The ability of responder T cells to proliferate over a period of 72 hours is assessed by BrdU incorporation, and with IFNg and IL2 cytokine production additionally evaluated in the co-culture supernatant as assessed by ELISA. BB7.2×PD-L1-IgV bispecific antibody is found to suppress MLR reaction as demonstrated by inhibiting HLA-$A2^-$ responder T cell proliferation and cytokine production.

The in vivo function of BB7.2×PD-L1-IgV bispecific antibody is assessed using a murine mouse model of skin allograft tolerance. The C57BL/6-Tg(HLA-A2.1)1Enge/J (Jackson Laboratories, Bar Harbor Me.) strain of mouse is crossed with Balb/cJ, with F1 progeny expressing the HLA-A2.1 transgene and serving as allograft donors. C57BL/6J mice are shaved and surgically engrafted with skin removed from euthanized C57BL/6-Tg(HLA-A2.1)1Enge/J×Balb/cJ F1 mice. At the same time, host mice start receiving intraperitoneal injections of the BB7.2×PD-L1-IgV bispecific antibody engineered to contain a murine IgG1 Fc or BB7.2 only or PD-L1-IgV only controls. Skin allograft rejection or acceptance is monitored over a period of 30 days, wherein hosts were euthanized and lymph node and allograft-resident lymphocyte populations quantified.

Example 2: CD39 and/or CD73 as Effector Domains Creating a Purinergic Halo Surrounding a Cell Type or Tissue of Interest A catalytically active fragment of CD39 and/or CD73 is fused to a targeting domain. Upon binding and accumulation at the target site, CD39 phosphohydrolyzes ATP to AMP. Upon binding and accumulation at the target site, CD73 dephosphorylates extracellular AMP to adenosine. A soluble catalytically active form of CD39 suitable for use herein has been found to circulate in human and murine blood, see, e.g., Yegutkin et al. FASEB J. 2012 September; 26(9):3875-83. A soluble recombinant CD39 fragment is also described in Inhibition of platelet function by recombinant soluble ecto-ADPase/CD39, Gayle, et al., J Clin Invest. 1998 May 1; 101(9): 1851-1859. A suitable CD73 molecule comprises a soluble form of CD73 which can be shed from the membrane of endothelial cells by proteolytic cleavage or hydrolysis of the GPI anchor by shear stress see, e.g., Reference: Yegutkin G, Bodin P, Burnstock G. Effect of shear stress on the release of soluble ecto-enzymes ATPase and 5'-nucleotidase along with endogenous ATP from vascular endothelial cells. Br J Pharmacol 2000; 129: 921-6.

The local catalysis of ATP to AMP or AMP to adenosine will deplete local energy stores required for fulminant T effector cell function. Treg function should not be impacted by ATP depletion due to their reliance on oxidative phosphorylation for energy needs (which requires less ATP), wherein T memory and other effector cells should be impacted due their reliance on glycolysis (requiring high ATP usage) for fulminant function.

Example 3: Measuring Antibody-Induced PD-1 Signaling

Jurkat cells that stably express 2 constructs, 1) a human PD-1 polypeptide fused to a b-galactosidase, which can be referred to as an "Enzyme donor" and 2) a SHP-2 polypeptide fused to a b-galactosidase, which can be referred to as an "Enzyme acceptor." A PD-1 antibody is contacted with the cell and when the PD-1 is engaged, SHP-2 is recruited to PD-1. The enzyme acceptor and enzyme donor form a fully active b-galactosidase enzyme that can be assayed. This assay can be used to show activation of PD-1 signaling.

Example 4: Measuring PD-1 Agonism. PD-1 Agonists Inhibit T Cell Activation

Without being bound to any particular theory, PD-1 agonism inhibits anti-CD3-induced T cell activation. Human or mouse cells are preactivated with PHA (for human T cells) or ConA (for mouse T cells) so that they express PD-1. The T cells are then "reactivated" with anti-CD3 in the presence of anti-PD-1 (or PD-L1) for the PD-1 agonism assay. T cells that receive a PD-1 agonist signal in the presence of anti-CD3 will show decreased activation, relative to anti-CD3 stimulation alone. Activation can be readout by proliferation or cytokine production (IL-2, IFNg, IL-17) and possibly by other markers, such as CD69 activation marker.

Example 5. Expression and Function of Anti-MAdCAM/Mouse PD-L1 Fusion Protein is not Impacted by Molecular Configuration A bispecific fusion molecule comprising an anti-mouseMAdCAM Ab/mouse PD-L1 molecule was expressed in two orientations. The first orientation consisted of an anti-mouse MAdCAM IgG with mouse PD-L1 fused at the c-terminus of it's heavy chain. The second orientation consisted of mouse PD-L1 fused at the N-terminus of an Ig Fc domain, with a c-terminally fused anti-mouse MAdCAM scFv. Both molecules were found to be well expressed in a mammalioan expression system. It was also found that the molecules can bind to their respective binding partners, MAdCAM or PD-1 in both orientations, simultaneously. These results demonstrate that a molecule consisting of an anti-MAdCAM antibody fused to PD-L1, can be expressed in configurations whereby PD-L1 is N or C-terminally fused to the Fc and retain proper functional binding activity.

Briefly, a pTT5 vector containing the single gene encoding a single polypeptide with mouse PD-L1 fused N-terminally of human IgG1 Fc domain and with c-terminal fused anti-MAdCAM scFv MECA-89 was transfected into HEK293 Expi cells. Alternatively, two plasmids were co-transfected at equimolar ratios. The first plasmid encoded the light chain of MECA-89 and the 2nd encoded the full length IgG1 heavy chain of MECA-89 with c-terminally fused mouse PD-L1. After 5-7 days, cell culture supernatants expressing the molecules were harvested, and clarified by centrifugation and filtration through a 0.22 um filtration device. The bi-specific molecules were captured on proA resin. The resin was washed with PBS pH 7.4 and the captured molecule was eluted using 100 mM Glycine pH 2.5, with neutralization using a tenth volume of 1M Tris pH 8.5. The protein was buffer exchanged into PBS pH 7.4, and analyzed by size exclusion chromatography on a Superdex 200 3.2/300. Analysis of 1 ug of purified material by reducing and non-reducing SDS-PAGE on a Bis-Tris 4-12% gel was conducted.

Both proteins, regardless of orientation were expressed at over 10 mg/L, and were over 95% monodispersed after purification as shown by size exclusion chromatography and reducing/non-reducing SDS-PAGE. Accordingly, this demonstrates the production and activity of dual function bispecific molecules with different immunomodulators and tissue targeting moieties at the N and C terminus of an Fc domain. This also shows specifically that a PD-1 agonist and binding partner can be expressed at the N or C terminus of an Ig Fc domain.

Example 6. A Bispecific Molecule Comprising a PD-1 Agonist Protoytpe Tethered to MAdCAM can Bind MAdCAM and PD-1 Simultaneously Briefly, an immunosorbent plate was coated with mouse PD-1 at a concentration of 1 ug/mL in PBS pH 7.4, 75 ul/well, and incubated overnight at 4° C. Wells were washed with PBS pH 7.4 containing 0.05% Tween-20 (wash buffer) three times, and then blocked with 200 ul/well 1% BSA in PBS pH 7.4 (block buffer) for two hours at room temperature. After three washes with wash buffer, two bispecific molecules that comprises the PD-1 Agonist prototype at either the N-terminus or C-terminus were diluted to 1 nM, 10 nM, and 100 nM in PBS containing 1% BSA and 0.05% Tween-20 (assay buffer). The diluted material was added to the mouse PD-1 coated plate at 75 ul/well for 1 hour at room temperature. After three washes with wash buffer, mouse MAdCAM was added to the plate at 75 ul/well, at a concentration of 10 nM in assay buffer for 1 hr at room temperature. After three washes with wash buffer, a goat biotinylated anti-mouse MAdCAM polyclonal antibody, diluted to 0.5 ug/mL in assay buffer, was added to the plate at 75 ul/well for 1 hr at room temperature. After three washes with wash buffer high sensitivity streptavidin HRP diluted in assay buffer at 1:5000 was added to the plate at 75 ul/well for 15 minutes at room temperature. After three washes with wash buffer and 1 wash with wash buffer (with no tween-20), the assay was developed with TMB, and stopped with 1N HCL. OD 450 nm was measured. The experiment included appropriate controls for non-specific binding to the plate/block in the absence of mouse PD-1, as well as no MAdCAM controls, and mono-specific controls, that are unable to form a bridge between mouse PD-1 and mouse MAdCAM.

The results demonstrated that at concentrations of 1 nM, 10 nM, and 100 nM, both bispecific molecules, are able to simultaneously interact with mouse MAdCAM and mouse PD-L1, whilst the monospecific controls did not create a bridging signal. Additionally, there was no binding of any compound to MAdCAM at any concentration tested, when mouse PD-1 was not present on the plate surface, indicating none of the test compounds were interacting non-specifically with the plate surface. Thus, these results demonstrate that a bispecific molecule that is targeting binding to both MAdCAM and PD-1 can successfully bind to both molecules. Although the experiments were performed with PD-L1 as a substitute for a PD-1 antibody, it is expected that the PD-1 antibody will function in a similar manner.

Example 7. A Bispecific PD-L1 Prototype Molecule Inhibits T Cells in a PD-1 Agonist Assay A bispecific molecule that mimics a PD-1 agonist antibody was tested to demonstrate that PD-1 agonism can inhibit T cells. Briefly, 7 week old female C57LB/6 mice were sacrificed and their splenocytes were isolated. The splenocytes were exposed to ConA for 3 days and then exposed to anti-CD3 in the presense or absence of the PD-1 type molecule, which in this example was a PD-L1 bispecific molecule that was tethered to a plate using anti-human IgG. T cells were then introduced to the PD-L1 bispecific molecule. The PD-L1, which mimics a PD-1 antibody were found to be a T cell agonist and inhibit T cell activation. The same experiments were repeated using a PD-L1 bispecific molecule that was fused with an anti-MAdCAM antibody, which were tethered to a plate by interacting with a MAdCAM coated plate. The PD-1 agonist mimic, the PD-L1/anti-MAdCAM antibody were found to be effective agonists of T cell activity. These results demonstrate that a bispecific molecule that mimics a PD-1 antibody/MAdCAMAb fusion protein can exert functional inhibitory signaling into primary mouse T cell blasts when the molecule is captured via the MAdCAM antibody component at the end of the molecule.

Example 8: A Bispecific PD-1 Prototype Molecule with a Different Tissue Tether can Inhibit T Cells in a PD-1 Agonist Assay A fusion molecule of a PD-L1 was used as a substitute for a PD-1 antibody and linked to a Class I H-2Kk antibody. The MHC Class I H-2Kk tethered PD-L1 molecule had functional binding, similar to the data described in Examples 6 and 7. Briefly, splenocytes from C57Bl/6 mice were stimulated with Concanavalin A (ConA) and IL-2 for 3 days. Plates were coated with anti-CD3 (2C11) overnight at 4 C, washed. Plates were coated with anti-human IgG for 3 hrs at 37 C and washed. Mono-specific anti-H-2Kk (16-3-22) or bi-specific anti-H-2Kk:mPD-L1 were added and incubated for 3 hr at 37 C and washed. All test articles contained a human IgG1-Fc portion. PBS (No Tx) was added to determine the assay background. ConA blasts were washed 2 times, added to the plate and incubated at 37 C. Supernatants were removed after 24 hrs. IFNg levels were determined by MSD. After 48 hrs, cell viability/metabolism was analyzed by Cell Titer-glo. When captured via the IgG Fc domain, an MHC Class I tethered PD-L1 bispecific can attenuate T cell activation in a mouse PD-1 agonism assay. Therefore, this example demonstrates that a different bispecific prototype molecule can exert functional inhibitory signaling into primary mouse T cell blasts—when the molecule is captured via a different tissue tether—in this case a mouse antibody to MHC Class I H-2Kk. Accordingly, this data demonstrates that the tethering is not specific to MAdCAM and is possible with other molecules that can act as targeting moieties as provided herein.

Example 9. PD-1 Agonists can Induce Signaling in Jurkat Cells

Jurkat cells expressing both human PD-1 fused to a beta-galactosidase enzyme donor and SHP-2 fused to a beta-galactosidase enzyme acceptor are added to test conditions in a plate and incubated for 2 hrs. Agonist PD-1 antibodies induce signaling and SHP-2 recruitment, enzyme complementation and formation of an active beta-galactosidase enzyme. Beta-galactosidase substrate was added and chemiluminescence can be measured on a standard luminescence plate reader. Agonism is measured by chemiluminescence, where the more chemiluminescence that is measured indicates the greater agonism.

Agonism of a PD-1/MAdCAM bi-specific molecule was measured in this assay. Cl10 (UCB) and CC-90006 (Celgene/Anaptys) were used as PD-1 agonist antibodies. Both are active and exhibit PD-1 agonism in functional assay in Ig-capture assay format. Briefly, plates were coated with anti-human IgG for overnight at 4 C and washed. Anti-tetanus toxin (TT) or benchmark agonist anti-PD-1 monoclonal antibodies, C1.10 or CC-90006 were added and incubated for 1 hr at 37 C and washed. All test articles contained a human IgG1-Fc. Media (No Tx) was added to determine the assay background. Plates were washed 3 times. Jurkat cells expressing both human PD-1 fused to a b-galactosidase enzyme donor and SHP-2 fused to a b-galactosidase enzyme acceptor were added and incubated for 2 hrs. Agonist PD-1 antibodies induce signaling and SHP-2 recruitment, enzyme complementation and formation of an active b-galactosidase enzyme. B-galactosidase substrate was added and chemiluminescence was measured on a standard luminescence plate reader. The two human PD-1 agonist antibodies (Cl10 and CC-90006) bind and induce signaling (a surrogate for agonism) in the modified Jurkat reporter assay. Thus, this assay is a functional PD-1 agonism assay. Cl10:MECA89 (MECA89 is a known MAdCAM antibody) is a novel bispecific molecule created by fusing MAdCAM antibody, MECA89[scFv], to C-terminus of the heavy chain of Cl10. This fusion protein was found to be active and exhibit PD-1 agonism in functional assay when captured via IgG Fc domain, as was Cl10 only protein. However, only Cl10:MECA89 is active in functional assay format using MAdCAM protein as capture (the monospecific components do not signal).

Briefly, plates were coated with either anti-human IgG or recombinant mMAdCAM-1 overnight at 4 C and washed. Mono-specific Anti-tetanus toxin (TT), anti-MAdCAM-1 (MECA39) or agonist anti-PD-1 (Cl10) or bi-specific Cl10:MECA89 were added and incubated for 1 hr at 37 C and washed. All test articles contained a human IgG1-Fc portion. PBS (No Tx) was added to determine the assay background. Plates were washed 2 times. Jurkat cells expressing both human PD-1 fused to a b-galactosidase enzyme donor and SHP-2 fused to a b-galactosidase enzyme acceptor were added and incubated for 2 hrs. Agonist PD-1 antibodies induce signaling and SHP-2 recruitment, enzyme complementation and formation of an active b-galactosidase enzyme. B-galactosidase substrate was added and chemiluminescence was measured on a standard luminescence plate reader. Results: Both Cl10, and the MAdCAM-tethered Cl10 bispecific molecules can induce PD-1 signaling in the Jurkat reporter assay when the plate is coated with an anti-IgG Fc capture, but only the MAdCAM-tethered bispecific can induce PD-1 signaling in the reporter assay when the plate is coated with recombinant MAdCAM protein. These results demonstrate that the molecule tethered with MAdCAM and contains a PD-1 agonist antibody are functional, which is similar to the results shown with the PD-L1 as the PD-1 agonist surrogate.

Example 10: Generation of PD-1 Agonist Antibodies

PD-1 deficient mice immunized with mouse PD-1 under conditions to generate an immune response against PD-1. 54 hybridomas were generated and identified that bind mouse PD-1. The antibodies produced by the different hybridomas were analyzed for T cell agonism according to the methods described in Examples 4 and 6. Out of the 54 hybridomas at least 6 were identified as PD-1 agonists. The antibodies were also tested for binding on PD-1 and were found to bind at the same site as the PD-L1 binding site.

Briefly, binding to the PD-L1 binding site was determined using the following assay. Immunosorbent plates were coated overnight with 75 µL of recombinant mouse PD-L1-Fc (2 µg/mL) in 1×PBS, pH 7.4. Plates were then washed 3× with 1×PBS and blocked for 2 hours at room temperature with 1×PBS supplemented with 1% BSA. Recombinant mouse PD-1-Fc (1 nM) was incubated with 100 nM of the indicated anti-mouse PD-1 antibody in 1×PBS supplemented with 1% BSA and 0.05% Tween20 (Assay Buffer) for 1 hour at room temperature, shaking. After blocking, plates were washed 3× with 1×PBS supplemented with 0.05% Tween20 PBST and the antibody-PD-1 conjugates were incubated with plate-bound mouse PD-L1. After washing away unbound PD-1 with PBST, plates were incubated with 75 µL of biotinylated, polyclonal anti-PD-1 antibody (0.5 µg/mL) in assay buffer, followed by amplification with 1:5000 streptavidin HRP also diluted in assay buffer. Plates were washed three times with PBST followed by three washes with 1×PBS before addition of 100 µL TMB followed by 100 µL 1M HCl to stop the developing. Absorbance read at 450 nm and normalized to binding of PD-1 to PD-L1 in the absence of antibody. The results showed that the active antibodies bind to the PD-L1 binding site. The inactive antibodies did not bind to the PD-L1 binding site. Therefore, this example demonstrates the ability to produce anti-PD-1 antibodies that are agonists, in addition to the previously identified PD-1 agonist antibodies described herein.

Example 11: Tethered Anti-PD-1 Antibodies Acts as PD-1 Agonists

A human antibody scFv phage library was panned against recombinant human, mouse, and cyno PD-1 proteins across iterative selection rounds to enrich for antibody clones that recognize all three aforementioned species orthologues of PD-1. The scFv clones were configured in nt-VH-Linker-VL-ct format and fused to the M13 phage surface via the pIII coat protein. After selections, clonal scFvs were screened for binding to human, mouse, and cyno PD-1 expressed on the cell surface of CHO cells. Clones that were found to be cross reactive to all three cell surface expressed PD-1 species orthologues were converted using standard molecular biology techniques, into a human IgG1 format whereby each molecule was comprised of four polypeptide chains in total (2 heavy, and 2 light chains). The two light chains were identical to each other and the two heavy chains were identical to each other as provided.

The two identical heavy chains homodimerize and the two identical light chains pair with each heavy chain to form an intact human IgG1. The Fc domain contains the L235A, L236A, and G237A mutations to ablate FcγR interactions. The converted human IgG1 anti-PD-1 antibodies were transfected and expressed in HEK293 Expi cells, and purified by protein A chromatography. The protein concentration was determined using a nanodrop spectrophotometer in conjunction with antibody specific extinction coefficients. Antibodies were formulated in PBS pH 7.4.

The anti-PD-1 antibodies were next tested in the Jurkat assay described herein for agonist activity. Briefly, tissue culture plates were coated with anti-IgG or left uncoated. For captured format, test articles or controls were added to the anti-IgG coated wells at 100 nM, 25 nM or 12.5 nM and incubated for 3 hrs at 37 C. Plates were washed and Jurkat PD-1 cells were added. For the soluble format, soluble test articles or controls were added to wells at 100 nM, 25 nM or 12.5 nM already containing Jurkat PD1 cells. Luminescence was measured in a plate reader. The results demonstrated that nine of the twelve human/mouse cross-reactive PD-1 antibodies showed dose-dependent activity in the Jurkat assay when the anti-PD-1 antibodies were captured via anti-IgG, but not in the soluble format. This data demonstrates that the anti-PD-1 antibody can act as an agonist when tethered to its target by a targeting moiety.

In conclusion, without being bound to any particular theory, the data presented herein demonstrate that a PD-1 Agonist/MAdCAM bi-specific molecule can bind to both MAdCAM and PD-1 and also agonize T cell activity. Thus, the molecules can be used to treat the various conditions provided herein and provide for localized and/or tissue specific immunomodulation and the down regulation of a T-Cell response.

The disclosures of each and every patent, patent application, and publication cited herein are hereby incorporated herein by reference in their entirety. While various embodiments have been disclosed with reference to specific aspects, it is apparent that other aspects and variations of these embodiments may be devised by others skilled in the art without departing from the true spirit and scope of the embodiments. The appended claims are intended to be construed to include all such aspects and equivalent variations.

What is claimed is:

1. A therapeutic compound having the formula from N-terminus to C-terminus:
   Chain 1: [VH1-CH1]-[CH2-CH3]-Linker A-scFv;
   Chain 2: [VH1-CH1]-[CH2-CH3]-Linker A-scFv;
   Chain 3: [VL1-CL]; and
   Chain 4: [VL1-CL];
   wherein chains 1 and 2 are identical to each other, and chains 3 and 4 are identical to each other;
   wherein chain 1 forms a homodimer with chain 2, and chain 3 and 4 associate with each VH1-CH1 domain of chain 1 and chain 2 to form two functional Fab units;
   wherein CH2-CH3 comprises the Fc region;
   wherein each Fab unit is an anti-PD-1 agonist antibody and each scFv unit is a scFv that binds to MAdCAM;
   wherein each scFv unit has the formula of 5'-VL2-Linker B-VH2-3', or 5'-VH2-Linker B-VL2-3'
   wherein Linker A and Linker B are each, independently, a peptide linker.

2. A nucleic acid encoding a therapeutic compound of claim 1.

3. The therapeutic compound of claim 1, wherein the Fab unit is a Fab or scFab.

4. The therapeutic compound of claim 1, wherein the peptide linker comprises glycine, serine, or alanine amino acid residues.

5. The therapeutic compound of claim 1, wherein the peptide linker is a glycine/serine linker.

6. A therapeutic compound comprising a polypeptide, wherein the polypeptide consists of a polypeptide having the formula from N-terminus to C-terminus:
   Chain 1: [VH1-CH1]-[CH2-CH3]-Linker A-scFv
   Chain 2: [VH1-CH1]-[CH2-CH3]-Linker A-scFv
   Chain 3: [VL1-CL]
   Chain 4: [VL1-CL];
   wherein chains 1 and 2 are identical to each other, and chains 3 and 4 are identical to each other;
   wherein chain 1 forms a homodimer with chain 2, and chain 3 and 4 associate with each VH1-CH1 domain of chain 1 and chain 2 to form two functional Fab units;
   wherein CH2-CH3 comprises the Fc region;
   wherein each Fab unit is an anti-PD-1 agonist each scFv unit is a scFv that binds to MAdCAM;
   wherein each scFv unit has the formula of 5'-VL2-Linker B-VH2-3', or 5'-VH2-Linker B-VL2-3'
   wherein Linker A and Linker B are each, independently, a peptide linker.

7. A composition comprising a single active therapeutic compound, wherein the single active therapeutic compound is the therapeutic compound of claim 1.

* * * * *

UNITED STATES PATENT AND TRADEMARK OFFICE
CERTIFICATE OF CORRECTION

| | | |
|---|---|---|
| PATENT NO. | : 10,961,310 B2 | Page 1 of 1 |
| APPLICATION NO. | : 15/922592 | |
| DATED | : March 30, 2021 | |
| INVENTOR(S) | : Viney et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 123 days.

Signed and Sealed this
Thirty-first Day of January, 2023

Katherine Kelly Vidal
*Director of the United States Patent and Trademark Office*